United States Patent
Gao

(10) Patent No.: US 12,116,698 B1
(45) Date of Patent: Oct. 15, 2024

(54) PROTEIN SURFACE RECOGNITION VIA CHEMICALLY ENHANCED PHAGE DISPLAY

(71) Applicant: The Trustees of Boston College, Chestnut Hill, MA (US)

(72) Inventor: Jianmin Gao, Newton, MA (US)

(73) Assignee: The Trustees of Boston College, Chesnut Hill (MA)

( * ) Notice: Subject to any disclaimer, the term of this patent is extended or adjusted under 35 U.S.C. 154(b) by 241 days.

(21) Appl. No.: 17/004,403

(22) Filed: Aug. 27, 2020

Related U.S. Application Data

(60) Provisional application No. 62/895,139, filed on Sep. 3, 2019.

(51) Int. Cl.
| | | |
|---|---|---|
| C40B 40/02 | (2006.01) | |
| A61K 38/00 | (2006.01) | |
| C07K 14/47 | (2006.01) | |
| C12N 7/00 | (2006.01) | |
| C12N 15/10 | (2006.01) | |
| C40B 30/00 | (2006.01) | |
| C40B 30/04 | (2006.01) | |
| C40B 40/00 | (2006.01) | |
| G01N 33/50 | (2006.01) | |

(52) U.S. Cl.
CPC .............. *C40B 40/02* (2013.01); *A61K 38/00* (2013.01); *C07K 14/4723* (2013.01); *C12N 7/00* (2013.01); *C12N 15/1037* (2013.01); *C40B 30/04* (2013.01); *G01N 33/5008* (2013.01); *C40B 30/00* (2013.01); *C40B 40/00* (2013.01)

(58) Field of Classification Search
CPC ......... C40B 40/02; C40B 30/04; C40B 30/00; C40B 40/00; A61K 38/00; C07K 14/4723; C12N 7/00; C12N 15/1037; G01N 33/5008
USPC .......................................................... 435/5
See application file for complete search history.

(56) References Cited

PUBLICATIONS

McCarthy et. al. Phage display of dynamic covalent binding motifs enables facile development of targeted antibiotics. J. Am. Chem. Soc. 2018, 140, 6137-6145. (Year: 2018).*

(Continued)

*Primary Examiner* — Aaron A Priest
*Assistant Examiner* — Randi Lynn Beil
(74) *Attorney, Agent, or Firm* — Lei Fang, Esq.; Smith Tempel Blaha LLC

(57) ABSTRACT

Low molecular weight molecules able to penetrate cells and tissues and having high specificity and affinity for the surfaces of proteins. Methods of making same, pharmaceutical compositions comprising same, and methods of treating cancers, infectious diseases, and diseases and disorders associated with aberrant protein expression using same. A method for selecting a therapeutic peptide for binding to an isolated and/or purified protein of interest by screening a phage display library containing phage particles with phage display peptides which have at least one APBA modified cysteine residue. The APBA modified cysteine residues bind to surface lysine residues on the isolated and/or purified protein of interest by dynamic covalent conjugation to form iminoboronates.

7 Claims, 22 Drawing Sheets
(19 of 22 Drawing Sheet(s) Filed in Color)
Specification includes a Sequence Listing.

(56) References Cited

PUBLICATIONS

McCarthy et. al. Supplementary Information. Phage display of dynamic covalent binding motifs enables facile development of targeted antibiotics. J. Am. Chem. Soc. 2018, 140, S1-S22. (Year: 2018).*
Akcay, G. et al. Nat Chem Biol 2016, 12, 931-936.
Arkin, M. R. et al. Chem Biol 2014, 21, 1102-14.
Arkin, M. R. et al. Nat Rev Drug Discov 2004, 3, 301-17.
Bandyopadhyay, A. et al. Curr Opin Chem Biol 2016, 34, 110-116.
Bandyopadhyay, A. et al. Nature communications 2015, 6, 6561.
Cal, P. M. et al. Chemistry 2015, 21, 8182-7.
Cambray, S. et al. Acc Chem Res 2018, 51, 2198-2206.
Cascioferro, S. et al. J Med Chem 2015, 58, 9108-23.
Crews, C. M. Chem Biol 2010, 17, 551-5.
DeLano, W. L. et al. Science 2000, 287, 1279-1283.
Heinis, C. et al. Nat Chem Biol 2009, 5, 502-7.
Jin, G. et al. PLoS One 2010, 5, e10993.
Kawakami, T. et al. Nat Chem Biol 2009, 5, 888-90.
McCarthy, K. A. et al. J Am Chem Soc 2018, 140, 6137-6145.
Serafimova, I. M. et al. Nat Chem Biol 2012, 8, 471-6.
Wang, J. et al. Frontiers in Microbiology 2018, 9.
Wu, Z. et al. Proceedings of the National Academy of Sciences 2003, 100, 8880-8885.
Yang, J. et al. Medicinal Research Reviews 2019, 39, 265-301.
Zhang, J. et al. Proceedings of the National Academy of Sciences 2014, 111, 13517-13522.

* cited by examiner

PROTEIN SURFACE RECOGNITION VIA CHEMICALLY ENHANCED PHAGE DISPLAY

CROSS REFERENCE TO RELATED APPLICATIONS

This application claims the benefit of U.S. Provisional Application No. 62/895,139, filed on Sep. 3, 2019, which is incorporated herein by reference in its entirety.

STATEMENT REGARDING FEDERALLY SPONSORED RESEARCH OR DEVELOPMENT

This invention was made with U.S. Government support under grant number CHE1904874, awarded by the National Science Foundation. The U.S. government has certain rights in the invention.

CROSS REFERENCE TO SEQUENCE LISTING

The instant application contains a Sequence Listing which has been submitted electronically in ASCII format and is hereby incorporated by reference in its entirety. Said ASCII copy, created on Feb. 23, 2023, is named 940203-1080 SL.txt and is 23,906 bytes in size.

FIELD OF THE INVENTION

The present invention is directed to novel chemically-enhanced phage display libraries for protein surface recognition.

BACKGROUND OF THE INVENTION

Targeted inhibition of important proteins has been a major guiding philosophy of medicinal chemistry. While success has been achieved in the development of inhibitors of enzymes and receptor proteins, many other proteins are considered undruggable due to their lack of a binding pocket that can be targeted by small molecules. Such undruggable proteins often play critical roles in protein-protein or protein-nucleic acid interactions, and hence are appealing targets for the development of therapeutics. Indeed, recent efforts to inhibit protein-protein interactions (PPIs) or target culprit proteins for degradation (via proteolysis targeting chimeras, also known by the acronym PROTAC) have stimulated much interest in medicinal chemistry and are poised to deliver novel therapeutics. To achieve broad success, these new ideas of drug discovery demand facile development of molecular probes that recognize the surface of pocketless proteins. However, to date, no general strategies are available for developing molecules that recognize specific protein surfaces. Select extracellular proteins can be targeted with high potency and specificity using monoclonal antibodies as exemplified by PD-1/PD-L1 inhibitors including nivolumab and pembrolizumab, which have proven to be powerful therapeutics. However, antibody-based therapeutics fall short in cell entry as well as tissue penetration, which greatly limits their utilization.

Antibodies acquire highly potent and specific binding by serving as receptors for their cognate antigens (FIG. 2A). The large size of an antibody (~150 kDa) provides a robust scaffold that tolerates various mutations in the antigen binding site in order to create binding pockets for loops or a set of key residues of the target protein. The binding mode of antibodies to a target protein is the opposite of that of small molecule therapeutics, which typically function as a ligand while the target protein serves as a receptor. Perhaps not surprisingly, in the absence of the needed size and stable structure to present binding pockets, small peptides typically cannot engage in high affinity binding in the manner of antibodies. Consistently, phage display of natural peptide libraries has only yielded peptide binders of modest affinity, with a few exceptions.

Binding events in biology are predominantly driven by noncovalent interactions including hydrophobic interactions, hydrogen bonding, and electrostatic interactions. It has been hypothesized that incorporating additional binding mechanisms could greatly strengthen peptides' affinity to protein surfaces. Specifically, it is believed that dynamic covalent binding mechanisms may be able to complement canonical noncovalent interactions to promote binding. For example, iminoboronate chemistry has been employed to bind amine-presenting lipids of bacterial cells; installing a 2-acetylphenylboronic acid (2-APBA) warhead onto an antimicrobial peptide significantly boosts the peptide's biding to the bacterial pathogen S. aureus. More recently, 2-APBA has been incorporated into a phage displayed peptide library, screening of which allowed quick identification of peptide binders to various bacteria. Some diseases and conditions are marked by aberrant protein expression (e.g., increased expression of a protein when such has a deleterious effect on a subject, or expression of a deleterious mutated protein, or misfolding of a protein) and, for some infectious diseases and conditions, it may be desirable to target proteins excreted by bacterial, fungal, or protozoal cells (e.g., proteolytic enzymes that assist with skin penetration; hemolysins, proteases, peptide and protein endotoxins, invasins, adhesins, antiphagocytic factors, and other virulence factors; and the like) or to target viral proteins (e.g., spike proteins, capsid proteins, envelope proteins, membrane fusion proteins, viral nonstructural and accessory proteins, reverse transcriptases, viral toxins such as, for example, NSP4 from rotavirus, and the like); and/or cancers and proteins expressed by cancerous cells. In some instances, it may be desirable to simultaneously target an enzyme binding pocket and the surface of an enzyme. Furthermore, not all disease-associated proteins are enzymes having druggable binding pockets; thus surface binding to proteins may be required for protein recognition and/or targeting.

It would be highly desirable to develop synthetic, low molecular weight molecules that can be used as a surrogate of antibodies toward protein surface recognition. The low molecular weight molecules would ideally be able to penetrate cells as well as tissues. It would further be desirable to develop peptide binders to protein surfaces having high affinity for the protein surfaces. The peptide binders would be able to inhibit enzymes as well as non-enzyme proteins lacking a targetable binding pocket with single digit micromolar potency and specificity. Ideally, the peptide binders would be specific to the target proteins, even in complex media containing other proteins and other molecules. These needs and other needs are satisfied by the present disclosure.

SUMMARY OF THE INVENTION

In accordance with the purpose(s) of the present disclosure, as embodied and broadly described herein, the disclosure, in one aspect, relates to low molecular weight molecules able to penetrate cells and tissues and having high specificity and affinity for the surfaces of proteins, methods of making same, pharmaceutical compositions comprising same, and methods of treating cancers, infectious diseases caused by bacteria, fungi, and viruses, and diseases and disorders associated with aberrant protein expression using same.

In certain embodiments, the disclosure relates to a method for binding a therapeutic peptide to a protein surface, the method comprising contacting the protein surface with a phage display library comprising phage particles comprising phage display peptides comprising at least one APBA modified cysteine residue. In other embodiments, the disclosure relates to a drug screening method for selection of a therapeutic peptide for binding a protein of interest, the method comprising screening a phage display library comprising phage particles comprising phage display peptides comprising at least one APBA modified cysteine residue with the protein of interest; selecting peptide binders with submicromolar affinity against the protein of interest; and conjugating the selected peptide binders with a therapeutic residue targeting the protein of interest. In any of these aspects, the APBA modified cysteine residues bind to surface lysine residues on the protein of interest by dynamic covalent conjugation to form iminoboronates.

Also disclosed are therapeutic peptides selected using the disclosed methods, pharmaceutical compositions comprising the disclosed therapeutic peptides, methods of treating diseases using the therapeutic peptides, and methods for medical imaging using the therapeutic peptides.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims. In addition, all optional and preferred features and modifications of the described embodiments are usable in all aspects of the disclosure taught herein. Furthermore, the individual features of the dependent claims, as well as all optional and preferred features and modifications of the described embodiments are combinable and interchangeable with one another.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIG. 1I discloses "IEGR—C(X)$_5$C" as SEQ ID NO: 83.

right: top view).

FIG. 8A shows a structure presentation of SrtA showing its non-canonical, shallow binding pocket (top) and the abundance of lysine residues that are amenable to targeting via iminoboronate formation. FIG. 8B shows characterization of the peptides' binding to SrtA via fluorescence imaging of SrtA-coated beads. FIG. 8C shows binding curves generated from fluorescence microscopic studies showing effective binding of W2 to SrtA in the presence of 10 mg/mL bovine serum albumin (BSA). The curves were obtained by plotting mean fluorescence intensity of beads over peptide concentration. FIG. 8D shows binding curves generated via fluorescence anisotropy experiments, in which SrtA was titrated into a peptide solution at increasing concentrations. Curve fitting yielded a $K_d$ value of 12 μm for W2-SrtA binding, which was similar to that obtained from the microscopic studies. FIG. 8E shows a small molecule inhibition assay revealing that W2 binds the SrtA surface instead of the catalytic site. W1 and W2 represent peptide hits binding SrtA.

FIG. 10A shows sequences of the human beta defensins. Figure discloses SEQ ID NOS 76-78, respectively, in order of appearance. FIG. 10B shows microscopic results of SEC1 (10 μM) binding to HBD3 versus HBD2. FIG. 10C shows preliminary titration experiments showing that SEC1 binds HBD3 at low micromolar concentrations, where SEC1 represents a peptide hit binding HBD3.

Figure 1A:
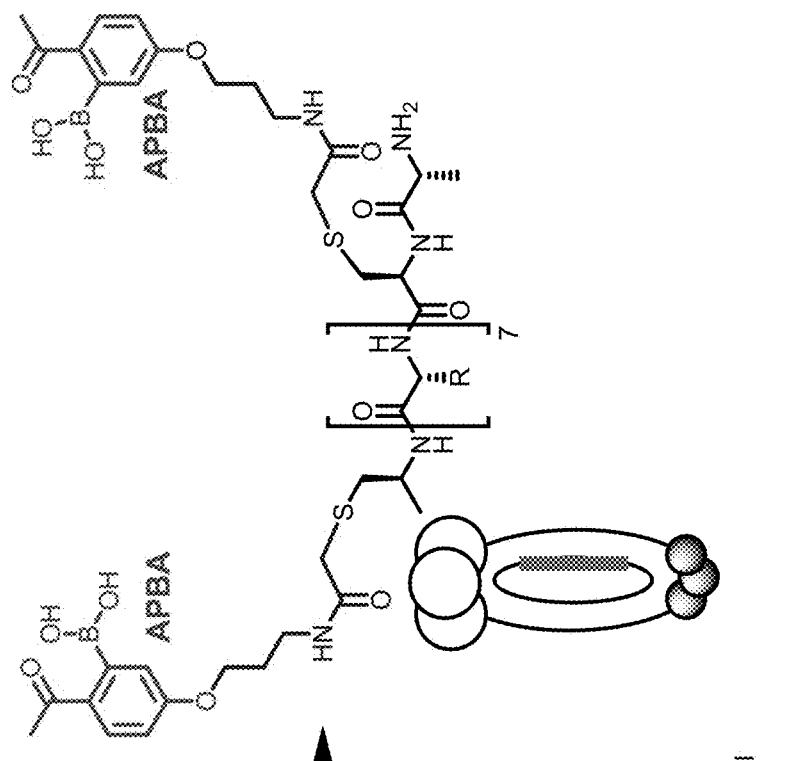
FIG. 1A shows a schematic of a modification reaction for a commercial phage display library (C7C, New England Biolabs) to produce a 2-acetylphenylboronic acid (APBA) dimer library for selection of ligands that interact with protein surfaces.
Figure 1A:
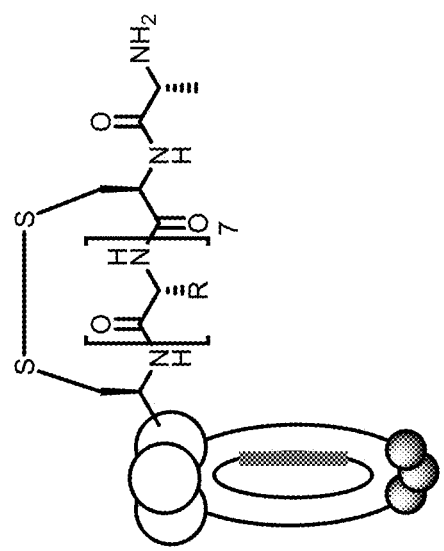
Figure 1B:
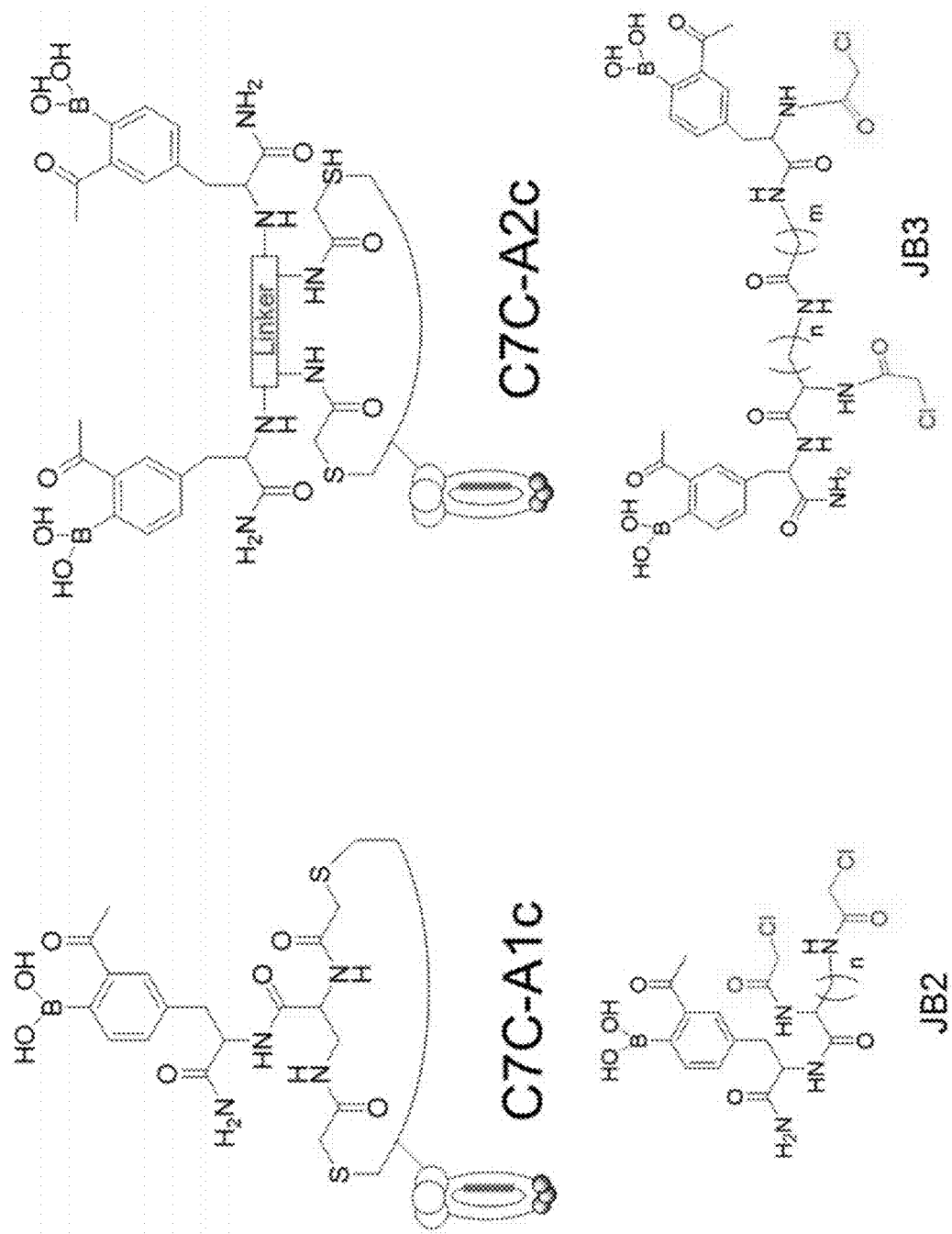
FIG. 1B shows cyclic peptide libraries conjugated to covalent "warheads" or protein surface binding ligands. Left: cyclic peptide library (C7C-A1c) displaying a single warhead, achieved via linking reduced C7C peptides with JB2 (shown at bottom). Right: cyclic peptide library (C7C-A2c) having multiple warheads that can be prepared by linking reduced C7C peptides with JB3 (shown at bottom). The crosslinkers are fully
Figure 1C:
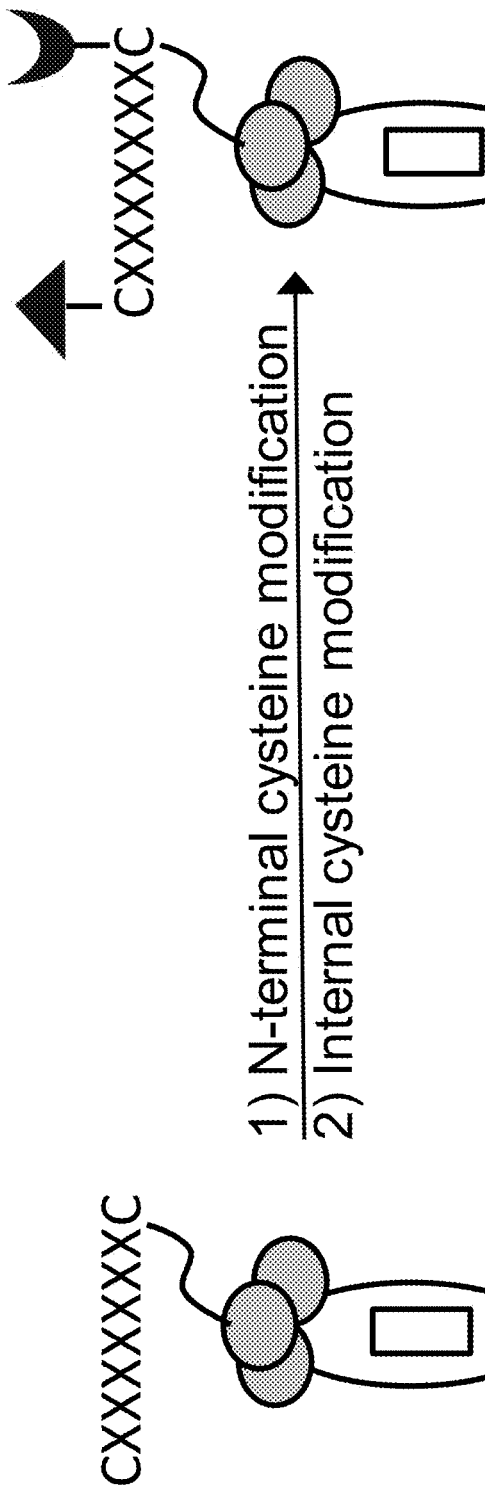
FIG. 1C shows a schematic of phage libraries carrying two distinct "warheads" or protein surface binding ligands. One "warhead" is attached to an N-terminal cysteine residue and another warhead is attached to an internal cysteine residue.
Figure 1D:
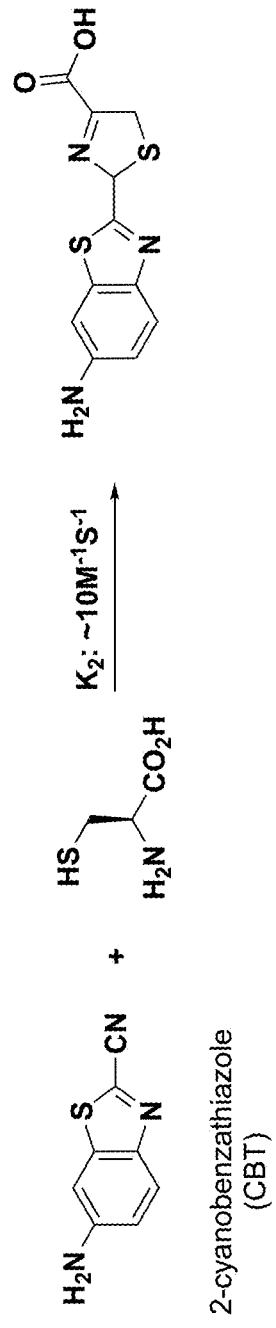
FIG. 1D shows a schematic for the reaction between 2-cyanobenzathiazole (CBT) and a cysteine residue, which allows for selective N-terminal modification of phage proteins.
Figure 1E:
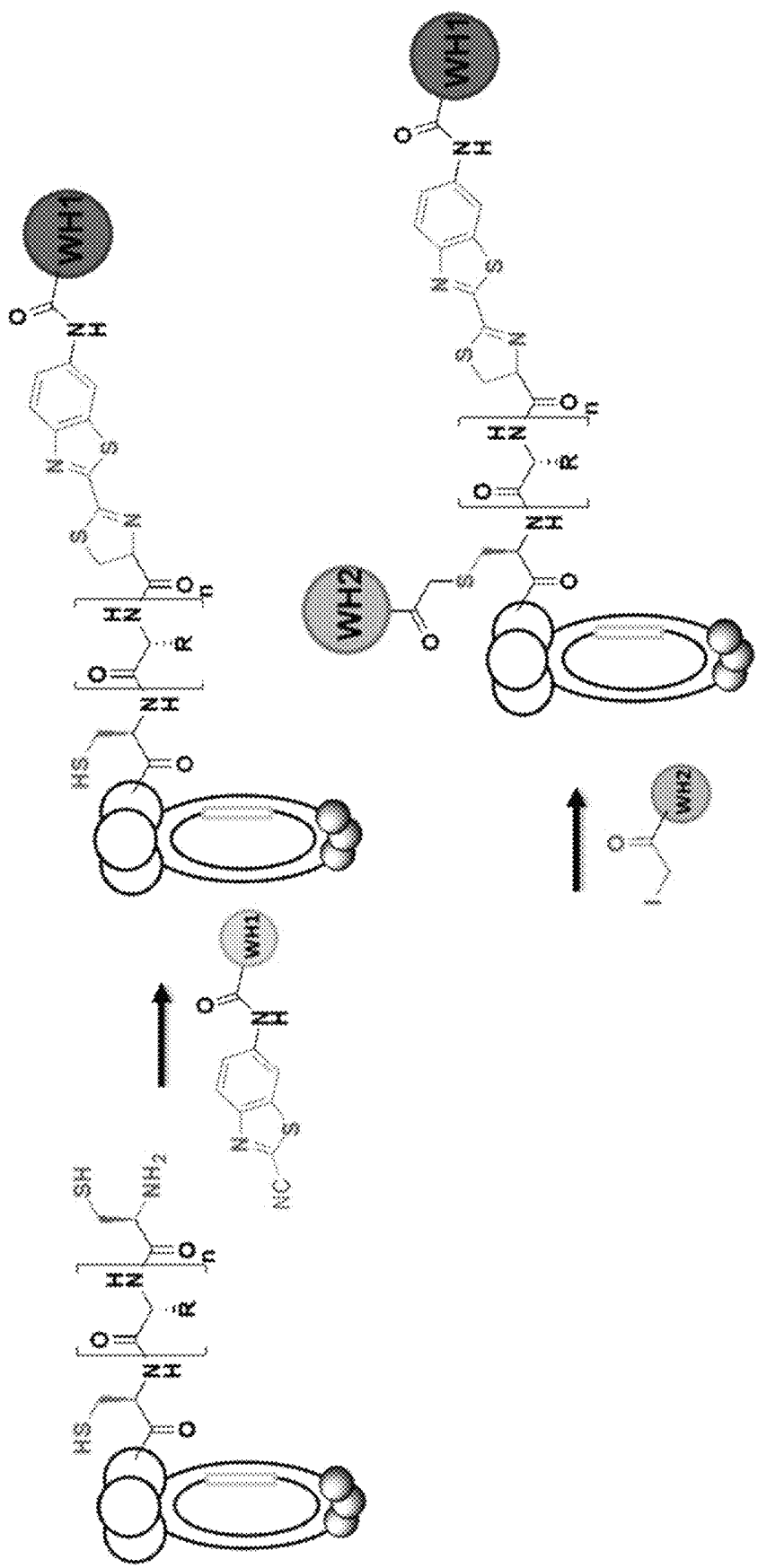
FIG. 1E shows a schematic for the addition of two "warheads" to a phage protein, where the warheads can be the same or different.
Figure 1F:
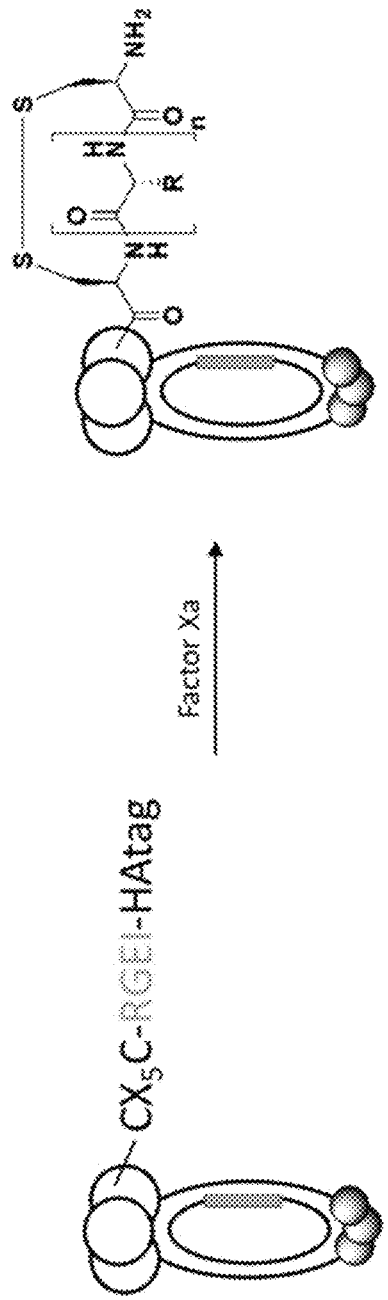
FIG. 1F shows a schematic illustration of a phage library displaying an N-terminal and internal cysteine. A human influenza hemagglutinin (HA) tag-IEGR—C(X)$_5$C peptide library ("IEGR—C(X)$_5$C" disclosed as SEQ ID NO: 83) having an HA tag followed by a Factor Xa cleavage site (IEGR (SEQ ID NO: 79)) was fused on the N-terminus of a phage protein, and a C(X)$_5$C peptide library was incorporated between the Factor Xa cleavage site and the main body of the phage protein. As a result, the N-terminal cysteine could be liberated by Factor Xa cleavage and the Factor Xa cleavage efficiency could be monitored by the removal of the HA tag from the phage.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION OF THE INVENTION

The present disclosure provides low molecular weight molecules able to penetrate cells and tissues and having high specificity and affinity for the surfaces of proteins, methods of making same, pharmaceutical compositions comprising same, and methods of treating cancers, infectious diseases caused by bacteria, fungi, and viruses, and diseases and disorders associated with aberrant protein expression using the same.

The disclosure further provides a method for binding a therapeutic peptide to a protein surface, the method including at least the step of contacting the protein surface with a phage display library comprising phage particles comprising phage display peptides comprising at least one APBA modified cysteine residue. In other embodiments, the disclosure relates to a drug screening method for selection of a therapeutic peptide for binding a protein of interest, the method including at least the following steps: (a) screening a phage display library comprising phage particles comprising phage display peptides comprising at least one APBA modified cysteine residue with the protein of interest; (b) selecting peptide binders with submicromolar affinity against the protein of interest; and (c) conjugating the selected peptide binders with a therapeutic residue targeting the protein of interest. In any of these aspects, the APBA modified cysteine residues bind to surface lysine residues on the protein of interest by dynamic covalent conjugation to form iminoboronates. Also disclosed are therapeutic peptides selected using the disclosed methods, pharmaceutical compositions comprising the disclosed therapeutic peptides, methods of treating diseases using the therapeutic peptides, and methods for medical imaging using the therapeutic peptides.

Many modifications and other embodiments disclosed herein will come to mind to one skilled in the art to which the disclosed compositions and methods pertain having the benefit of the teachings presented in the foregoing descriptions and the associated drawings. Therefore, it is to be understood that the disclosures are not to be limited to the specific embodiments disclosed and that modifications and other embodiments are intended to be included within the scope of the appended claims. The skilled artisan will recognize many variants and adaptations of the aspects described herein. These variants and adaptations are intended to be included in the teachings of this disclosure and to be encompassed by the claims herein.

Although specific terms are employed herein, they are used in a generic and descriptive sense only and not for purposes of limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

Any recited method can be carried out in the order of events recited or in any other order that is logically possible. That is, unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

While aspects of the present disclosure can be described and claimed in a particular statutory class, such as the system statutory class, this is for convenience only and one of skill in the art will understand that each aspect of the present disclosure can be described and claimed in any statutory class.

It is also to be understood that the terminology used herein is for the purpose of describing particular aspects only and is not intended to be limiting. Unless defined otherwise, all technical and scientific terms used herein have the same meaning as commonly understood by one of ordinary skill in the art to which the disclosed compositions and methods belong. It will be further understood that terms, such as those defined in commonly used dictionaries, should be interpreted as having a meaning that is consistent with their meaning in the context of the specification and relevant art and should not be interpreted in an idealized or overly formal sense unless expressly defined herein.

Prior to describing the various aspects of the present disclosure, the following definitions are provided and should be used unless otherwise indicated. Additional terms may be defined elsewhere in the present disclosure.

Definitions

As used herein, "comprising" is to be interpreted as specifying the presence of the stated features, integers, steps, or components as referred to, but does not preclude the presence or addition of one or more features, integers, steps, or components, or groups thereof. Moreover, each of the terms "by", "comprising," "comprises", "comprised of," "including," "includes," "included," "involving," "involves," "involved," and "such as" are used in their open, non-limiting sense and may be used interchangeably. Further, the term "comprising" is intended to include examples and aspects encompassed by the terms "consisting essentially of" and "consisting of." Similarly, the term "consisting essentially of" is intended to include examples encompassed by the term "consisting of."

As used in the specification and the appended claims, the singular forms "a," "an" and "the" include plural referents unless the context clearly dictates otherwise. Thus, for example, reference to "a peptide," "a cell," or "an amino acid," includes, but is not limited to, two or more such peptides, amino acids, or cells, and the like.

It should be noted that ratios, concentrations, amounts, and other numerical data can be expressed herein in a range format. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it will be understood that the particular value forms a further aspect. For example, if the value "about 10" is disclosed, then "10" is also disclosed.

When a range is expressed, a further aspect includes from the one particular value and/or to the other particular value. For example, where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In addition, the phrase "about 'x' to 'y'", where 'x' and 'y' are numerical values, includes "about 'x' to about 'y'".

It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to 5%" should be interpreted to include not only the explicitly recited values of about 0.1% to about 5%, but also include individual values (e.g., about 1%, about 2%, about 3%, and about 4%) and the sub-ranges (e.g., about 0.5% to about 1.1%; about 5% to about 2.4%; about 0.5% to about 3.2%, and about 0.5% to about 4.4%, and other possible sub-ranges) within the indicated range.

As used herein, the terms "about," "approximate," "at or about," and "substantially" mean that the amount or value in question can be the exact value or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In such cases, it is generally understood, as used herein, that "about" and "at or about" mean the nominal value indicated ±10% variation unless otherwise indicated or inferred. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

As used herein, the terms "optional" or "optionally" means that the subsequently described event or circumstance can or cannot occur, and that the description includes instances where said event or circumstance occurs and instances where it does not.

As used herein, the terms "reversible covalent binding motif," "reversible covalent binding warhead," and "reversible covalent binding motif and/or warheads" can be used interchangeably and refer to a peptide comprising a two cysteine moieties, wherein each cysteine moiety is covalently linked to an APBA moiety such that the peptide can bind to a target molecule or peptide or protein surface, e.g., a mutated, misfolded, aberrantly expressed, or pathogen-derived or related protein, through a combination of noncovalent interactions involving the peptide backbone and amino acid side-chains and reversible covalent interactions comprising a reversible covalent linkage between one or both of the APBA moieties and a moiety, e.g., an amine group, in the target molecule or target peptide or protein surface. A peptide comprising a reversible covalent binding motif can be within a peptide that is in a phage display library or an isolated peptide, e.g., a therapeutic APBA peptide as discussed herein below.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms. The term alkyl group can also be a 01 alkyl, C1-C2 alkyl, C1-C3 alkyl, C1-C4 alkyl, C1-CS alkyl, C1-C6 alkyl, C1-C7 alkyl, C1-C8 alkyl, C1-C9 alkyl, C1-C10 alkyl, and the like up to and including a C1-C24 alkyl.

As used herein, the term "APBA," "APBA residue," and "APBA moiety" can be used interchangeably herein and refer to a chemical residue comprising an APBA structure given by the following formula:

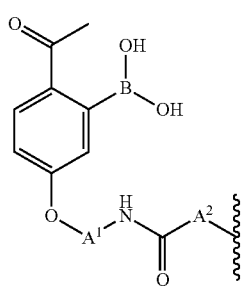

wherein each of $A^1$ and $A^2$ are independently a C1-C6 alkyl. A particular example of an APBA residue is a structure given by the following formula:

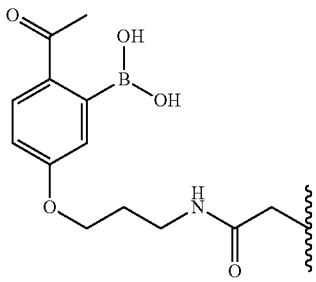 [SMILES: *CC(=O)NCCCOc1ccc(C(C)=O)c(B(O)O)c1]

As used herein, the term "APBA-IA" refers to a compound comprising an APBA residue and an iodoacetamide residue having a structure given by the following formula:

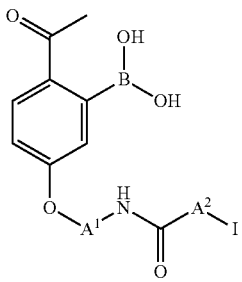

wherein each of $A^1$ and $A^2$ are independently a C1-C6 alkyl. A particular example of APBA-IA is (2-acetyl-5-(3-(2-iodoacetamido)propoxy)phenyl)boronic acid, that is, a compound having a structure given by the following formula:

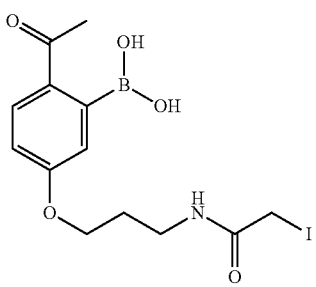 [SMILES: CC(=O)c1ccc(OCCCNC(=O)CI)cc1B(O)O]

The expression "amino acid" as used herein is meant to include both natural and synthetic amino acids, and both D and L amino acids. "Standard amino acid" means any of the twenty standard L-amino acids commonly found in naturally occurring peptides. "Nonstandard amino acid residue" means any amino acid, other than the standard amino acids, regardless of whether it is prepared synthetically or derived from a natural source. As used herein, "synthetic amino acid" also encompasses chemically modified amino acids, including but not limited to salts, amino acid derivatives (such as amides), and substitutions. Amino acids contained within the peptides of the present disclosure, and particularly at the carboxy- or amino-terminus, can be modified by methylation, amidation, acetylation or substitution with other chemical groups which can change the peptide's circulating half-life without adversely affecting their activity. Additionally, a disulfide linkage may be present or absent in the peptides of the invention.

As used herein, the term "APBA modifiable dimer phage library" refers to a phage display library comprising peptides expressed on the surface of the phage display library comprising two cysteine residues that can be chemically modified with an APBA moiety.

As used herein, the term "APBA dimer phage library" refers to a phage display library comprising peptides expressed on the surface of the phage display library comprising two APBA modified cysteine residues.

As used herein, a "therapeutic APBA peptide" is a peptide comprising a peptide sequence as disclosed herein such that the peptide comprises two APBA modified cysteine residues.

As used herein, the term "APBA modified cysteine residue" refers to a cysteine residue comprising an APBA moiety. That is, an APBA modified cysteine residue has a structure given by the formula:

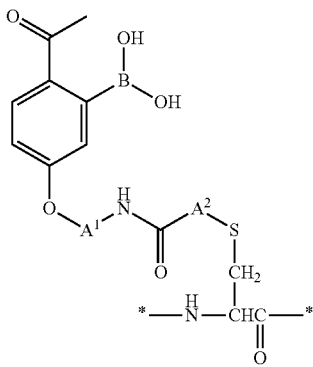

wherein each of $A^1$ and $A^2$ are independently a C1-C6 alkyl. A particular example of an APBA modified cysteine residue can is a structure given by the formula:

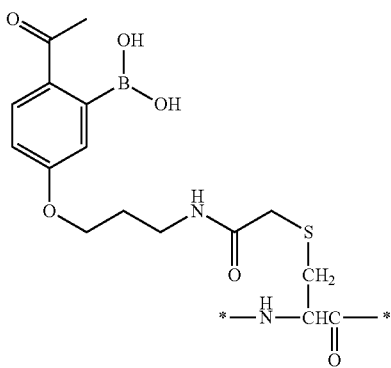

As used herein, the term "APBA modified peptide" is a peptide comprising an APBA modified cysteine residue.

The term "amino acid" is used interchangeably with "amino acid residue," and may refer to a free amino acid and to an amino acid residue of a peptide. It will be apparent from the context in which the term is used whether it refers to a free amino acid or a residue of a peptide.

Amino acids have the following general structure:

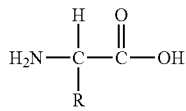

wherein R is a "side chain" or "side group" of the amino acid. Amino acids may be classified into seven groups on the basis of the side chain R: (1) aliphatic side chains, (2) side chains containing a hydroxyl (OH) group, (3) side chains containing sulfur atoms, (4) side chains containing an acidic or amide group, (5) side chains containing a basic group, (6) side chains containing an aromatic ring, and (7) proline, an imino acid in which the side chain is fused to the amino group.

The nomenclature used to describe the peptides or peptide compounds of the present disclosure follows the conventional practice wherein the amino residue is presented to the left and the carboxy group to the right of each amino acid residue. For example, a peptide sequence comprising a sequence of amino acid residues from the amino terminus to the carboxy terminus an alanine residue, an aspartic acid residue, a cysteine residue, and a glycine residue can be specified using the one-letter amino acid code as follows:

ADCG (SEQ ID NO: 80)

In the formula representing selected specific aspects of the present disclosure, e.g., a peptide sequence, the amino- and carboxy-terminal groups, although not specifically shown, will be understood to be in the form they would assume at physiologic pH values, unless otherwise specified. Subscripts in a peptide sequence can be used to indicate a repetition of amino acid, and a subscript range can be used to indicate that the indicated amino acid can be repeated for any of the number of instances of an integer specified by the range, inclusive of the upper and lower limits. For example, a peptide sequence given by:

ADC(G)$_3$ (SEQ ID NO: 81)

would indicate, from the amino terminus to carboxy terminus, a peptide having an alanine residue, an aspartic acid residue, a cysteine residue, and three sequential iterations of a glycine residue. A peptide sequence can also be specified with variable positions using Xxx (three-letter code) or X (one-letter). For example, a peptide sequence comprising a sequence of amino acid residues from the amino terminus to the carboxy terminus an alanine residue, an aspartic acid residue, one to five amino acids selected from the standard amino acids, a cysteine residue, and a glycine residue can be specified using the one-letter amino acid code as follows:

ADC(X)$_{1-5}$G (SEQ ID NO: 82)

As used herein, an "analog" of a chemical compound is a compound that, by way of example, resembles another in structure but is not necessarily an isomer (e.g., 5-fluorouracil is an analog of thymine).

As used herein, an amino acid can be represented by the full name thereof, by the three letter code corresponding thereto, or by the one-letter code corresponding thereto. The full name, three-letter code, and one-letter code for 20 standard amino acids are as indicated in the table below.

| Full Name | Three-Letter Code | One-Letter Code | Side Chain (R) |
|---|---|---|---|
| Aspartic Acid | Asp | D | —CH$_2$—C(=O)—OH |
| Glutamic Acid | Glu | E | —CH$_2$—CH$_2$—C(=O)—OH |
| Lysine | Lys | K | —CH$_2$—CH$_2$—CH$_2$—CH$_2$—NH$_2$ |
| Arginine | Arg | R | —CH$_2$—CH$_2$—CH$_2$—NH—C(=NH)—NH$_2$ |
| Histidine | His | H | —CH$_2$-(imidazole) |
| Tyrosine | Tyr | Y | —CH$_2$-(4-hydroxyphenyl) |
| Cysteine | Cys | C | —CH$_2$—SH |
| Asparagine | Asn | N | —CH$_2$—C(=O)—NH$_2$ |

-continued
| Full Name | Three-Letter Code | One-Letter Code | Side Chain (R) |
|---|---|---|---|
| Glutamine | Gln | Q | 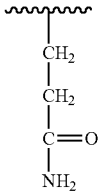 |
| Serine | Ser | S | 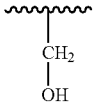 |
| Threonine | Thr | T | 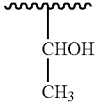 |
| Glycine | Gly | G |  |
| Alanine | Ala | A |  |
| Valine | Val | V | 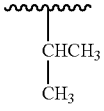 |
| Leucine | Leu | L | 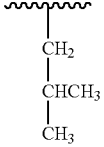 |
| Isoleucine | Ile | I | 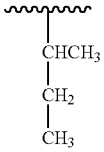 |
| Methionine | Met | M | 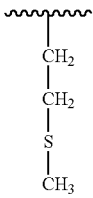 |
| Proline | Pro | P | 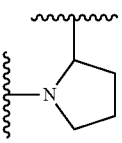 |
| Phenyl-alanine | Phe | F | 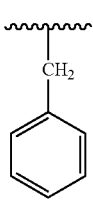 |

| Full Name | Three-Letter Code | One-Letter Code | Side Chain (R) |
|---|---|---|---|
| Tryptophan | Trp | W | 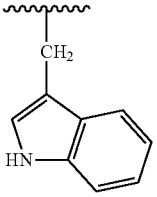 [SMILES: *Cc1c[nH]c2ccccc12] |

The term "basic" or "positively charged" amino acid as used herein, refers to amino acids in which the R groups have a net positive charge at pH 7.0, and include, but are not limited to, the standard amino acids lysine, arginine, and histidine.

A "compound," as used herein, refers to a polypeptide, an isolated nucleic acid, or other agent used in the method of the present disclosure.

As used herein, the terms "polypeptide", "peptide", or "protein" refer to a series of amino acid residues connected one to the other by peptide bonds between the alpha-amino and carboxy groups of adjacent residues. The amino acid residues are preferably in the natural "L" isomeric form. However, residues in the "D" isomeric form can be substituted for any L-amino acid residue, as long as the desired functional property is retained by the polypeptide. In addition, the amino acids, in addition to the 20 standard amino acids, include modified and unusual amino acids. Furthermore, it should be noted that a dash at the beginning or end of an amino acid residue sequence indicates either a peptide bond to a further sequence of one or more amino acid residues or a covalent bond to a carboxyl or hydroxyl end group.

As used herein, the term "APBA modified peptide" refers to a peptide comprising two cysteine residue comprising an APBA moiety having the structure and sequences as disclosed herein.

As used herein, the term "target protein" refers to a peptide or protein that is to be specifically bound by a member of a phage display library of the present disclosure. Target proteins can include specific protein surfaces for which a binding peptide is sought. The target protein is typically characterized by the surface presentation of one or more target lysine or other amino acid residues that are characteristic of the protein type, i.e., characteristic of the target protein in that it is uniquely expressed on the surface of the target protein compared to a nontarget protein. Thus, for example, a target protein can be a protein, such as streptavidin, which presents one or more lysine residues at the surface, that can be bound by a phage display library. In one aspect, the methods disclosed herein can further be modified to bind to protein and peptide surfaces not including surface lysine residues.

As used herein, "phage display" refers to a method of using phage to heterologously express coat proteins or peptides for testing, e.g., particularly newly generated peptides (e.g., from about 5 to about 10 amino acids in length) thereof. A gene encoding a protein or peptide is cloned and inserted into a phage genome or genetic material in such a way that the protein or peptide is displayed (i.e., expressed) on the surf ace of the phage, which is a recombinant phage. Phage expressing peptides that interact with a target molecule or cell can be selected by selecting the protein or peptide directly using panning or affinity chromatography. The non-bound phages can be removed by washing the cells expressing the target molecule. The bound proteins or peptides produced by phages can then be isolated from the target molecule or target peptide or protein surface to which they are bound, and since they are still part of the phage, they can be grown in enough quantity to identify the gene sequence, and hence the protein sequence. This allows further manipulation of phages that bind to the target molecule(s).

As used herein, the term "phage display library" refers to a collection of phage (e.g., filamentous phage) comprising collection of random sequences of nucleic acids that have been inserted into a phage vector, wherein the phage express a heterologous peptide encoded by the random sequences of nucleic acids therein on the surface of a phage particle. The library can contain a few or a large number of random combinations of nucleic acid sequences, varying from about ten to several billion combinations of nucleotide sequences or more that code for a vast number ($\sim 10^{12}$) of random peptides. The external peptide is free to interact with (bind to) other moieties with which the phage are contacted. Each phage displaying an external protein is a "member" of the phage display library. If desired, a molecule or a phage vector can be linked to a tag, which can facilitate recovery or identification of the molecule. In some instances, the heterologously expressed proteins or peptides that are on the surface of a phage particle can be chemically modified to expand the chemical space encompassed by the phage display library, e.g., such a chemically modified phage display library is the disclosed APBA dimer phage library.

As used herein, the term "phage" refers to a bacteriophage or virus that infects bacteria and is capable of displaying a heterologous polypeptide or peptide on its surface. Briefly, a phage comprises a protein coat or capsid enclosing the phage genome or genetic material (DNA or RNA) which is injected into a bacteria upon infection of the bacteria by the phage. The injected genetic material directs the bacteria to synthesize the phage's genetic material and proteins encoded by the phage genetic material using the host bacteria's transcriptional and translational apparatus. These phage components then self-assemble to form new phage viruses or particles. Although one skilled in the art will appreciate that a variety of phage types may be employed in the present invention, in some instances the phage vector is, or is derived from, a filamentous bacteriophage, such as, for example, f1, fd, Pf1, M13, etc. The phage may contain a selectable marker such as tetracycline (e.g., "fd-tet"). Various filamentous phage display systems are well known to those of skill in the art (see, e.g., Zacher et al. (1980) *Gene* 9: 127-140, Smith et al. (1985) *Science* 228: 1315-1317 (1985); and Parmley and Smith (1988) *Gene* 73: 305-318).

As used herein, the term "phage vector" is a bacterial virus which can receive the insertion of a gene or other genetic material, resulting in a recombinant DNA molecule. The phage vector is capable of self-replication in a host organism. A phage vector contains an origin of replication for a bacteriophage but not for a plasmid.

As used herein, the term "viral packaging signal" refers a nucleic acid sequence necessary and sufficient to direct incorporation of a nucleic acid into a viral capsid.

As used herein, the term "assembly cell" refers to a cell in which a nucleic acid can be packaged into a viral coat protein (capsid). Assembly cells may be infected with one or more different virus particles (e.g., a normal or debilitated phage and a helper phage) that individually or in combination direct packaging of a nucleic acid into a viral capsid.

As used herein, the term "detectable label" refers to any material having a detectable physical or chemical property. Such detectable labels have been well-developed in the field of immunoassays and, in general, any label useful in such methods can be applied to the present invention. Thus, a label is any composition detectable by spectroscopic, photochemical, biochemical, immunochemical, electrical, optical or chemical means. Useful labels in the present invention include magnetic beads (e.g. Dynabeads™), fluorescent dyes (e.g., fluorescein isothiocyanate, Texas red, rhodamine, and the like), radiolabels (e.g., 3H, $^{125}$I, $^{35}$S, $^{14}$O, or $^{32}$P), enzymes (e.g., LacZ, CAT, horseradish peroxidase, alkaline phosphatase, and others, commonly used as detectable enzymes, either as marker gene products or in an ELISA), and calorimetric labels such as colloidal gold or colored glass or plastic (e.g. polystyrene, polypropylene, latex, etc.) beads. Those detectable labels that can be expressed by nucleic acids are referred to as "reporter genes" or "reporter gene products".

It will be recognized that fluorescent labels are not to be limited to single species organic molecules, but include inorganic molecules, multi-molecular mixtures of organic and/or inorganic molecules, crystals, heteropolymers, and the like. Thus, for example, CdSe—CdS core-shell nanocrystals enclosed in a silica shell can be easily derivatized for coupling to a biological molecule (Bruchez et al. (1998) *Science*, 281: 2013-2016). Similarly, highly fluorescent quantum dots (zinc sulfide-capped cadmium selenide) have been covalently coupled to biomolecules for use in ultrasensitive biological detection (Warren and Nie (1998) *Science*, 281: 2016-2018).

A residue of a chemical species as herein refers to the moiety that is the resulting product of the chemical species in a particular reaction scheme or subsequent formulation or chemical product, regardless of whether the moiety is actually obtained from the chemical species. In general chemical terms, an example of a residue can be an ethylene glycol residue in a polyester refers to one or more —OCH$_2$CH$_2$O— units in the polyester, regardless of whether ethylene glycol was used to prepare the polyester. Similarly, a sebacic acid residue in a polyester refers to one or more —CO(CH$_2$)$_8$CO— moieties in the polyester, regardless of whether the residue is obtained by reacting sebacic acid or an ester thereof to obtain the polyester. Thus, in particular terms with regard to amino acid residues, it would be understood that an alanine residue in a polypeptide or peptide refers to the presence of a residue having a structure given by the formula:

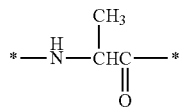

regardless of whether alanine was used to prepare the polypeptide or peptide.

Compounds described herein comprise atoms in both their natural isotopic abundance and in non-natural abundance. The disclosed compounds can be isotopically-labeled or isotopically substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, sulfur, fluorine and chlorine, such as $^2$H, $^3$H, $^{13}$C, $^{14}$C, $^{15}$N, $^{18}$O, $^{17}$O, $^{35}$S, $^{18}$F, and $^{36}$Cl, respectively. Compounds further comprise prodrugs thereof and pharmaceutically acceptable salts of said compounds or of said prodrugs which contain the aforementioned isotopes and/or other isotopes of other atoms are within the scope of this invention. Certain isotopically-labeled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labeled compounds of the present invention and prodrugs thereof can generally be prepared by carrying out the procedures below, by substituting a readily available isotopically labeled reagent for a non-isotopically labeled reagent.

The compounds described in the invention can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvent or water molecules can combine with the compounds according to the invention to form solvates and hydrates. Unless stated to the contrary, the invention includes all such possible solvates.

The term "co-crystal" means a physical association of two or more molecules which owe their stability through non-covalent interaction. One or more components of this molecular complex provide a stable framework in the crystalline lattice. In certain instances, the guest molecules are incorporated in the crystalline lattice as anhydrates or solvates, see e.g. "Crystal Engineering of the Composition of Pharmaceutical Phases. Do Pharmaceutical Co-crystals Represent a New Path to Improved Medicines?" Almarasson, O., et al., *The Royal Society of Chemistry*, 1889-1896, 2004. Examples of co-crystals include p-toluenesulfonic acid and benzenesulfonic acid.

As used herein, "administering" can refer to an administration that is oral, topical, intravenous, subcutaneous, transcutaneous, transdermal, intramuscular, intra-joint, parenteral, intraarterial, intradermal, intraventricular, intraosseous, intraocular, intracranial, intraperitoneal, intralesional, intranasal, intracardiac, intraarticular, intracavernous, intrathecal, intravireal, intracerebral, and intracerebroventricular, intratympanic, intracochlear, rectal, vaginal, by inhalation, by catheters, stents or via an implanted reservoir or other device that administers, either actively or passively (e.g. by diffusion) a composition the perivascular space and adventitia. For example a medical device such as a stent can contain a composition or formulation disposed on its surface, which can then dissolve or be otherwise distributed to the surrounding tissue and cells. The term "parenteral" can include subcutaneous, intravenous, intramuscular, intra-articular, intrasynovial, intrasternal, intrathecal, intrahepatic, intralesional, and intracranial injections or infusion techniques. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

As used herein, "therapeutic agent" can refer to any substance, compound, molecule, and the like, which can be biologically active or otherwise can induce a pharmacologic, immunogenic, biologic and/or physiologic effect on a subject to which it is administered to by local and/or systemic action. A therapeutic agent can be a primary active agent, or in other words, the component(s) of a composition to which the whole or part of the effect of the composition is attributed. A therapeutic agent can be a secondary therapeutic agent, or in other words, the component(s) of a composition to which an additional part and/or other effect of the composition is attributed. The term therefore encompasses those compounds or chemicals traditionally regarded as drugs, vaccines, and biopharmaceuticals including molecules such as proteins, peptides, hormones, nucleic acids, gene constructs and the like. Examples of therapeutic agents are described in well-known literature references such as the Merck Index (14$^{th}$ edition), the *Physicians' Desk Reference* (64$^{th}$ edition), and The Pharmacological Basis of Therapeutics (12$^{th}$ edition), and they include, without limitation, medicaments; vitamins; mineral supplements; substances used for the treatment, prevention, diagnosis, cure or mitigation of a disease or illness; substances that affect the structure or function of the body, or pro-drugs, which become biologically active or more active after they have been placed in a physiological environment. For example, the term "therapeutic agent" includes compounds or compositions for use in all of the major therapeutic areas including, but not limited to, adjuvants; anti-infectives such as antibiotics and antiviral agents; analgesics and analgesic combinations, anorexics, anti-inflammatory agents, anti-epileptics, local and general anesthetics, hypnotics, sedatives, antipsychotic agents, neuroleptic agents, antidepressants, anxiolytics, antagonists, neuron blocking agents, anticholinergic and cholinomimetic agents, antimuscarinic and muscarinic agents, antiadrenergics, nutrients, antiarthritics, antiasthmatic agents, anticonvulsants, antihistamines, antinauseants, antineoplastics, antipruritics, antipyretics; antispasmodics, cardiovascular preparations (including calcium channel blockers, beta-blockers, beta-agonists and antiarrythmics), antihypertensives, diuretics, vasodilators; central nervous system stimulants; cough and cold preparations; decongestants; diagnostics; hormones; bone growth stimulants and bone resorption inhibitors; immunosuppressives; muscle relaxants; psychostimulants; sedatives; tranquilizers; proteins, peptides, and fragments thereof (whether naturally occurring, chemically synthesized or recombinantly produced); and nucleic acid molecules (polymeric forms of two or more nucleotides, either ribonucleotides (RNA) or deoxyribonucleotides (DNA) including both double- and single-stranded molecules, gene constructs, expression vectors, antisense molecules and the like), small molecules (e.g., doxorubicin) and other biologically active macromolecules such as, for example, proteins and enzymes. The agent may be a biologically active agent used in medical, including veterinary, applications and in agriculture, such as with plants, as well as other areas. The term therapeutic agent also includes without limitation, medicaments; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment.

As used herein, "kit" means a collection of at least two components constituting the kit. Together, the components constitute a functional unit for a given purpose. Individual member components may be physically packaged together or separately. For example, a kit comprising an instruction for using the kit may or may not physically include the instruction with other individual member components. Instead, the instruction can be supplied as a separate member component, either in a paper form or an electronic form which may be supplied on computer readable memory device or downloaded from an internet website, or as recorded presentation.

As used herein, "instruction(s)" means documents describing relevant materials or methodologies pertaining to a kit. These materials may include any combination of the following: background information, list of components and their availability information (purchase information, etc.), brief or detailed protocols for using the kit, trouble-shooting, references, technical support, and any other related documents. Instructions can be supplied with the kit or as a separate member component, either as a paper form or an electronic form which may be supplied on computer readable memory device or downloaded from an internet website, or as recorded presentation. Instructions can comprise one or multiple documents, and are meant to include future updates.

As used herein, "attached" can refer to covalent or non-covalent interaction between two or more molecules. Non-covalent interactions can include ionic bonds, electrostatic interactions, van der Waals forces, dipole-dipole interactions, dipole-induced-dipole interactions, London dispersion forces, hydrogen bonding, halogen bonding, electromagnetic interactions, Π-Π interactions, cation-Π interactions, anion-Π interactions, polar Π-interactions, and hydrophobic effects.

As used interchangeably herein, "subject," "individual," or "patient" can refer to a vertebrate organism, such as a mammal (e.g. human). "Subject" can also refer to a cell, a population of cells, a tissue, an organ, or an organism, preferably to human and constituents thereof.

As used herein, the terms "treating" and "treatment" can refer generally to obtaining a desired pharmacological and/or physiological effect. The effect can be, but does not necessarily have to be, prophylactic in terms of preventing or partially preventing a disease, symptom or condition thereof, such as a disease or disorder characterized by aberrant protein production or folding (e.g., overexpression of a protein, expression of a protein with a deleterious mutated sequence, protein misfolding resulting in a different tertiary or quaternary structure than wild type, etc.). The effect can be therapeutic in terms of a partial or complete cure of a disease, condition, symptom or adverse effect attributed to the disease, disorder, or condition. The term "treatment" as used herein can include any treatment of a disease associated with aberrant protein production in a subject, particularly a human and can include any one or more of the following: (a) preventing the disease from occurring in a subject which may be predisposed to the disease but has not yet been diagnosed as having it; (b) inhibiting the disease, i.e., arresting its development; and (c) relieving the disease, i.e., mitigating or ameliorating the disease and/or its symptoms or conditions. The term "treatment" as used herein can refer to both therapeutic treatment alone, prophylactic treatment alone, or both therapeutic and prophylactic treatment. Those in need of treatment (subjects in need thereof) can include those already with the disorder and/or those in which the disorder is to be prevented. As used herein, the term "treating", can include inhibiting the disease, disorder or condition, e.g., impeding its progress; and relieving the disease, disorder, or condition, e.g., causing regression of the disease, disorder and/or condition. Treating the disease, disorder, or condition can include ameliorating at least one symptom of the particular disease, disorder, or condition, even if the underlying pathophysiology is not affected, e.g., such as treating the pain of a subject by administration of an analgesic agent even though such agent does not treat the cause of the pain.

As used herein, "dose," "unit dose," or "dosage" can refer to physically discrete units suitable for use in a subject, each unit containing a predetermined quantity of a disclosed compound and/or a pharmaceutical composition thereof calculated to produce the desired response or responses in association with its administration.

As used herein, "therapeutic" can refer to treating, healing, and/or ameliorating a disease, disorder, condition, or side effect, or to decreasing in the rate of advancement of a disease, disorder, condition, or side effect.

As used herein, "effective amount" can refer to the amount of a disclosed compound or pharmaceutical composition provided herein that is sufficient to effect beneficial or desired biological, emotional, medical, or clinical response of a cell, tissue, system, animal, or human. An effective amount can be administered in one or more administrations, applications, or dosages. The term can also include within its scope amounts effective to enhance or restore to substantially normal physiological function.

As used herein, the term "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors within the knowledge and expertise of the health practitioner and which may be well known in the medical arts. In the case of treating a particular disease or condition, in some instances, the desired response can be inhibiting the progression of the disease or condition. This may involve only slowing the progression of the disease temporarily. However, in other instances, it may be desirable to halt the progression of the disease permanently. This can be monitored by routine diagnostic methods known to one of ordinary skill in the art for any particular disease. The desired response to treatment of the disease or condition also can be delaying the onset or even preventing the onset of the disease or condition.

For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. It is generally preferred that a maximum dose of the pharmacological agents of the invention (alone or in combination with other therapeutic agents) be used, that is, the highest safe dose according to sound medical judgment. It will be understood by those of ordinary skill in the art however, that a patient may insist upon a lower dose or tolerable dose for medical reasons, psychological reasons or for virtually any other reasons.

A response to a therapeutically effective dose of a disclosed compound and/or pharmaceutical composition, for example, can be measured by determining the physiological effects of the treatment or medication, such as the decrease or lack of disease symptoms following administration of the treatment or pharmacological agent. Other assays will be known to one of ordinary skill in the art and can be employed for measuring the level of the response. The amount of a treatment may be varied for example by increasing or decreasing the amount of a disclosed compound and/or pharmaceutical composition, by changing the disclosed compound and/or pharmaceutical composition administered, by changing the route of administration, by changing the dosage timing and so on. Dosage can vary, and can be administered in one or more dose administrations daily, for one or several days. Guidance can be found in the literature for appropriate dosages for given classes of pharmaceutical products.

As used herein, the term "prophylactically effective amount" refers to an amount effective for preventing onset or initiation of a disease or condition.

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

The term "pharmaceutically acceptable" describes a material that is not biologically or otherwise undesirable, i.e., without causing an unacceptable level of undesirable biological effects or interacting in a deleterious manner.

The term "pharmaceutically acceptable salts", as used herein, means salts of the active principal agents which are prepared with acids or bases that are tolerated by a biological system or tolerated by a subject or tolerated by a biological system and tolerated by a subject when administered in a therapeutically effective amount. When compounds of the present disclosure contain relatively acidic functionalities, base addition salts can be obtained by contacting the neutral form of such compounds with a sufficient amount of the desired base, either neat or in a suitable inert solvent.

Examples of pharmaceutically acceptable base addition salts include, but are not limited to; sodium, potassium, calcium, ammonium, organic amino, magnesium salt, lithium salt, strontium salt or a similar salt. When compounds of the present disclosure contain relatively basic functionalities, acid addition salts can be obtained by contacting the neutral form of such compounds with a sufficient amount of the desired acid, either neat or in a suitable inert solvent.

Examples of pharmaceutically acceptable acid addition salts include, but are not limited to; those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like.

The term "pharmaceutically acceptable ester" refers to esters of compounds of the present disclosure which hydrolyze in vivo and include those that break down readily in the human body to leave the parent compound or a salt thereof. Examples of pharmaceutically acceptable, non-toxic esters of the present disclosure include C1-to-C6 alkyl esters and C5-to-C7 cycloalkyl esters, although C1-to-C4 alkyl esters are preferred. Esters of disclosed compounds can be prepared according to conventional methods. Pharmaceutically acceptable esters can be appended onto hydroxy groups by reaction of the compound that contains the hydroxy group with acid and an alkylcarboxylic acid such as acetic acid, or with acid and an arylcarboxylic acid such as benzoic acid. In the case of compounds containing carboxylic acid groups, the pharmaceutically acceptable esters are prepared from compounds containing the carboxylic acid groups by reaction of the compound with base such as triethylamine and an alkyl halide, for example with methyl iodide, benzyl iodide, cyclopentyl iodide or alkyl triflate. They also can be prepared by reaction of the compound with an acid such as hydrochloric acid and an alcohol such as ethanol or methanol.

The term "pharmaceutically acceptable amide" refers to non-toxic amides of the present disclosure derived from ammonia, primary C1-to-C6 alkyl amines and secondary C1-to-C6 dialkyl amines. In the case of secondary amines, the amine can also be in the form of a 5- or 6-membered heterocycle containing one nitrogen atom. Amides derived from ammonia, C1-to-C3 alkyl primary amides and C1-to-C2 dialkyl secondary amides are preferred. Amides of disclosed compounds can be prepared according to conventional methods. Pharmaceutically acceptable amides can be prepared from compounds containing primary or secondary amine groups by reaction of the compound that contains the amino group with an alkyl anhydride, aryl anhydride, acyl halide, or amyl halide. In the case of compounds containing carboxylic acid groups, the pharmaceutically acceptable amides are prepared from compounds containing the carboxylic acid groups by reaction of the compound with base such as triethylamine, a dehydrating agent such as dicyclohexyl carbodiimide or carbonyl diimidazole, and an alkyl amine, dialkylamine, for example with methylamine, diethylamine, and piperidine. They also can be prepared by reaction of the compound with an acid such as sulfuric acid and an alkylcarboxylic acid such as acetic acid, or with acid and an arylcarboxylic acid such as benzoic acid under dehydrating conditions such as with molecular sieves added. The composition can contain a compound of the present disclosure in the form of a pharmaceutically acceptable prodrug.

The term "pharmaceutically acceptable prodrug" or "prodrug" represents those prodrugs of the compounds of the present disclosure which are, within the scope of sound medical judgment, suitable for use in contact with the tissues of humans and lower animals without undue toxicity, irritation, allergic response, and the like, commensurate with a reasonable benefit/risk ratio, and effective for their intended use. Prodrugs of the present disclosure can be rapidly transformed in vivo to a parent compound having a structure of a disclosed compound, for example, by hydrolysis in blood. A thorough discussion is provided in T. Higuchi and V. Stella, Pro-drugs as Novel Delivery Systems, V. 14 of the A.C.S. Symposium Series, and in Edward B. Roche, ed., *Bioreversible Carriers in Drug Design*, American Pharmaceutical Association and Pergamon Press (1987).

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, and amides, salts of esters or amides, and N-oxides of a parent compound.

The term "contacting" as used herein refers to bringing a disclosed compound or pharmaceutical composition in proximity to a cell, a target protein, or other biological entity together in such a manner that the disclosed compound or pharmaceutical composition can affect the activity of a cell, target protein, or other biological entity, either directly; i.e., by interacting with the cell, target protein, or other biological entity itself, or indirectly; i.e., by interacting with another molecule, co-factor, factor, or protein on which the activity of the cell, target protein, or other biological entity itself is dependent.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, NJ.), Fisher Scientific (Pittsburgh, Pa.), or Sigma (St. Louis, Mo.) or are prepared by methods known to those skilled in the art following procedures set forth in references such as *Fieser and Fieser's Reagents for Organic Synthesis*, Volumes 1-17 (John Wiley and Sons, 1991); *Rodd's Chemistry of Carbon Compounds*, Volumes 1-5 and *Supplementals* (Elsevier Science Publishers, 1989); *Organic Reactions*, Volumes 1-40 (John Wiley and Sons, 1991); *March's Advanced Organic Chemistry*, (John Wiley and Sons, 4$^{th}$ Edition); and *Larock's Comprehensive Organic Transformations* (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible nonexpress basis for interpretation, including: matters of logic with respect to arrangement of steps or operational flow; plain meaning derived from grammatical organization or punctuation; and the number or type of embodiments described in the specification.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

As used herein, nomenclature for compounds, including organic compounds, can be given using common names, IUPAC, IUBMB, or CAS recommendations for nomenclature. When one or more stereochemical features are present, Cahn-lngold-Prelog rules for stereochemistry can be employed to designate stereochemical priority, E/Z specification, and the like. One of skill in the art can readily ascertain the structure of a compound if given a name, either by systemic reduction of the compound structure using naming conventions, or by commercially available software, such as CHEMDRAW™ (Cambridgesoft Corporation, U.S.A.).

It is understood, that unless otherwise specified, temperatures referred to herein are based on atmospheric pressure (i.e. one atmosphere).

Chemically Modified Phage Libraries

Screening of the APBA dimer library herein yielded protein binders of submicromolar potency. The contrasting results highlight the promise of chemically modified phage libraries. Even higher potency binding could be accomplished with better designed phage libraries with reversible covalent warheads.

The phage panning against peptides and proteins is remarkably convenient and powerful, allowing facile incorporation of negative screens and internal competitors. Specifically, as previously reported, abundant endogenous protein could compete for iminoboronate conjugation, thereby inhibiting the protein binding of an APBA-containing peptide. The data presented in the present disclosure unequivocally show that this protein interference problem can be overcome by including serum albumin in the screening mixture and the reversible covalent binding mechanism can afford highly selective binders in complex biological milieu.

The APBA dimer library can be extended to discovering binders of various proteins and peptides associated with pathogens, cancers, and genetic disorders. This is feasible given that iminoboronate chemistry is generally applicable to primary amines, which can be abundant in peptides and proteins, particularly those presenting numerous surface lysine residues.

The present disclosure provides that a protein or peptide surface binder identified from phage display can be readily converted to a targeted antifungal, antiviral, antibiotic, or anticancer agent; to a peptide or protein-inactivating agent; to a contrast agent for imaging; or the like. The facile generation of targeted antibiotics, for example, is of contemporary importance given the undesirable consequences of broad-spectrum antibiotics, which inevitably cultivate antibiotic resistance and cause damage to human microbiota. In another example, targeted anticancer agents can reduce systemic side effects of chemotherapy, and targeted contrast agents would allow for lower doses of potentially toxic compounds to be administered to subjects undergoing magnetic resonance imaging, computed tomography, X-ray, ultrasound, and other scans to detect cancers, monitor the success of medical treatments, and for other reasons.

The phage display platform can be further developed to include additional phage libraries with reversible covalent warheads. This can be accomplished by varying the designs of the reversible covalent warheads and introducing cross-links to the linear peptide architecture to generate cyclic and multicyclic peptides. Additional phage libraries as such can maximize the chance of success for a diverse range of target proteins.

The disclosed phage display libraries comprise an APBA residue. In various aspects, the disclosed phage display libraries comprise two APBA modified cysteine residues in a peptide expressed on a phage particle surface. As discussed herein above, an APBA residue has a structure given by the following formula:

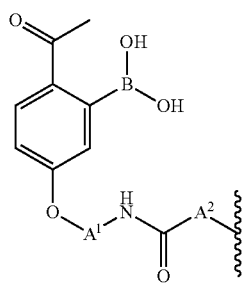

wherein each of $A^1$ and $A^2$ are independently a C1-C6 alkyl. A particular example of an APBA residue is a structure given by the following formula:

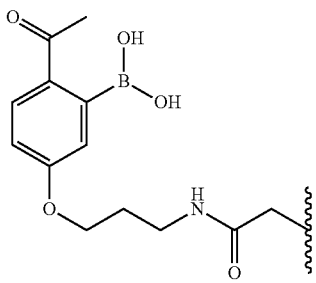 [SMILES: *CC(=O)NCCCOc1ccc(C(C)=O)c(B(O)O)c1]

Accordingly, a disclosed phage display library comprises peptide structures on an external surface of a phage particle comprising two cysteine residues having an APBA residue as shown herein above.

In various aspects, a disclosed phage display library comprises an APBA modified peptide, i.e., peptides expressed on an external surface of a phage particle such that the peptides comprise an APBA modified cysteine residue, as discussed above.

In various aspects, a disclosed phage display library can be prepared by chemically modifying an APBA modifiable phage display library, e.g., using an APBA-IA reagent. Specific examples of preparation of a disclosed phage display library using an APBA-IA are provided herein below in the Examples. As defined above, an APBA-IA reagent is a compound comprising an APBA moiety and an iodoacetamide residue having a structure given by the following formula:

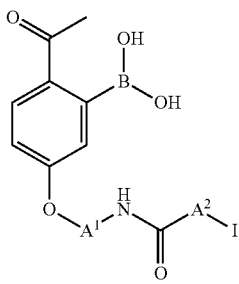

wherein each of $A^1$ and $A^2$ are independently a C1-C6 alkyl. A particular example of APBA-IA is (2-acetyl-5-(3-(2-iodoacetamido)propoxy)phenyl)boronic acid, that is, a compound having a structure given by the following formula:

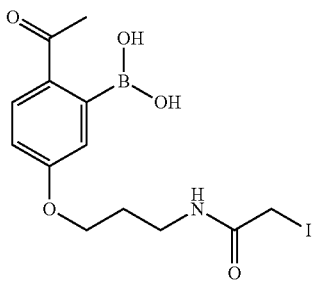 [SMILES: CC(=O)c1ccc(OCCCNC(=O)CI)cc1B(O)O]

In various aspects, a disclosed APBA modifiable dimer phage library is a phage display library comprising a peptide sequence on an external portion of a phage particle as follows:

$XC(X)_nC(X)_m$ wherein each instance of X is an amino acid independently selected from D, E, K, R, H, Y, N, Q, S, T, G, A, V, L, I, M, P, F, and W; wherein n is an integer selected from 5, 6, 7, 8, 9, and 10; and wherein m is an integer selected from 1, 2, 3, 4, and 5. As disclosed herein, a disclosed APBA modifiable dimer phage library comprises APBA modifiable peptides on the surface of a phage particle having the structure given by the following formula:

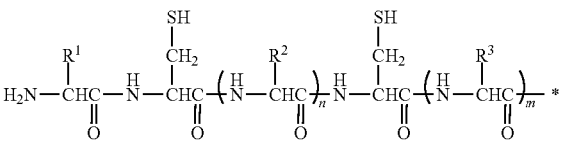

wherein each occurrence of $R^1$, $R^2$, and $R^3$ is independently selected from a moiety that is an amino acid side chain except a cysteine side chain; wherein n is an integer selected from 5, 6, 7, 8, 9, and 10; and wherein m is an integer selected from 1, 2, 3, 4, and 5.

In a particular instance, an APBA modifiable dimer phage library is a phage display library comprising a peptide sequence on an external portion of a phage particle as follows:

$AC(X)_nC(G)_m$  (SEQ ID NO: 84)

In a particular instance, an APBA modifiable dimer phage library comprises APBA modifiable peptides on the surface of a phage particle have the structure given by the following formula:

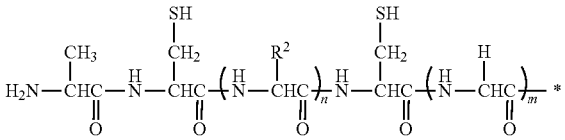

wherein each occurrence of $R^2$ is independently selected from a moiety that is an amino acid side chain except cysteine; wherein n is an integer selected from 5, 6, 7, 8, 9, and 10; and wherein m is an integer selected from 1, 2, 3, 4, and 5.

In various aspects, a disclosed phage display library is an APBA dimer phage library. An exemplary phage display library comprises peptide sequences on an external portion of a phage particle as follows:

$XC^*(X)_nC^*(X)_m$ wherein C* indicates a cysteine residue modified to comprise an APBA residue; wherein each instance of X is an amino acid independently selected from D, E, K, R, H, Y, N, Q, S, T, G, A, V, L, I, M, P, F, and W; wherein n is an integer selected from 5, 6, 7, 8, 9, and 10; wherein m is an integer selected from 1, 2, 3, 4, and 5.

In a further aspect, a disclosed APBA dimer phage library comprises APBA modified peptides on the surface of a phage particle having a structure given by the following formula:

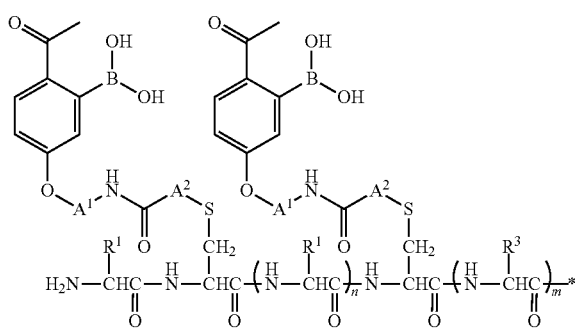

wherein each of $A^1$ and $A^2$ are independently a C1-C6 alkyl; wherein each occurrence of $R^1$, $R^2$, and $R^3$ is independently selected from a moiety that is an amino acid side chain except cysteine; wherein n is an integer selected from 5, 6, 7, 8, 9, and 10; and wherein m is an integer selected from 1, 2, 3, 4, and 5.

In a further aspect, an APBA dimer phage library comprises modified peptides on the surface of a phage particle having a structure given by the following formula:

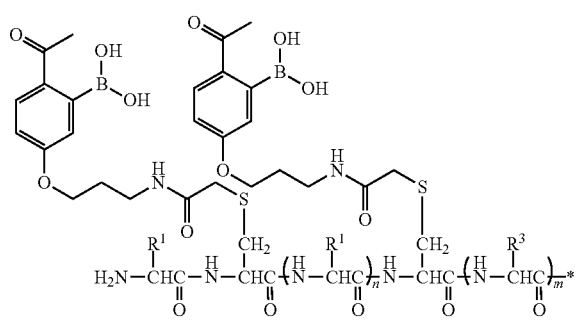

In various aspects, a disclosed APBA dimer phage library is a phage display library comprising peptide sequence on an external portion of a phage particle as follows:

AC*(X)$_n$C*(G)$_m$ (SEQ ID NO: 85)

In various aspects, an APBA dimer phage library comprises APBA modified peptides on the surface of a phage particle having a structure given by the following formula:

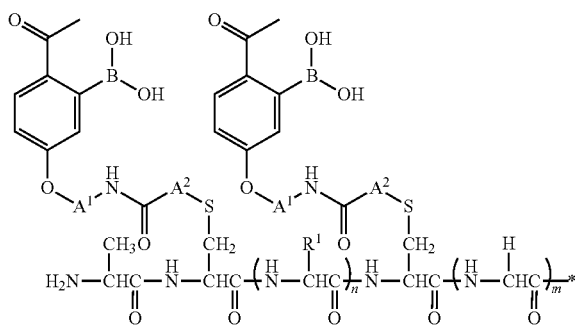

In a further aspect, an APBA dimer phage library comprises APBA modified peptides on the surface of a phage particle having a structure given by the following formula:

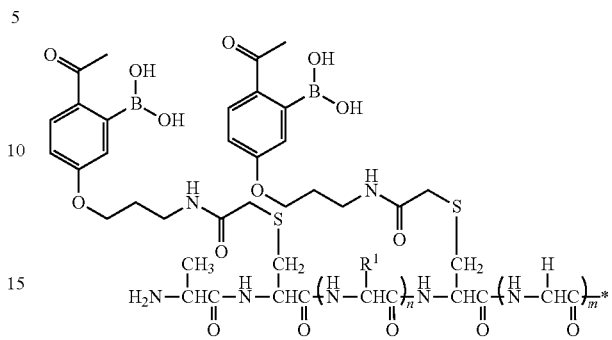

Therapeutic APBA Peptides

In various aspects, the present disclosure pertains to therapeutic APBA peptides. That is, APBA modified peptides which are understood to be peptides comprising two APBA modified cysteine residues. An exemplary disclosed therapeutic APBA peptide is a peptide sequence as follows:

XC*(X)$_n$C*(X)$_m$, wherein C* indicates a cysteine residue modified to comprise an APBA residue; wherein each instance of X is an amino acid independently selected from D, E, K, R, H, Y, N, Q, S, T, G, A, V, L, I, M, P, F, and W; wherein n is an integer selected from 5, 6, 7, 8, 9, and 10; wherein m is an integer selected from 1, 2, 3, 4, and 5.

In various aspects, a disclosed therapeutic APBA peptide is a peptide having a structure given by the formula:

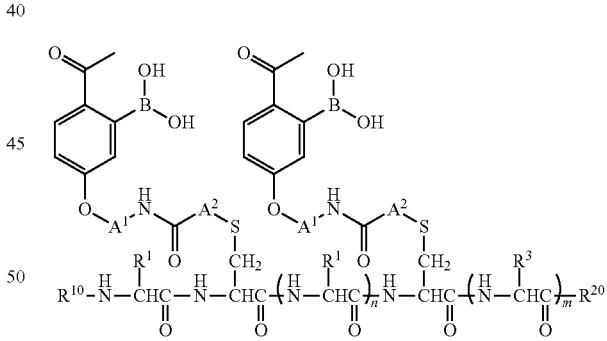

wherein each of $A^1$ and $A^2$ are independently a C1-C6 alkyl; wherein each occurrence of $R^1$, $R^2$, and $R^3$ is independently selected from a side chain of an amino acid selected from D, E, K, R, H, Y, N, Q, S, T, G, A, V, L, I, M, P, F, and W; wherein each of $R^{10}$ and $R^{20}$ is selected from hydrogen, antibiotic residue, an antiviral residue, an antifungal residue, an anticancer residue, an imaging residue, a contrast agent residue, or a combination thereof; wherein n is an integer selected from 5, 6, 7, 8, 9, and 10; and wherein m is an integer selected from 1, 2, 3, 4, and 5.

In a further aspect, a disclosed therapeutic APBA peptide is a peptide having a structure given by the formula:

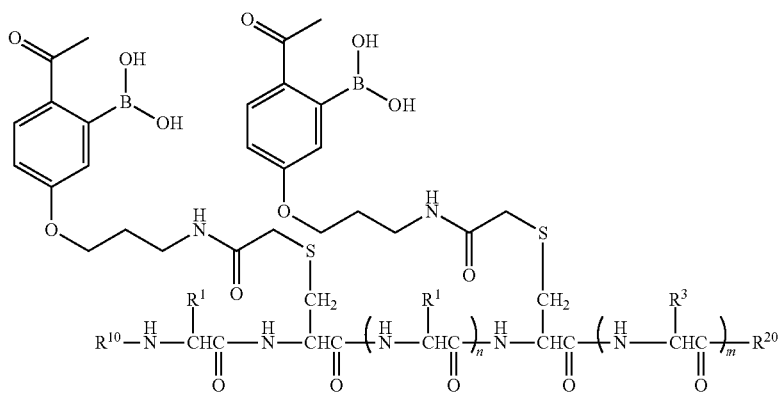

In a further aspect, a disclosed therapeutic APBA peptide is a peptide having a structure given by the formula:

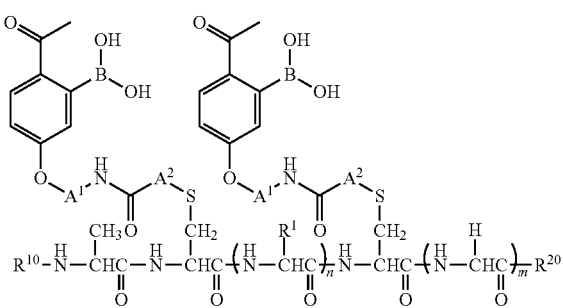

In a further aspect, a disclosed therapeutic APBA peptide is a peptide having a structure given by the formula:

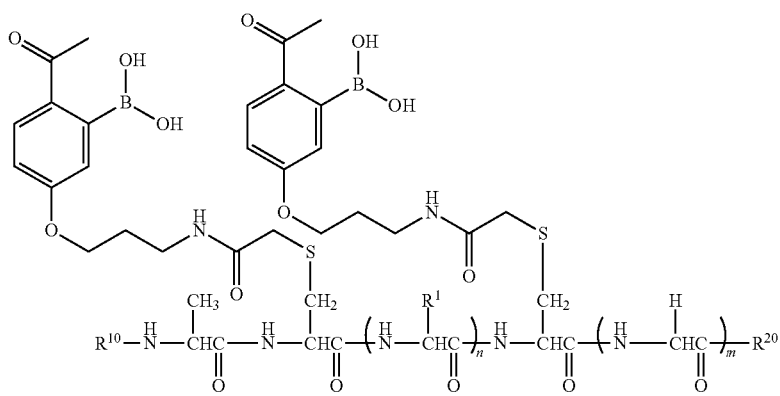

some aspects, the phage display peptides have two APBA modified cysteine residues as disclosed herein.

In another aspect, the protein surface has one or more surface lysine residues. In one aspect, the APBA modified cysteine residues bind to the surface residues by dynamic covalent conjugation to form iminoboronates. In some aspects, the protein surface includes a binding pocket. In other aspects, the protein surface does not include a binding aspect. In aspects wherein the protein surface includes a binding pocket, the therapeutic peptides disclosed herein can bind within the binding pocket or outside of the binding pocket.

Drug Screening Method

In one aspect, disclosed herein is a drug screening method for selection of a therapeutic peptide for binding a protein of interest, the method including at least the following steps:
a. screening a phage display library comprising phage particles comprising phage display peptides comprising at least one APBA modified cysteine residue with the protein of interest;
b. selecting peptide binders with submicromolar affinity against the protein of interest; and
c. conjugating the selected peptide binders with a therapeutic residue targeting the protein of interest.

In some aspects, the protein of interest can be a bacterial protein, a viral protein, a fungal protein, a misfolded protein, an overexpressed protein, a protein expressed by a cancer cell, or a combination thereof. Also disclosed are therapeutic peptides selected by the drug screening method disclosed herein.

Method for Binding a Therapeutic Peptide to a Protein Surface

In one aspect, disclosed herein is a method for binding a therapeutic peptide as disclosed herein to a protein surface, the method including the step of contacting the protein surface with a phage display library that includes phage particles having phage display peptides with at least one APBA modified cysteine residue as disclosed herein. In In another aspect, the therapeutic peptides disclosed herein further include a therapeutic residue at the N-terminus of the therapeutic peptide. In one aspect, the therapeutic residue can be an antibiotic agent, an antiviral agent, an antifungal agent, an anticancer agent, an imaging agent, a contrast agent, or a combination thereof. Exemplary therapeutic agents are disclosed herein. Also disclosed are pharmaceutical compositions including the therapeutic peptides disclosed herein and at least one pharmaceutically acceptable excipient.

Also disclosed is a method for treating a disease or disorder in a subject, the method comprising administering a therapeutically effective amount of the disclosed pharmaceutical compositions to the subject, wherein the therapeutic residue can be an antibiotic agent, an antiviral agent, an antifungal agent, an anticancer agent, or a combination thereof.

In another aspect, disclosed is a method for imaging a protein, cell, tissue, or organ in a subject, the method including the steps of administering the pharmaceutical compositions disclosed herein to the subject and imaging the cell, tissue, protein, or organ, wherein the therapeutic residue is an imaging agent, a contrast agent, or a combination thereof.

Pharmaceutical Compositions

In various aspects, the present disclosure relates to pharmaceutical compositions comprising a therapeutically effective amount of at least one therapeutic APBA peptide, or a pharmaceutically acceptable salt thereof. As used herein, "pharmaceutically-acceptable carriers" means one or more of a pharmaceutically acceptable diluents, preservatives, antioxidants, solubilizers, emulsifiers, coloring agents, releasing agents, coating agents, sweetening, flavoring and perfuming agents, and adjuvants. The disclosed pharmaceutical compositions can be conveniently presented in unit dosage form and prepared by any of the methods well known in the art of pharmacy and pharmaceutical sciences.

In a further aspect, the disclosed pharmaceutical compositions comprise a therapeutically effective amount of at least one disclosed therapeutic APBA peptide, optionally one or more other therapeutic agent, and optionally one or more adjuvant. The disclosed pharmaceutical compositions include those suitable for oral, rectal, topical, pulmonary, nasal, and parenteral administration, although the most suitable route in any given case will depend on the particular host, and nature and severity of the conditions for which the active ingredient is being administered. In a further aspect, the disclosed pharmaceutical composition can be formulated to allow administration orally, nasally, via inhalation, parenterally, paracancerally, transmucosally, transdermally, intramuscularly, intravenously, intradermally, subcutaneously intraperitoneally, intraventricularly, intracranially and intratumorally.

As used herein, "parenteral administration" includes administration by bolus injection or infusion, as well as administration by intravenous, intramuscular, intraarterial, intrathecal, intracapsular, intraorbital, intracardiac, intradermal, intraperitoneal, transtracheal, subcutaneous, subcuticular, intraarticular, subcapsular subarachnoid, intraspinal, epidural and intrasternal injection and infusion.

In various aspects, the present disclosure also relates to a pharmaceutical composition comprising a pharmaceutically acceptable carrier or diluent and, as active ingredient, and at least one disclosed therapeutic APBA peptide. In a further aspect, at least one disclosed therapeutic APBA peptide may be formulated into various pharmaceutical forms for administration purposes.

Pharmaceutically acceptable salts can be prepared from pharmaceutically acceptable nontoxic bases or acids. For therapeutic use, salts of the disclosed therapeutic APBA peptide are those wherein the counter ion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not, are contemplated by the present disclosure. Pharmaceutically acceptable acid and base addition salts are meant to comprise the therapeutically active non-toxic acid and base addition salt forms which the disclosed compounds are able to form.

In various aspects, a disclosed therapeutic APBA peptide comprising an acidic group or moiety, e.g., a carboxylic acid group, can be used to prepare a pharmaceutically acceptable salt. For example, such a disclosed compound may comprise an isolation step comprising treatment with a suitable inorganic or organic base. In some cases, it may be desirable in practice to initially isolate a compound from the reaction mixture as a pharmaceutically unacceptable salt and then simply convert the latter back to the free acid compound by treatment with an acidic reagent, and subsequently convert the free acid to a pharmaceutically acceptable base addition salt. These base addition salts can be readily prepared using conventional techniques, e.g., by treating the corresponding acidic compounds with an aqueous solution containing the desired pharmacologically acceptable cations and then evaporating the resulting solution to dryness, preferably under reduced pressure. Alternatively, they also can be prepared by mixing lower alkanolic solutions of the acidic compounds and the desired alkali metal alkoxide together, and then evaporating the resulting solution to dryness in the same manner as before.

Bases that can be used to prepare the pharmaceutically acceptable base-addition salts of the base compounds are those which can form non-toxic base-addition salts, i.e., salts containing pharmacologically acceptable cations such as, alkali metal cations (e.g., lithium, potassium and sodium), alkaline earth metal cations (e.g., calcium and magnesium), ammonium or other water-soluble amine addition salts such as N-methylglucamine-(meglumine), lower alkanolammonium and other such bases of organic amines. In a further aspect, derived from pharmaceutically acceptable organic non-toxic bases include primary, secondary, and tertiary amines, as well as cyclic amines and substituted amines such as naturally occurring and synthesized substituted amines. In various aspects, such pharmaceutically acceptable organic non-toxic bases include, but are not limited to, ammonia, methylamine, ethylamine, propylamine, isopropylamine, any of the four butylamine isomers, betaine, caffeine, choline, dimethylamine, diethylamine, diethanolamine, dipropylamine, diisopropylamine, di-n-butylamine, N,N'-di benzylethylenediamine, pyrrolidine, piperidine, morpholine, trimethylamine, triethylamine, tripropylamine, tromethamine, 2-diethylaminoethanol, 2-dimethylaminoethanol, ethanolamine, quinuclidine, pyridine, quinoline and isoquinoline; benzathine, N-methyl-D-glucamine, ethylenediamine, N-ethylmorpholine, N-ethylpiperidine, glucamine, glucosamine, methylglucamine, morpholine, piperazine, piperidine, polyamine resins, procaine, purines, theobromine, hydrabamine salts, and salts with amino acids such as, for example, histidine, arginine, lysine and the like. The foregoing salt forms can be converted by treatment with acid back into the free acid form.

In various aspects, a disclosed therapeutic APBA peptide comprising a protonatable group or moiety, e.g., an amino group, can be used to prepare a pharmaceutically acceptable salt. For example, such a disclosed compound may comprise an isolation step comprising treatment with a suitable inorganic or organic acid. In some cases, it may be desirable in practice to initially isolate a compound from the reaction mixture as a pharmaceutically unacceptable salt and then simply convert the latter back to the free base compound by treatment with a basic reagent, and subsequently convert the free base to a pharmaceutically acceptable acid addition salt. These acid addition salts can be readily prepared using conventional techniques, e.g., by treating the corresponding basic compounds with an aqueous solution containing the desired pharmacologically acceptable anions and then evaporating the resulting solution to dryness, preferably under reduced pressure. Alternatively, they also can be prepared by treating the free base form of the disclosed compound with a suitable pharmaceutically acceptable non-toxic inorganic or organic acid.

Acids that can be used to prepare the pharmaceutically acceptable acid-addition salts of the base compounds are those which can form non-toxic acid-addition salts, i.e., salts containing pharmacologically acceptable anions formed from their corresponding inorganic and organic acids. Exemplary, but non-limiting, inorganic acids include hydrochloric hydrobromic, sulfuric, nitric, phosphoric and the like. Exemplary, but non-limiting, organic acids include acetic, benzenesulfonic, benzoic, camphorsulfonic, citric, ethanesulfonic, fumaric, gluconic, glutamic, isethionic, lactic, maleic, malic, mandelicmethanesulfonic, mucic, pamoic, pantothenic, succinic, tartaric, p-toluenesulfonic acid and the like. In a further aspect, the acid-addition salt comprises an anion formed from hydrobromic, hydrochloric, maleic, phosphoric, sulfuric, and tartaric acids.

In practice, the therapeutic APBA peptides of the present disclosure, or pharmaceutically acceptable salts thereof, of the present disclosure can be combined as the active ingredient in intimate admixture with a pharmaceutical carrier according to conventional pharmaceutical compounding techniques. The carrier can take a wide variety of forms depending on the form of preparation desired for administration, e.g., oral or parenteral (including intravenous). Thus, the pharmaceutical compositions of the present disclosure can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the present disclosure, and/or pharmaceutically acceptable salt(s) thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

It is especially advantageous to formulate the aforementioned pharmaceutical compositions in unit dosage form for ease of administration and uniformity of dosage. The term "unit dosage form," as used herein, refers to physically discrete units suitable as unitary dosages, each unit containing a predetermined quantity of active ingredient calculated to produce the desired therapeutic effect in association with the required pharmaceutical carrier. That is, a "unit dosage form" is taken to mean a single dose wherein all active and inactive ingredients are combined in a suitable system, such that the patient or person administering the drug to the patient can open a single container or package with the entire dose contained therein, and does not have to mix any components together from two or more containers or packages. Typical examples of unit dosage forms are tablets (including scored or coated tablets), capsules or pills for oral administration; single dose vials for injectable solutions or suspension; suppositories for rectal administration; powder packets; wafers; and segregated multiples thereof. This list of unit dosage forms is not intended to be limiting in any way, but merely to represent typical examples of unit dosage forms.

The pharmaceutical compositions disclosed herein comprise a therapeutic APBA peptide of the present disclosure (or pharmaceutically acceptable salt thereof) as an active ingredient, a pharmaceutically acceptable carrier, and optionally one or more additional therapeutic agents. In various aspects, the disclosed pharmaceutical compositions can include a pharmaceutically acceptable carrier and a disclosed compound, or a pharmaceutically acceptable salt thereof. In a further aspect, a disclosed compound, or pharmaceutically acceptable salt thereof, can also be included in a pharmaceutical composition in combination with one or more other therapeutically active compounds. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Techniques and compositions for making dosage forms useful for materials and methods described herein are described, for example, in the following references: *Modem Pharmaceutics*, Chapters 9 and 10 (Banker & Rhodes, Editors, 1979); *Pharmaceutical Dosage Forms: Tablets* (Lieberman et al., 1981); Ansel, *Introduction to Pharmaceutical Dosage Forms* 2nd Edition (1976); *Remington's Pharmaceutical Sciences,* 17th ed. (Mack Publishing Company, Easton, Pa., 1985); *Advances in Pharmaceutical Sciences* Vol 7. (David Ganderton, Trevor Jones, James McGinity, Eds., 1995); *Aqueous Polymeric Coatings for Pharmaceutical Dosage Forms* (Drugs and the Pharmaceutical Sciences, Series 36 (James McGinity, Ed., 1989); *Pharmaceutical Particulate Carriers: Therapeutic Applications: Drugs and the Pharmaceutical Sciences*, Vol 61 (Alain Rolland, Ed., 1993); *Drug Delivery to the Gastrointestinal Tract* (Ellis Horwood Books in the Biological Sciences. Series in Pharmaceutical Technology; J. G. Hardy, S. S. Davis, Clive G. Wilson, Eds.); *Modem Pharmaceutics Drugs and the Pharmaceutical Sciences*, Vol 40 (Gilbert S. Banker, Christopher T. Rhodes, Eds.).

The therapeutic APBA peptides described herein are typically to be administered in admixture with suitable pharmaceutical diluents, excipients, extenders, or carriers (termed herein as a pharmaceutically acceptable carrier, or a carrier) suitably selected with respect to the intended form of administration and as consistent with conventional pharmaceutical practices. The deliverable compound will be in a form suitable for oral, rectal, topical, intravenous injection or parenteral administration. Carriers include solids or liquids, and the type of carrier is chosen based on the type of administration being used. The compounds may be administered as a dosage that has a known quantity of the compound.

Because of the ease in administration, oral administration can be a preferred dosage form, and tablets and capsules represent the most advantageous oral dosage unit forms in which case solid pharmaceutical carriers are obviously employed. However, other dosage forms may be suitable depending upon clinical population (e.g., age and severity of clinical condition), solubility properties of the specific disclosed compound used, and the like. Accordingly, the disclosed compounds can be used in oral dosage forms such as pills, powders, granules, elixirs, tinctures, suspensions, syrups, and emulsions. In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets.

Because of their ease of administration, tablets and capsules are the preferred oral dosage units whereby solid pharmaceutical carriers are employed. Optionally, tablets can be coated by standard aqueous or nonaqueous techniques. The disclosed pharmaceutical compositions in an oral dosage form can comprise one or more pharmaceutical excipient and/or additive. Non-limiting examples of suitable excipients and additives include gelatin, natural sugars such as raw sugar or lactose, lecithin, pectin, starches (for example com starch or amylase), dextran, polyvinyl pyrrolidone, polyvinyl acetate, gum arabic, alginic acid, tylose, talcum, lycopodium, silica gel (for example colloidal), cellulose, cellulose derivatives (for example cellulose ethers in which the cellulose hydroxy groups are partially etherified with lower saturated aliphatic alcohols and/or lower saturated, aliphatic oxyalcohols, for example methyl oxypropyl cellulose, methyl cellulose, hydroxypropyl methyl cellulose, hydroxypropyl methyl cellulose phthalate), fatty acids as well as magnesium, calcium or aluminum salts of fatty acids with 12 to 22 carbon atoms, in particular saturated (for example stearates), emulsifiers, oils and fats, in particular vegetable (for example, peanut oil, castor oil, olive oil, sesame oil, cottonseed oil, com oil, wheat germ oil, sunflower seed oil, cod liver oil, in each case also optionally hydrated); glycerol esters and polyglycerol esters of saturated fatty acids $C_{12}H_{24}O_2$ to $C_{18}H_{36}O_2$ and their mixtures, it being possible for the glycerol hydroxy groups to be totally or also only partly esterified (for example mono-, di- and triglycerides); pharmaceutically acceptable mono- or multivalent alcohols and polyglycols such as polyethylene glycol and derivatives thereof, esters of aliphatic saturated or unsaturated fatty acids (2 to 22 carbon atoms, in particular 10-18 carbon atoms) with monovalent aliphatic alcohols (1 to 20 carbon atoms) or multivalent alcohols such as glycols, glycerol, diethylene glycol, pentacrythritol, sorbitol, mannitol and the like, which may optionally also be etherified, esters of citric acid with primary alcohols, acetic acid, urea, benzyl benzoate, dioxolanes, glyceroformals, tetrahydrofurfuryl alcohol, polyglycol ethers with C1-C12-alcohols, dimethylacetamide, lactamides, lactates, ethylcarbonates, silicones (in particular medium-viscous polydimethyl siloxanes), calcium carbonate, sodium carbonate, calcium phosphate, sodium phosphate, magnesium carbonate and the like.

Other auxiliary substances useful in preparing an oral dosage form are those which cause disintegration (so-called disintegrants), such as: cross-linked polyvinyl pyrrolidone, sodium carboxymethyl starch, sodium carboxymethyl cellulose or microcrystalline cellulose. Conventional coating substances may also be used to produce the oral dosage form. Those that may for example be considered are: polymerizates as well as copolymerizates of acrylic acid and/or methacrylic acid and/or their esters; copolymerizates of acrylic and methacrylic acid esters with a lower ammonium group content (for example EUDRAGITt® RS), copolymerizates of acrylic and methacrylic acid esters and trimethyl ammonium methacrylate (for example EUDRAGIT® RL); polyvinyl acetate; fats, oils, waxes, fatty alcohols; hydroxypropyl methyl cellulose phthalate or acetate succinate; cellulose acetate phthalate, starch acetate phthalate as well as polyvinyl acetate phthalate, carboxy methyl cellulose; methyl cellulose phthalate, methyl cellulose succinate, phthalate succinate as well as methyl cellulose phthalic acid half ester; zein; ethyl cellulose as well as ethyl cellulose succinate; shellac, gluten; ethylcarboxyethyl cellulose; ethacrylate-maleic acid anhydride copolymer; maleic acid anhydride-vinyl methyl ether copolymer; styrol-maleic acid copolymerizate; 2-ethyl-hexyl-acrylate maleic acid anhydride; crotonic acid-vinyl acetate copolymer; glutaminic acid/glutamic acid ester copolymer; carboxymethylethylcellulose glycerol monooctanoate; cellulose acetate succinate; polyarginine.

Plasticizing agents that may be considered as coating substances in the disclosed oral dosage forms are: citric and tartaric acid esters (acetyl-triethyl citrate, acetyl tributyl-, tributyl-, triethyl-citrate); glycerol and glycerol esters (glycerol diacetate, -triacetate, acetylated monoglycerides, castor oil); phthalic acid esters (dibutyl-, diamyl-, diethyl-, dimethyl-, dipropylphthalate), di-(2-methoxy- or 2-ethoxyethyl)-phthalate, ethylphthalyl glycolate, butylphthalylethyl glycolate and butylglycolate; alcohols (propylene glycol, polyethylene glycol of various chain lengths), adipates (diethyladipate, di-(2-methoxy- or 2-ethoxyethyl)-adipate; benzophenone; diethyl- and diburylsebacate, dibutylsuccinate, dibutyltartrate; diethylene glycol dipropionate; ethyleneglycol diacetate, -dibutyrate, -dipropionate; tributyl phosphate, tributyrin; polyethylene glycol sorbitan monooleate (polysorbates such as Polysorbar 50); sorbitan monooleate.

Moreover, suitable binders, lubricants, disintegrating agents, coloring agents, flavoring agents, flow-inducing agents, and melting agents may be included as carriers. The pharmaceutical carrier employed can be, for example, a solid, liquid, or gas. Examples of solid carriers include, but are not limited to, lactose, terra alba, sucrose, glucose, methylcellulose, dicalcium phosphate, calcium sulfate, mannitol, sorbitol talc, starch, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In various aspects, a binder can include, for example, starch, gelatin, natural sugars such as glucose or β-lactose, com sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. In a further aspect, a disintegrator can include, for example, starch, methyl cellulose, agar, bentonite, xanthan gum, and the like.

In various aspects, an oral dosage form, such as a solid dosage form, can comprise a disclosed compound that is attached to polymers as targetable drug carriers or as a prodrug. Suitable biodegradable polymers useful in achieving controlled release of a drug include, for example, polylactic acid, polyglycolic acid, copolymers of polylactic and polyglycolic acid, caprolactones, polyhydroxy butyric acid, polyorthoesters, polyacetals, polydihydropyrans, polycyanoacylates, and hydrogels, preferably covalently crosslinked hydrogels.

Tablets may contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period.

A tablet containing a disclosed compound can be prepared by compression or molding, optionally with one or more accessory ingredients or adjuvants. Compressed tablets can be
prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

In various aspects, a solid oral dosage form, such as a tablet, can be coated with an enteric coating to prevent ready decomposition in the stomach. In various aspects, enteric coating agents include, but are not limited to, hydroxypropylmethylcellulose phthalate, methacrylic acidmethacrylic acid ester copolymer, polyvinyl acetate-phthalate and cellulose acetate phthalate. Various enteric coating materials may be selected on the basis of testing to achieve an enteric coated dosage form designed ab initio to have a preferable combination of dissolution time, coating thicknesses and diametral crushing strength (e.g., see S. C. Porter et al. "The Properties of Enteric Tablet Coatings Made From Polyvinyl Acetate-phthalate and Cellulose acetate Phthalate", J. Pharm. Pharmacol. 22:42p (1970)). In a further aspect, the enteric coating may comprise hydroxypropylmethylcellulose phthalate, methacrylic acid-methacrylic acid ester copolymer, polyvinyl acetatephthalate and cellulose acetate phthalate.

In various aspects, an oral dosage form can be a solid dispersion with a water soluble or a water insoluble carrier. Examples of water soluble or water insoluble carrier include, but are not limited to, polyethylene glycol, polyvinylpyrrolidone, hydroxypropylmethyl-cellulose, phosphatidylcholine, polyoxyethylene hydrogenated castor oil, hydroxypropylmethylcellulose phthalate, carboxymethylethylcellulose, or hydroxypropylmethylcellulose, ethyl cellulose, or stearic acid.

In various aspects, an oral dosage form can be in a liquid dosage form, including those that are ingested, or alternatively, administered as a mouth wash or gargle. For example, a liquid dosage form can include aqueous suspensions, which contain the active materials in admixture with excipients suitable for the manufacture of aqueous suspensions. In addition, oily suspensions may be formulated by suspending the active ingredient in a vegetable oil, for example *arachis* oil, olive oil, sesame oil or coconut oil, or in a mineral oil such as liquid paraffin. Oily suspensions may also contain various excipients. The pharmaceutical compositions of the present disclosure may also be in the form of oil-in-water emulsions, which may also contain excipients such as sweetening and flavoring agents.

For the preparation of solutions or suspensions it is, for example, possible to use water, particularly sterile water, or physiologically acceptable organic solvents, such as alcohols (ethanol, propanol, isopropanol, 1,2-propylene glycol, polyglycols and their derivatives, fatty alcohols, partial esters of glycerol), oils (for example peanut oil, olive oil, sesame oil, almond oil, sunflower oil, soya bean oil, castor oil, bovine hoof oil), paraffins, dimethyl sulfoxide, triglycerides and the like.

In the case of a liquid dosage form such as a drinkable solutions, the following substances may be used as stabilizers or solubilizers: lower aliphatic mono- and multivalent alcohols with 2-4 carbon atoms, such as ethanol, n-propanol, glycerol, polyethylene glycols with molecular weights between 200-600 (for example 1 to 40% aqueous solution), diethylene glycol monoethyl ether, 1,2-propylene glycol, organic amides, for example amides of aliphatic C1-C6-carboxylic acids with ammonia or primary, secondary or tertiary C1-C4-amines or C1-C4-hydroxy amines such as urea, urethane, acetamide, N-methyl acetamide, N,N-diethyl acetamide, N,N-dimethyl acetamide, lower aliphatic amines and diamines with 2-6 carbon atoms, such as ethylene diamine, hydroxyethyl theophylline, tromethamine (for example as 0.1 to 20% aqueous solution), aliphatic amino acids.

In preparing the disclosed liquid dosage form can comprise solubilizers and emulsifiers such as the following non-limiting examples can be used: polyvinyl pyrrolidone, sorbitan fatty acid esters such as sorbitan trioleate, phosphatides such as lecithin, acacia, tragacanth, polyoxyethylated sorbitan monooleate and other ethoxylated fatty acid esters of sorbitan, polyoxyethylated fats, polyoxyethylated oleotriglycerides, linolizated oleotriglycerides, polyethylene oxide condensation products of fatty alcohols, alkylphenols or fatty acids or also lmethyl-3-(2-hydroxyethypimidazolidone-(2). In this context, polyoxyethylated means that the substances in question contain polyoxyethylene chains, the degree of polymerization of which generally lies between 2 and 40 and in particular between 10 and 20. Polyoxyethylated substances of this kind may for example be obtained by reaction of hydroxyl group-containing compounds (for example mono- or diglycerides or unsaturated compounds such as those containing oleic acid radicals) with ethylene oxide (for example 40 mol ethylene oxide per 1 mol glyceride). Examples of oleotriglycerides are olive oil, peanut oil, castor oil, sesame oil, cottonseed oil, com oil. See also Dr. H. P. Fiedler "Lexikon der Hillsstoffe for Pharmazie, Kostnetik and angrenzende Gebiete" 1971, pages 191-195.

In various aspects, a liquid dosage form can further comprise preservatives, stabilizers, buffer substances, flavor correcting agents, sweeteners, colorants, antioxidants and complex formers and the like. Complex formers which may be for example be considered are: chelate formers such as ethylene diamine retrascetic acid, nitrilotriacetic acid, diethylene triamine pentacetic acid and their salts.

It may optionally be necessary to stabilize a liquid dosage form with physiologically acceptable bases or buffers to a pH range of approximately 6 to 9. Preference may be given to as neutral or weakly basic a pH value as possible (up to pH 8).

In order to enhance the solubility and/or the stability of a disclosed compound in a disclosed liquid dosage form, a parenteral injection form, or an intravenous injectable form, it can be advantageous to employ α-, β- or γ-cyclodextrins or their derivatives, in particular hydroxyalkyl substituted cyclodextrins, e.g. 2-hydroxypropyl-β-cyclodextrin or sulfobutyl-β-cyclodextrin. Also co-solvents such as alcohols may improve the solubility and/or the stability of the compounds according to the present disclosure in pharmaceutical compositions.

In various aspects, a disclosed liquid dosage form, a parenteral injection form, or an intravenous injectable form can further comprise liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Pharmaceutical compositions of the present disclosure suitable injection, such as parenteral administration, such as intravenous, intramuscular, or subcutaneous administration. Pharmaceutical compositions for injection can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present disclosure suitable for parenteral administration can include sterile aqueous or oleaginous solutions, suspensions, or dispersions. Furthermore, the compositions can be in the form of sterile powders for the extemporaneous preparation of such sterile injectable solutions or dispersions. In some aspects, the final injectable form is sterile and must be effectively fluid for use in a syringe. The pharmaceutical compositions should be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Injectable solutions, for example, can be prepared in which the carrier comprises saline solution, glucose solution or a mixture of saline and glucose solution. Injectable suspensions may also be prepared in which case appropriate liquid carriers, suspending agents and the like may be employed. In some aspects, a disclosed parenteral formulation can comprise about 0.01-0.1 M, e.g. about 0.05 M, phosphate buffer. In a further aspect, a disclosed parenteral formulation can comprise about 0.9% saline.

In various aspects, a disclosed parenteral pharmaceutical composition can comprise pharmaceutically acceptable carriers such as aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include but not limited to water, alcoholic/aqueous solutions, emulsions or suspensions, including saline and buffered media. Parenteral vehicles can include mannitol, normal serum albumin, sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, collating agents, inert gases and the like. In a further aspect, a disclosed parenteral pharmaceutical composition may contain minor amounts of additives such as substances that enhance isotonicity and chemical stability, e.g., buffers and preservatives. Also contemplated for injectable pharmaceutical compositions are solid form preparations that are intended to be converted, shortly before use, to liquid form preparations. Furthermore, other adjuvants can be included to render the formulation isotonic with the blood of the subject or patient.

In addition to the pharmaceutical compositions described herein above, the disclosed compounds can also be formulated as a depot preparation. Such long acting formulations can be administered by implantation (e.g., subcutaneously or intramuscularly) or by intramuscular injection. Thus, for example, the compounds can be formulated with suitable polymeric or hydrophobic materials (e.g., as an emulsion in an acceptable oil) or ion exchange resins, or as sparingly soluble derivatives, e.g., as a sparingly soluble salt.

Pharmaceutical compositions of the present disclosure can be in a form suitable for topical administration. As used herein, the phrase "topical application" means administration onto a biological surface, whereby the biological surface includes, for example, a skin area (e.g., hands, forearms, elbows, legs, face, nails, anus and genital areas) or a mucosal membrane. By selecting the appropriate carrier and optionally other ingredients that can be included in the composition, as is detailed herein below, the compositions of the present invention may be formulated into any form typically employed for topical application. A topical pharmaceutical composition can be in a form of a cream, an ointment, a paste, a gel, a lotion, milk, a suspension, an aerosol, a spray, foam, a dusting powder, a pad, and a patch. Further, the compositions can be in a form suitable for use in transdermal devices. These formulations can be prepared, utilizing a compound of the present disclosure, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

In the compositions suitable for percutaneous administration, the earner optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment, or the like.

Ointments are semisolid preparations, typically based on petrolatum or petroleum derivatives. The specific ointment base to be used is one that provides for optimum delivery for the active agent chosen for a given formulation, and, preferably, provides for other desired characteristics as well (e.g., emollience). As with other carriers or vehicles, an ointment base should be inert, stable, nonirritating and nonsensitizing. As explained in *Remington: The Science and Practice of Pharmacy*, 19th Ed., Easton, Pa.: Mack Publishing Co. (1995), pp. 1399-1404, ointment bases may be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin and hydrophilic petrolatum. Emulsion ointment bases are either water-in-oil (W/O) emulsions or oil-in-water (O/W) emulsions, and include, for example, cetyl alcohol, glyceryl monostearate, lanolin and stearic acid. Preferred water-soluble ointment bases are prepared from polyethylene glycols of varying molecular weight.

Lotions are preparations that are to be applied to the skin surface without friction. Lotions are typically liquid or semiliquid preparations in which solid particles, including the active agent, are present in a water or alcohol base. Lotions are typically preferred for treating large body areas, due to the ease of applying a more fluid composition. Lotions are typically suspensions of solids, and oftentimes comprise a liquid oily emulsion of the oil-in-water type. It is generally necessary that the insoluble matter in a lotion be finely divided. Lotions typically contain suspending agents to produce better dispersions as well as compounds useful for localizing and holding the active agent in contact with the skin, such as methylcellulose, sodium carboxymethylcellulose, and the like.

Creams are viscous liquids or semisolid emulsions, either oil-in-water or water-in-oil. Cream bases are typically water-washable, and contain an oil phase, an emulsifier and an aqueous phase. The oil phase, also called the "internal" phase, is generally comprised of petrolatum and/or a fatty alcohol such as cetyl or stearyl alcohol. The aqueous phase typically, although not necessarily, exceeds the oil phase in volume, and generally contains a humectant. The emulsifier in a cream formulation is generally a nonionic, anionic, cationic or amphoteric surfactant. Reference may be made to *Remington: The Science and Practice of Pharmacy*, supra, for further information.

Pastes are semisolid dosage forms in which the bioactive agent is suspended in a suitable base. Depending on the nature of the base, pastes are divided between fatty pastes or those made from a single-phase aqueous gel. The base in a fatty paste is generally petrolatum, hydrophilic petrolatum and the like. The pastes made from single-phase aqueous gels generally incorporate carboxymethylcellulose or the like as a base. Additional reference may be made to *Remington: The Science and Practice of Pharmacy*, for further information.

Gel formulations are semisolid, suspension-type systems. Single-phase gels contain organic macromolecules distributed substantially uniformly throughout the carrier liquid, which is typically aqueous, but also, preferably, contain an alcohol and, optionally, an oil. Preferred organic macromolecules, i.e., gelling agents, are crosslinked acrylic acid polymers such as the family of carbomer polymers, e.g., carboxypolyalkylenes that may be obtained commercially under the trademark Carbopol™. Other types of preferred polymers in this context are hydrophilic polymers such as polyethylene oxides, polyoxyethylene-polyoxypropylene copolymers and polyvinylalcohol; modified cellulose, such as hydroxypropyl cellulose, hydroxyethyl cellulose, hydroxypropyl methylcellulose, hydroxypropyl methylcellulose phthalate, and methyl cellulose; gums such as tragacanth and xanthan gum; sodium alginate; and gelatin. In order to prepare a uniform gel, dispersing agents such as alcohol or glycerin can be added, or the gelling agent can be dispersed by trituration, mechanical mixing or stirring, or combinations thereof.

Sprays generally provide the active agent in an aqueous and/or alcoholic solution which can be misted onto the skin for delivery. Such sprays include those formulated to provide for concentration of the active agent solution at the site of administration following delivery, e.g., the spray solution can be primarily composed of alcohol or other like volatile liquid in which the active agent can be dissolved. Upon delivery to the skin, the carrier evaporates, leaving concentrated active agent at the site of administration.

Foam compositions are typically formulated in a single or multiple phase liquid form and housed in a suitable container, optionally together with a propellant which facilitates the expulsion of the composition from the container, thus transforming it into a foam upon application. Other foam forming techniques include, for example the "Bag-in-a-can" formulation technique. Compositions thus formulated typically contain a low-boiling hydrocarbon, e.g., isopropane. Application and agitation of such a composition at the body temperature cause the isopropane to vaporize and generate the foam, in a manner similar to a pressurized aerosol foaming system. Foams can be water-based or aqueous alkanolic, but are typically formulated with high alcohol content which, upon application to the skin of a user, quickly evaporates, driving the active ingredient through the upper skin layers to the site of treatment.

Skin patches typically comprise a backing, to which a reservoir containing the active agent is attached. The reservoir can be, for example, a pad in which the active agent or composition is dispersed or soaked, or a liquid reservoir. Patches typically further include a frontal water permeable adhesive, which adheres and secures the device to the treated region. Silicone rubbers with self-adhesiveness can alternatively be used. In both cases, a protective permeable layer can be used to protect the adhesive side of the patch prior to its use. Skin patches may further comprise a removable cover, which serves for protecting it upon storage.

Examples of patch configuration which can be utilized with the present invention include a single-layer or multi-layer drug-in-adhesive systems which are characterized by the inclusion of the drug directly within the skin-contacting adhesive. In such a transdermal patch design, the adhesive not only serves to affix the patch to the skin, but also serves as the formulation foundation, containing the drug and all the excipients under a single backing film. In the multi-layer drug-inadhesive patch a membrane is disposed between two distinct drug-in-adhesive layers or multiple drug-in-adhesive layers are incorporated under a single backing film.

Examples of pharmaceutically acceptable carriers that are suitable for pharmaceutical compositions for topical applications include carrier materials that are well-known for use in the cosmetic and medical arts as bases for e.g., emulsions, creams, aqueous solutions, oils, ointments, pastes, gels, lotions, milks, foams, suspensions, aerosols and the like, depending on the final form of the composition. Representative examples of suitable carriers according to the present invention therefore include, without limitation, water, liquid alcohols, liquid glycols, liquid polyalkylene glycols, liquid esters, liquid amides, liquid protein hydrolysates, liquid alkylated protein hydrolysates, liquid lanolin and lanolin derivatives, and like materials commonly employed in cosmetic and medicinal compositions. Other suitable carriers according to the present invention include, without limitation, alcohols, such as, for example, monohydric and polyhydric alcohols, e.g., ethanol, isopropanol, glycerol, sorbitol, 2-methoxyethanol, diethyleneglycol, ethylene glycol, hexyleneglycol, mannitol, and propylene glycol; ethers such as diethyl or dipropyl ether; polyethylene glycols and methoxypolyoxyethylenes (carbowaxes having molecular weight ranging from 200 to 20,000); polyoxyethylene glycerols, polyoxyethylene sorbitols, stearoyl diacetin, and the like.

Topical compositions of the present disclosure can, if desired, be presented in a pack or dispenser device, such as an FDA-approved kit, which may contain one or more unit dosage forms containing the active ingredient. The dispenser device may, for example, comprise a tube. The pack or dispenser device may be accompanied by instructions for administration. The pack or dispenser device may also be accompanied by a notice in a form prescribed by a governmental agency regulating the manufacture, use, or sale of pharmaceuticals, which notice is reflective of approval by the agency of the form of the compositions for human or veterinary administration. Such notice, for example, may include labeling approved by the U.S. Food and Drug Administration for prescription drugs or of an approved product insert. Compositions comprising the topical composition of the invention formulated in a pharmaceutically acceptable carrier may also be prepared, placed in an appropriate container, and labeled for treatment of an indicated condition.

Another patch system configuration which can be used by the present invention is a reservoir transdermal system design which is characterized by the inclusion of a liquid compartment containing a drug solution or suspension separated from the release liner by a semipermeable membrane and adhesive. The adhesive component of this patch system can either be incorporated as a continuous layer between the membrane and the release liner or in a concentric configuration around the membrane. Yet another patch system configuration which can be utilized by the present invention is a matrix system design which is characterized by the inclusion of a semisolid matrix containing a drug solution or suspension which is in direct contact with the release liner. The component responsible for skin adhesion is incorporated in an overlay and forms a concentric configuration around the semisolid matrix.

Pharmaceutical compositions of the present disclosure can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in molds.

Pharmaceutical compositions containing a compound of the present disclosure, and/or pharmaceutically acceptable salts thereof, can also be prepared in powder or liquid concentrate form.

The pharmaceutical composition (or formulation) may be packaged in a variety of ways. Generally, an article for distribution includes a container that contains the pharmaceutical composition in an appropriate form. Suitable containers are well known to those skilled in the art and include materials such as bottles (plastic and glass), sachets, foil blister packs, and the like. The container may also include a tamper proof assemblage to prevent indiscreet access to the contents of the package. In addition, the container typically has deposited thereon a label that describes the contents of the container and any appropriate warnings or instructions.

The disclosed pharmaceutical compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Pharmaceutical compositions comprising a disclosed compound formulated in a compatible pharmaceutical carrier may also be prepared, placed in an appropriate container, and labeled for treatment of an indicated condition.

The exact dosage and frequency of administration depends on the particular disclosed compound, a product of a disclosed method of making, a pharmaceutically acceptable salt, solvate, or polymorph thereof, a hydrate thereof, a solvate thereof, a polymorph thereof, or a stereochemically isomeric form thereof; the particular condition being treated and the severity of the condition being treated; various factors specific to the medical history of the subject to whom the dosage is administered such as the age; weight, sex, extent of disorder and general physical condition of the particular subject, as well as other medication the individual may be taking; as is well known to those skilled in the art. Furthermore, it is evident that said effective daily amount may be lowered or increased depending on the response of the treated subject and/or depending on the evaluation of the physician prescribing the compounds of the present disclosure.

Depending on the mode of administration, the pharmaceutical composition will comprise from 0.05 to 99% by weight, preferably from 0.1 to 70% by weight, more preferably from 0.1 to % by weight of the active ingredient, and, from 1 to 99.95% by weight, preferably from 30 to 99.9% by weight, more preferably from 50 to 99.9% by weight of a pharmaceutically acceptable carrier, all percentages being based on the total weight of the composition.

In the treatment of conditions as discussed elsewhere herein, an appropriate dosage level will generally be about 0.01 to 1000 mg per kg patient body weight per day and can be administered in single or multiple doses. In various aspects, the dosage level will be about 0.1 to about 500 mg/kg per day, about 0.1 to 250 mg/kg per day, or about 0.5 to 100 mg/kg per day. A suitable dosage level can be about 0.01 to 1000 mg/kg per day, about 0.01 to 500 mg/kg per day, about 0.01 to 250 mg/kg per day, about 0.05 to 100 mg/kg per day, or about 0.1 to 50 mg/kg per day. Within this range the dosage can be 0.05 to 0.5, 0.5 to 5.0 or 5.0 to 50 mg/kg per day. For oral administration, the compositions are preferably provided in the form of tablets containing 1.0 to 1000 mg of the active ingredient, particularly 1.0, 5.0, 10, 15, 20, 25, 50, 75, 100, 150, 200, 250, 300, 400, 500, 600, 750, 800, 900 and 1000 mg of the active ingredient for the symptomatic adjustment of the dosage of the patient to be treated. The compound can be administered on a regimen of 1 to 4 times per day, preferably once or twice per day. This dosing regimen can be adjusted to provide the optimal therapeutic response.

Such unit doses as described hereinabove and hereinafter can be administered more than once a day, for example, 2, 3, 4, 5 or 6 times a day. In various aspects, such unit doses can be administered 1 or 2 times per day, so that the total dosage for a 70 kg adult is in the range of to about 15 mg per kg weight of subject per administration. In a further aspect, dosage is to about 1.5 mg per kg weight of subject per administration, and such therapy can extend for a number of weeks or months, and in some cases, years. It will be understood, however, that the specific dose level for any particular patient will depend on a variety of factors including the activity of the specific compound employed; the age, body weight, general health, sex and diet of the individual being treated; the time and route of administration; the rate of excretion; other drugs that have previously been administered; and the severity of the particular disease undergoing therapy, as is well understood by those of skill in the area.

A typical dosage can be one 1 mg to about 100 mg tablet or 1 mg to about 300 mg taken once a day, or, multiple times per day, or one time-release capsule or tablet taken once a day and containing a proportionally higher content of active ingredient. The time-release effect can be obtained by capsule materials that dissolve at different pH values, by capsules that release slowly by osmotic pressure, or by any other known means of controlled release.

It can be necessary to use dosages outside these ranges in some cases as will be apparent to those skilled in the art. Further, it is noted that the clinician or treating physician will know how and when to start, interrupt, adjust, or terminate therapy in conjunction with individual patient response.

The present disclosure is further directed to a method for the manufacture of a medicament for anti-microbial activity (e.g., treatment of one or more microbial infections) in mammals (e.g., humans) comprising combining one or more disclosed therapeutic APBA peptides with a pharmaceutically acceptable carrier or diluent. Thus, in one aspect, the present disclosure further relates to a method for manufacturing a medicament comprising combining at least one disclosed therapeutic APBA peptide with a pharmaceutically acceptable carrier or diluent.

The disclosed pharmaceutical compositions can further comprise other therapeutically active compounds, which are usually applied in the treatment of the above mentioned pathological or clinical conditions.

It is understood that the disclosed compositions can be prepared from the disclosed therapeutic APBA peptides. It is also understood that the disclosed compositions can be employed in the disclosed methods of using.

As already mentioned, the present disclosure relates to a pharmaceutical composition comprising a therapeutically effective amount of a disclosed therapeutic APBA peptide, a pharmaceutically acceptable salt thereof, and a pharmaceutically acceptable carrier. Additionally, the present disclosure relates to a process for preparing such a pharmaceutical composition, characterized in that a pharmaceutically acceptable carrier is intimately mixed with a therapeutically effective amount of a compound according to the present disclosure.

As already mentioned, the present disclosure also relates to a pharmaceutical composition comprising a disclosed compound, a product of a disclosed method of making, a pharmaceutically acceptable salt, a hydrate thereof, a solvate thereof, a polymorph thereof, and one or more other drugs in the treatment, prevention, control, amelioration, or reduction of risk of diseases or conditions for a disclosed compound or the other drugs may have utility as well as to the use of such a composition for the manufacture of a medicament. The present disclosure also relates to a combination of disclosed therapeutic APBA peptide, a pharmaceutically acceptable salt thereof, and a therapeutic agent that is known to treat a disease or disorder associated with aberrant protein expression, a cancer, a bacterial, fungal, or viral disease. In another aspect, the disclosed therapeutic APBA peptide can be conjugated to an imaging or contrast agent for use in imaging cells, organs, tissues, and/or proteins. The present disclosure also relates to such a combination for use as a medicine. The present disclosure also relates to a product comprising (a) disclosed therapeutic APBA peptide, or a pharmaceutically acceptable salt thereof, and (b) an additional antimicrobial therapeutic agent, as a combined preparation for simultaneous, separate or sequential use in the treatment or prevention of a condition in a mammal, including a human, the treatment or prevention of which is affected or facilitated by the modulatory effect of the disclosed compound and the additional therapeutic agent. The different drugs of such a combination or product may be combined in a single preparation together with pharmaceutically acceptable carriers or diluents, or they may each be present in a separate preparation together with pharmaceutically acceptable carriers or diluents.

Methods of Using Therapeutic APBA Peptides

Antibacterial Uses of APBA Peptides

In various aspects, the present disclosure provides methods of treating an infectious disease comprising administration of a therapeutically effective amount of a disclosed APBA therapeutic peptide or a disclosed pharmaceutical composition to a subject in need thereof. It is understood that reference to a disclosed APBA therapeutic peptide is inclusive of the disclosed APBA therapeutic peptide, as well as pharmaceutically acceptable salt, hydrate, solvate, or polymorph forms thereof and a disclosed APBA therapeutic peptide further comprising an antibiotic agent, an antiviral agent, an antifungal agent, an anticancer agent, an imaging agent, a contrast agent, or a combination thereof; and reference to a disclosed pharmaceutical composition is inclusive of a pharmaceutical composition comprising a disclosed APBA therapeutic peptide or pharmaceutically acceptable salt, hydrate, solvate, or polymorph forms of a disclosed APBA therapeutic peptide, and pharmaceutical compositions comprising a disclosed APBA therapeutic peptide further comprising an antibiotic agent, an antiviral agent, an antifungal agent, an anticancer agent, an imaging agent, a contrast agent, or a combination thereof.

It is understood that treating an infectious disease is inclusive of treating, preventing, ameliorating, controlling or reducing the risk of a variety of bacterial infections, including an infection associated with Gram positive bacteria, Gram negative bacteria, or mycobacteria, wherein the patient or subject would benefit from an antibacterial agent. For example, a treatment can include binding a disclosed APBA therapeutic peptide, optionally further comprising an antibiotic agent, an antiviral agent, an antifungal agent, an anticancer agent, an imaging agent, a contrast agent, or a combination thereof, to a target bacteria or bacterial proteins in a subject infected with said target bacteria, and wherein the disclosed APBA therapeutic peptide via binding and/or binding with delivery of antibiotic agent, an antiviral agent, an antifungal agent, an anticancer agent, an imaging agent, a contrast agent, or a combination thereof to the target bacteria or bacterial protein. In one aspect, provided is a method of treating or preventing a bacterial infection in a subject comprising the step of administering to the subject at least one disclosed APBA therapeutic peptide or at least one disclosed pharmaceutical composition in a dosage and amount effective to treat the disorder in the subject.

Also provided is a method for the treatment of one or more disorders associated with infection by a target bacteria wherein inhibiting binding of a disclosed APBA therapeutic peptide can sterilize or decrease the presence of the pathogenic bacteria in a subject comprising the step of administering to the subject at least one disclosed APBA therapeutic peptide or at least one disclosed pharmaceutical composition in a dosage and amount effective to treat the disorder in the subject.

Also provided is a method for the treatment of a bacterial infection in a vertebrate animal comprising the step of administering to the mammal at least one disclosed compound, composition, or medicament. In some aspects, the vertebrate animal is a mammal.

In a further aspect, the vertebrate animal is a fish, a bird, or a mammal. In a still further aspect, the vertebrate animal is a livestock animal. In yet a further aspect, the vertebrate animal is a companion animal. In an even further aspect, the vertebrate animal is a farm animal. In a still further aspect, the vertebrate animal is a zoo animal. In yet a further aspect, the vertebrate animal is a laboratory animal. In an even further aspect, the vertebrate animal is an aquaculture fish. In a still further aspect, the vertebrate animal is selected from *Bison* sp., *Bos* sp., *Canis* sp., *Capra* sp., *Equus* sp., *Felis* sp., *Gallus* sp., *Lama* sp., *Meleagris* sp., *Oryctolagus* sp., *Ovis* sp., and *Sus* sp.

In a further aspect, the vertebrate animal has been diagnosed with a need for treatment of the infectious disease prior to the administering step.

In a further aspect, the disclosure relates to a method for the treatment of an infectious disease in a vertebrate animal, further comprising the step of identifying a vertebrate animal in need of treatment of the infectious disease.

In a further aspect, administering comprises mixing an effective amount of a disclosed APBA therapeutic peptide with the food of the vertebrate animal. In a still further aspect, administering comprises administering enterally an effective amount of the disclosed APBA therapeutic peptide with the food of the vertebrate animal. In yet a further aspect, administering comprises administering an oral bolus of an effective amount of the disclosed APBA therapeutic peptide with the food of the vertebrate animal.

In various aspects, administering to a vertebrate animal comprises intravenous administration or parenteral administration to the vertebrate animal. In a further aspect, the infectious disease treated in the vertebrate animal is selected from dental infection, dermatitis, diarrhea, ear infection, gastritis, gastroenteritis, genitourinary infection, intestinal infection, lung infection, ocular infection, oral infection, otitis, osteo-articular infection, pharyngitis, papules, pneumonia conjunctivitis, pruritis, pustules, pyoderma, pyothorax, respiratory infection, *salmonellosis*, septicemia, skin infection, soft tissue infection, ulcer, urinary tract infection, and wound infection.

In a further aspect, the disclosure relates to a method for the treatment of an infectious disease in a vertebrate animal, further comprising administering to the vertebrate animal a therapeutically effective amount of second active agent. In a still further aspect, the second active agent is an antibacterial agent. In yet a further aspect, the antibacterial agent is penicillin, a cephalosporin, a sulfonamide, a tetracycline, a lincosamide, an aminoglycoside, or a fluoroquinolone, or combinations thereof. In an even further aspect, the antibacterial agent comprises a compound selected from amoxicillin, ampicillin, azithromycin, cefovecin, cephalexin, chloramphenicol, ciprofloxacin, clavulanic acid, cloxacillin, clindamycin, doxycycline, enrofloxacin, erythromycin, gentamicin, ibafloxacin, kanamycin, lincomycin, marbofloxacin, metronidazole, minocycline, neomycin, novobiocin, ofloxacin, orbifloxacin, oxytetracycline, penicillin G, rifampin, sulfadimethoxine, sulfadiazine, tetracycline, tiamulin, ticarcillin, trimethoprim, and tylosin, or combinations thereof.

The disclosed APBA therapeutic peptides are further useful in a method for the prevention, treatment, control, amelioration, or reduction of risk of the bacterial infections noted herein. The disclosed APBA therapeutic peptides are further useful in a method for the prevention, treatment, control, amelioration, or reduction of risk of the aforementioned bacterial infections in combination with other agents.

In one aspect, the disclosed APBA therapeutic peptides can be used in combination with one or more other drugs in the treatment, prevention, control, amelioration, or reduction of risk of bacterial infections for which disclosed APBA therapeutic peptides or the other drugs can have utility, where the combination of the drugs together are safer or more effective than either drug alone. Such other drug(s) can be administered, by a route and in an amount commonly used therefor, contemporaneously or sequentially with a compound of the present disclosure. When a compound of the present disclosure is used contemporaneously with one or more other drugs, a pharmaceutical composition in unit dosage form containing such other drugs and a disclosed compound is preferred. However, the combination therapy can also include therapies in which a disclosed compound and one or more other drugs are administered on different overlapping schedules. It is also contemplated that when used in combination with one or more other active ingredients, the disclosed APBA therapeutic peptides and the other active ingredients can be used in lower doses than when each is used singly. Accordingly, the pharmaceutical compositions include those that contain one or more other active ingredients, in addition to a compound of the present disclosure.

The above combinations include combinations of a disclosed compound not only with one other active compound, but also with two or more other active compounds. Likewise, disclosed APBA therapeutic peptides can be used in combination with other drugs that are used in the prevention, treatment, control, amelioration, or reduction of risk of the bacterial infections for which disclosed APBA therapeutic peptides are useful. Such other drugs can be administered, by a route and in an amount commonly used therefor, contemporaneously or sequentially with a compound of the present disclosure. When a compound of the present disclosure is used contemporaneously with one or more other drugs, a pharmaceutical composition containing such other drugs in addition to a disclosed compound is preferred. Accordingly, the pharmaceutical compositions include those that also contain one or more other active ingredients, in addition to a compound of the present disclosure.

The weight ratio of a disclosed compound to the second active ingredient can be varied and will depend upon the effective dose of each ingredient. Generally, an effective dose of each will be used. Thus, for example, when a compound of the present disclosure is combined with another agent, the weight ratio of a disclosed compound to the other agent will generally range from about 1000:1 to about 1:1000, preferably about 200:1 to about 1:200. Combinations of a compound of the present disclosure and other active ingredients will generally also be within the aforementioned range, but in each case, an effective dose of each active ingredient should be used.

In such combinations a disclosed compound and other active agents can be administered separately or in conjunction. In addition, the administration of one element can be prior to, concurrently with, or subsequent to the administration of other agent(s). Accordingly, the disclosed APBA therapeutic peptides can be used alone or in combination with other agents which are known to be beneficial in the subject indications or other drugs that affect receptors or enzymes that either increase the efficacy, safety, convenience, or reduce unwanted side effects or toxicity of the other agents. The disclosed APBA therapeutic peptide and the other agent can be coadministered, either in concomitant therapy or in a fixed combination.

In one aspect, the compound can be employed in combination with antibacterial or antimicrobial agents, and combinations thereof, and the like, or the subject compound can be administered in conjunction with the use of physical methods such as with debridement of a wound or infected tissue.

In the treatment of an infectious disease condition, an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level can be about to 250 mg/kg per day, about 0.05 to 100 mg/kg per day, or about 0.1 to 50 mg/kg per day. Within this range the dosage can be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10, 15, 20, 25, 50, 75, 100, 150,200, 250, 300, 400, 500, 600, 750, 800, 900, and 1000 milligrams of the active ingredient for the symptomatic adjustment of the dosage to the patient to be treated. The compounds can be administered on a regimen of 1 to 4 times per day, preferably once or twice per day. This dosage regimen can be adjusted to provide the optimal therapeutic response. It will be understood, however, that the specific dose level and frequency of dosage for any particular patient can be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Thus, in one aspect, the disclosure relates to methods for treating a bacterial infection in at least one cell, comprising the step of contacting the at least one cell with at least one compound of the disclosure, in an amount effective to alter the response in the at least one cell. In a further aspect, the cell is mammalian, for example human. In a further aspect, the cell has been isolated from a subject prior to the contacting step. In a further aspect, contacting is via administration to a subject.

Infectious diseases treatable by the presently disclosed APBA therapeutic peptides can be caused by a variety of bacteria and protozoa. In some embodiments, the infection is a bacterial infection. Exemplary microbial infections that can be treated by the method of the presently disclosed APBA therapeutic peptides include, but are not limited to, infections caused by *Staphylococcus aureus, Enterococcus faecalis, Bacillus anthracis*, a *Streptococcus* species (e.g., *Streptococcus pyogenes* or *Streptococcus pneumoniae*), *Escherichia coli, Pseudomonas aeruginosa, Burkholderia cepacia*, a *Proteus* species (e.g., *Proteus mirabilis* or *Proteus vulgaris*), *Klebsiella pneumoniae, Acinetobacter baumannii, Strenotrophomonas maltophillia, Mycobacterium tuberculosis, Mycobacterium bovis*, other mycobacteria of the tuberculosis complex, and non-tuberculous mycobacteria, including *Mycobacterium ulcerans, Mycobacterium avium*, and *Mycobacterium abscessus*.

An infectious disease that is associated world-wide with a high level of morbidity and mortality is a mycobaterial infection. Mycobacterial infections can cause different diseases such as tuberculosis ("TB"). Additionally, mycobacterial diseases can cause overwhelming, disseminated disease in immunocompromised patients and is the leading killer of people who are HIV infected. In spite of the efforts of numerous health organizations worldwide, the eradication of mycobacterial diseases has never been achieved, nor is eradication imminent. Based on currently available data, about one fourth of the world's population is infected with TB. Moreover, in 2016, 10.4 million people around the world became sick with TB disease and there were 1.7 million TB-related deaths worldwide.

Although over 37 species of *Mycobacterium* have been identified, more than 95% of all human infections are caused by seven species of mycobacteria: *M. tuberculosis, M. avium intracellulare, M. abscessus, M. kansasii, M. fortuitum, M. chelonae*, and *M. leprae*. Cases of human tuberculosis are predominantly caused by mycobacterial species comprising *M. tuberculosis, M. bovis*, or *M. africanum*. Infection is typically initiated by the inhalation of infectious particles, which are able to reach the terminal pathways in the lungs. Following engulfment by alveolar macrophages, the bacilli are able to replicate freely, with eventual destruction of the phagocytic cells. A cascade effect ensues wherein destruction of the phagocytic cells causes additional macrophages and lymphocytes to migrate to the site of infection, where they too are ultimately eliminated.

Mycobacteria can be classified into several major groups for purpose of diagnosis and treatment: *M. tuberculosis* complex (MTBC), which can cause tuberculosis (*M. tuberculosis, M. bovis, M. africanum*, and *M. microti*); *M. leprae*, which causes Hansen's disease or leprosy; and Nontuberculous mycobacteria (NTM) are all the other mycobacteria, which can cause pulmonary disease resembling tuberculosis, lymphadenitis, skin disease, or disseminated disease. MTBC members are causative agents of human and animal tuberculosis. Species in this complex include: *M. tuberculosis*, the major cause of human tuberculosis, *M. bovis, M. bovis ECG, M. africanum, M. canetti, M. caprae, M. microti*, and *M. pinnipedii*.

In a further aspect, the present disclosure provides methods of treating a mycobacterial infections, including those caused by mycobacteria such as *M. tuberculosis, M. bovis, M. bovis BCG, M. africanum, M. canetti, M. caprae, M. microti, M. pinnipedii, M. avium, M. avium paratuberculosis, M. avium silvaticum, M. avium "homninissuis," M. colombiense, M. asiaticum, M. gordonae, M. gastri, M. kansasii, M. hiberniae, M. nonchromogenicum, M. terrae, M. triviale, M. ulcerans, M. pseudoshottsii, M. shottsii, M. triplex, M. genavense, M. florentinum, M. lentiflavum, M. palustre, M. kubicae, M. parascrofulaceum, M. heidelbergense, M. interjectum, M. simiae, M. branderi, M. cookii, M. celatum, M. bohemicum, M. haemophilum, M. malmoense, M. szulgai, M. leprae, M. lepraemurium, M. lepromatosis, M. botniense, M. chimaera, M. conspicuum, M. doricum, M. farcinogenes, M. heckeshornense, M. intracellulare, M. lacus, M. marinum, M. monacense, M. montefiorense, M. murale, M. nebraskense, M. saskatchewanense, M. scrofulaceum, M. shimoidei, M. tusciae, M. xenopi, M. interme-* dium, *M. abscessus*, *M. chelonae*, *M. bolletii*, *M. fortuitum*, *M. fortuitum* subsp. *acetamidolyticum*, *M. boenickei*, *M. peregrinum*, *M. porcinum*, *M. senegalense*, *M. septicum*, *M. neworleansense*, *M. houstonense*, *M. mucogenicum*, *M. mageritense*, *M. brisbanense*, *M. cosmeticum*, *M. parafortuitum*, *M. austroafricanum*, *M. diernhoferi*, *M. hodleri*, *M. neoaurum*, *M. frederiksbergense*, *M. aurum*, *M. vaccae*, *M. chitae*, *M. fallax*, *M. confluentis*, *M. flavescens*, *M. madagascariense*, *M. phlei*, *M. smnegmatis*, *M. goodii*, *M. wolinskyi*, *M. thermoresistibile*, *M. gadium*, *M. komossense*, *M. obuense*, *M. sphagni*, *M. agri*, *M. aichiense*, *M. alvei*, *M. arupense*, *M. brumae*, *M. canariasense*, *M. chubuense*, *M. conceptionense*, *M. duvalii*, *M. elephantis*, *M. gilvum*, *M. hassiacum*, *M. holsaticum*, *M. immunogenum*, *M. massiliense*, *M. moriokaense*, *M. psychrotolerans*, *M. pyrenivorans*, *M. vanbaalenii*, *M. pulveris*, *M. arosiense*, *M. aubagnense*, *M. caprae*, *M. chlorophenolicum*, *M. fluoroanthenivorans*, *M. kumamotonense*, *M. novocastrense*, *M. parmense*, *M. phocaicum*, *M. poriferae*, *M. rhodesiae*, *M. seoulense*, and *M. tokaiense*.

In a further aspect, the present disclosure provides methods of treating an infectious disease such as a mycobacterial infection. In various aspects, the mycobacterial infection can be associated with a *Mycobacterium tuberculosis* infection. In a still further aspect, the *Mycobacterium tuberculosis* infection is associated with infection by an MDR strain of *Mycobacterium tuberculosis*. In a yet further aspect, the *Mycobacterium tuberculosis* infection is associated with infection by an XDR strain of *Mycobacterium tuberculosis*.

In a further aspect, the present disclosure provides methods of treating an infectious disease such as a Gram positive bacterial infection. In a still further aspect, the Gram positive bacteria is selected from a *Bacillus* sp., a *Clostridium* sp., a *Corynebacterium* sp, an *Enterococcus* sp., a *Mycoplasma* sp., a *Staphylococcus* sp., or a *Streptococcus* sp. In yet a further aspect, the Gram positive bacteria is vancomycin resistant *Enterococcus* sp. (VRE). In an even further aspect, the Gram positive bacteria is methicillin resistant *Staphylococcus* sp. (MRS). In a still further aspect, the Gram positive bacteria is selected from *Bacillus anthracis*, *Bacillus cereus*, *Bacillus subtilis*, *Clostridium difficile*, *Clostridium tetani*, *Clostridium botulinum*, *Clostridium perfringens*, *Corynebacterium diphtheria*, *Enterococcus faecalis*, *Enterococcus faecium*, *Listeria monocytogenes*, *Listeria ivanovii*, *Micrococcus luteus*, *Mycoplasma genitalium*, *Mycoplasma pneumoniae*, *Staphylococcus aureus*, *Staphylococcus epidermidis*, *Staphylococcus saprophyticus*, *Staphylococcus hyicus*, *Staphylococcus intermedius*, *Streptococcus pneumoniae*, and *Streptococcus pyogenes*. In yet a further aspect, the Gram positive bacteria is selected from *Bacillus anthracis*, *Bacillus subtilis*, *Enterococcus faecalis*, *Staphylococcus aureus*, *Streptococcus pneumoniae*, and *Streptococcus pyogenes*. In an even further aspect, the Gram positive bacteria is selected from vancomycin resistant *Enterococcus faecalis*, vancomycin resistant methicillin resistant *Enterococcus faecium*, *Staphylococcus aureus* (MRSA), methicillin resistant *Staphylococcus epidermidis* (MRSE), macrolide resistant *Streptococcus pneumoniae* (Mac-R SPN) or penicillin resistant *Streptococcus pneumonia* (PRSP).

In a further aspect, the present disclosure provides methods of treating an infectious disease such as a Gram negative bacterial infection. In a still further aspect, the Gram negative bacteria is selected from *Acinetobacter* sp., *Aeromonas* sp., *Burkholderia* sp., *Bordatella* sp., *Citrobacter* sp., *Chlamydia* sp., *Enterobacter* sp., *Escherichia* sp., *Francisella* sp., *Haemophilus* sp., *Klebsiella* sp., *Legionella* sp., *Moraxella* sp., *Neisseria* sp., *Proteus* sp., *Pseudomonas* sp., *Rickettsia* sp., *Salmonella* sp., *Shigella* sp., *Stenotrophomonas* sp., *Vibrio* sp., and *Yersinia* sp. In yet a further aspect, the Gram negative bacteria is selected from *Acinetobacter baumannii*, *Aeromonas hydrophila*, *Bordetella pertussis*, *Bordetella parapertussis*, *Bordetella bronchiseptica*, *Burkholderia cepacia*, *Citrobacter freundii*, *Chlamydia pneumoniae*, *Chlamydia trachomatis*, *Chlamydia psittaci*, *Enterobacter aerogenes*, *Enterobacter cloacae*, *Enterobacter sakazakii*, *Escherichia coli*, *Francisella tularensis*, *Haemophilus influenzae*, *Haemophilus aegypticus*, *Haemophilus ducreyi*, *Klebsiella edwardsii*, *Klebsiella pneumoniae*, *Legionella pneumophilia*, *Moraxella catarrhalis*, *Neisseria meningitidis*, *Neisseria gonorrhoeae*, *Proteus mirabilis*, *Proteus vulgaris*, *Pseudomonas aeruginosa*, *Rickettsia rickettsii*, *Rickettsia akari*, *Rickettsia conorrii*, *Rickettsia sibirica*, *Rickettsia australis*, *Rickettsia fells*, *Rickettsia japonica*, *Rickettsia africae*, *Rickettsia prowazekii*, *Rickettsia typhi*, *Salmonella enterica*, *Shigella boydii*, *Shigella dysenteriae*, *Shigella flexneri*, *Shigella sonnei*, *Stenotrophomonas maltophilia*, *Vibrio cholerae*, *Vibrio parahaemolyticus*, *Vibrio vulnificus*, *Vibrio fluvialis*, *Yersinia pestis*, *Yersinia enterocolitica*, or *Yersinia pseudotuberculosis*.

In a further aspect, the Gram negative bacteria is a multi-drug resistant Gram negative bacteria strain (MDR-GNB). In a still further aspect, the multi-drug resistant Gram negative bacteria strain (MDR-GNB) is resistant to at least one anti-microbial agent selected from amikacin, tobramycin, cefepime, ceftazidime, 1m1penem, meropenem, piperacillin-tazobactam, ciprofloxacin, levofloxacin, tigecycline, and polymyxin B. In yet a further aspect, the multi-drug resistant Gram negative bacteria strain (MDR-GNB) is selected from *Acinetobacter* sp., *Enterobacter* sp., *Klebsiella* sp., or *Pseudomonas* sp. In an even further aspect, the multi-drug resistant Gram negative bacteria strain (MDR-GNB) is selected from *Acinetobacter baumannii*, *Enterobacter aerogenes*, *Klebsiella pneumoniae*, or *Pseudomonas aeruginosa*. In a still further aspect, the multi-drug resistant Gram negative bacteria strain (MDR-GNB) is an *Enterobacter* sp.

In a further aspect, the present disclosure provides methods of treating an infectious disease selected from atypical pneumonia, bacterial meningitis, bronchitis, cholera, dental infection, dermatitis, diarrhea, diphtheria, dysentery, ear infection, endocarditis, gastritis, gastroenteritis, genital infection, genitourinary infection, infection associated with an indwelling device, intestinal infection, leprosy, listeriosis, lung infection, nosocomial infection, ocular infection, oral infection, otitis, osteo-articular infection, osteomyelitis, pharyngitis, papules, pharyngitis, pneumonia, pneumonia conjunctivitis, pruritius, pustules, pyoderma, pyothorax, respiratory infection, *salmonellosis*, septicemia, sexually transmitted disease, sinusitis, skin infection, skin and soft tissue infection ("SSTI"), soft tissue infection, tetanus, tuberculosis, typhus, ulcer, urinary tract infection, and wound infection. In a still further aspect, the infectious disease is selected from endocarditis, osteomyelitis, skin and soft tissue infection ("SSTI"), and infection associated with an indwelling device. In yet a further aspect, the infectious disease is endocarditis. In an even further aspect, the infectious disease is osteomyelitis. In a still further aspect, the infectious disease is an SSTI. In yet a further aspect, the SSTI is a complicated SSTI (cSSTI). In an even further aspect, the infectious disease is associated with an indwelling device.

In a further aspect, the present disclosure provides methods of treating an infectious disease such in a human subject comprising administering a disclosed compound or a disclosed pharmaceutical composition, and further comprising administering to the human subject a therapeutically effective amount of a second active agent. In a still further aspect, the second active agent comprises at least one antibacterial agent. In yet a further aspect, the antibacterial agent comprises a compound selected from amoxicillin, ampicillin, azithromycin, aztreonam, azlocillin, bacitracin, carbenicillin, cefaclor, cefadroxil, cefamandole, cefazolin, cephalexin, cefdinir, cefditorin, cefepime, cefixime, cefoperazone, cefotaxime, cefoxitin, cefpodoxime, cefprozil, ceftazidime, ceftibuten, ceftizoxime, ceftriaxone, cefuroxime, chloramphenicol, cilastin, ciprofloxacin, clarithromycin, clavulanic acid, clinafloxacin, clindamycin, clofazimine, cloxacillin, colistin, cycloserin, dalbavancin, dalfopristin, demeclocycline, dicloxacillin, dirithromycin, doxycycline, erythromycin, enrofloxacin, enoxacin, enviomycin, ertepenem, ethambutol, ethionmide, flucloxacillin, fosfomycin, furazolidone, gatifloxacin, gentamicin, imipenem, isoniazid, kanamycin, levofloxacin, linezolid, lomefloxacin, loracarbef, mafenide, moxifloxacin, meropenem, metronidazole, mezlocillin, minocycline, mupirocin, nafcillin, nalidixic acid, neomycin, netilmicin, nitrofurantoin, norfloxacin, ofloxacin, oritavancin, oxytetracycline, penicillin, piperacillin, platensimycin, polymixin B, pyrazinamide, quinupristin, retapamulin, rifabutin, rifampin, rifapentine, roxithromycin, sparfloxacin, spectinomycin, sulbactam, sulfacetamide, sulfamethizole, sulfamethoxazole, teicoplanin, telithromycin, telavancin, temafloxacin, tetracycline, thioacetazone, thioridazine, ticarcillin, tinidazole, tobramycin, torezolid, tosufloxacin, trimethoprim, troleandomycin, trovafloxacin, and vancomycin, or combinations thereof.

In a further aspect, the present disclosure provides methods of treating an infectious disease such in a human subject comprising administering a disclosed compound or a disclosed pharmaceutical composition, and further comprising administering to the human subject a therapeutically effective amount of an anti-tuberculosis agent. In a still further aspect, the antituberculosis agent is selected from amikacin, amoxicillin-clavulanic acid, bedaquiline, capreomycin, ciprofloxacin, clarithromycin, clofazimine, cycloserine, ethambutol, ethionamide, gatifloxacin, imipenem, isoniazid, kanamycin, levofloxacin, meropenem, moxifloxacin, ofloxacin, OPC-7683, para-aminosalicylic acid, pretomanid, pyrazinamide, rifampin, rifapentine, rifabutin, SQ109, streptomycin, sudoterb, terizidone, thiacetazone, viomycin, and combinations thereof. In a yet further aspect, the anti-tuberculosis agent is an aminoglycoside antibiotic, such as kanamycin A, amikacin, tobramycin, dibekacin, gentamicin, sisomicin, netilmicin, neomycin B, neomycin C, paromomycin and streptomycin. In an even further aspect, the anti-tuberculosis agent is a fluoroquinolone, such as moxifloxacin, levofloxacin, sparfloxacin, nalidixic acid, ciprofloxacin, cinoxacin, oxolinic acid, piromidic acid, pipemidic acid, rosoxacin, enoxacin, fleroxacin, lomefloxacin, nadifloxacin, norfloxacin, ofloxacin, perfloxacin, rufloxacin, balofloxacin, grepafloxacin, pazufloxacin, temafloxacin, tosufloxacin, clinafloxacin, gatlifloxacin, sitafloxacin, prulifloxacin, delafloxacin, JNJ-Q2, nemofloxacin, danofloxacin, difloxacin, enrofloxacin, ibafloxacin, marbofloxacin, orbifloxacin, sarafloxacin and trovafloxacin. In a still further aspect, the anti-tuberculosis agent is a nitroimidazole antibiotic, such as metronidazole, tinidazole and nimorazole.

In a further aspect, the present disclosure provides methods of treating an infectious disease such in a human subject comprising administering a disclosed compound or a disclosed pharmaceutical composition, and further comprising administering to the human subject a therapeutically effective amount of an immunomodulatory agent. In a still further aspect, the immunomodulatory agent is a cytokine, an interleukin, a chemokine, or combinations thereof. In a yet further aspect, the immunomodulatory agent is selected from IL-2, IL-7 and IL-12, IFN-α, IFN-β, IFN-ε, IFN-κ, IFN-ω, IFN-γ, IFN-γ 1 b, CCL3, CCL26, CXCL7, and combinations thereof.

In a further aspect, the administering is co-administering of the disclosed compound and the antibacterial agent. In a still further aspect, the co-administration is administration in a substantially simultaneous manner of the disclosed compound and the antibacterial agent. In yet a further aspect, the co-administration is administration in a substantially sequential manner of the disclosed compound and the antibacterial agent. In a further aspect, the administration in a substantially simultaneous manner comprises a single dose form containing a fixed ratio of the compound and the antibacterial agent. In a still further aspect, the single dose form is a capsule or a tablet. In yet a further aspect, the single dose form is an ampule for a single intravenous administration.

In various aspects, the disclosed APBA therapeutic peptides can have a mechanism of antimicrobial action and/or may bind to and/or inhibit one or more bacterial target molecules or macromolecular complexes containing a bacterial target molecule. Mechanisms of action may include inhibiting or interfering with a biological or biochemical pathway of the bacterium. Exemplary pathways include, but are not limited to, protein synthesis, cell wall synthesis, DNA replication, transcription, and cell division. It will be appreciated that biological and biochemical pathways are not mutually exclusive and that some biological or biochemical pathways may be considered to be subsets or sub-pathways of other biological or biochemical pathways. Mechanisms of action include, but are not limited to, inhibiting protein synthesis (e.g., by binding ribosomal RNA or proteins, blocking tRNA binding to the ribosome-mRNA complex, inhibiting peptidyl transferase), inhibiting or interfering with synthesis of a cell wall component (e.g., inhibition of peptidoglycan synthesis, disruption of peptidoglycan cross-linkage, disruption of movement of peptidoglycan precursors, disruption of mycolic acid or arabinoglycan synthesis), cell membrane disruption, inhibiting or interfering with nucleic acid synthesis of processing, acting as "antimetabolites" and either inhibiting an essential bacterial enzyme or competing with a substrate of an essential bacterial enzyme, inhibiting or interfering with cell division.

Molecules, or macromolecular complexes containing them, that may be targets for antibiotics include, but are not limited to, peptidoglycans, penicillin binding proteins, lipopolysaccharides, ribosomes or ribosomal subunits or RNA or protein components thereof (23 S rRNA, 16S rRNA, proteins of the 30S or SOS subunit), DNA-dependent DNA polymerase, DNA-dependent RNA polymerase, microbial type I topoisomerase, microbial type II topoisomerase (e.g., topoisomerase IV or gyrase), enzymes involved in cell division such as FtsZ, etc.

In various aspects, the disclosed APBA therapeutic peptides inhibit bacterial protein synthesis. The bacterial species may be of any one or more types, e.g., gram-negative bacteria, gram-positive bacteria, atypical bacteria, and/or acid fast bacteria. Suitable organisms can include, but are not limited to members of the following genuses: *Actinomyces, Staphylococcus, Streptococcus, Enterococcus, Erysipelothrix, Neisseria, Branhamella, Listeria, Bacillus, Corynbacterium, Erysipelothrix, Gardnerella, Mycobacterium, Nocardia, Enterobacteriaceae, Escherichia, Salmo-* nella, *Shigella, Yersinia, Enterobacter, Klebsiella, Citrobacter, Serratia, Providencia, Proteus, Morganella, Edwardsiella, Erwinia, Vibrio, Aeromonas, Helicobacter, Campylobacter, Eikenella, Pasteurella, Pseudomonas, Burkholderia, Stenotrophomonas, Acinetobacter, Ralstonia, Alcaligenes, Moraxella, Mycoplasma, Legionella, Francisella, Brucella, Haemophilus, Bordetella, Clostridium, Bacteroides, Porphyromonas, Prevotella, Fusobacterium, Borrelia, Chlamydia, Rickettsia, Ehrlichia, Bartonella, Trichomonas*, and *Treponema*.

In various aspects of the disclosure the bacteria are species that are causative agents of disease in humans and/or animals. Examples include, but are not limited to, *Acinetobacter baumannii, Aeromonas hydrophila, Bacillus anthracis, Bacillus anthracis sterne, Bacillus subtilis, Burkholderia cepacia, Escherichia coli, Enterobacter cloacae, Enterococcus faecalis, Francisella tularensis, Campylobacter jejuni, Haemophilus influenzae, Klebsiella pneumoniae, Klebsiella oxytoca, Legionella pneumophila, Pasteurella multocida, Proteus mirabilis, Proteus vulgaris, Mycobacterium tuberculosis, Morganella morganii, Helicobacter pylori, Neisseria meningitides, Neisseria gonorrhoeae, Chlamydia trachomatis, Pseudomonas aeruginosa, Salmonella enterica, Salmonella typhimurium, Staphylococcus aureus, Staphylococcus epidermidis, Streptococcus pneumoniae, Streptococcus pyogenes, Strenotrophomonas maltophilia, Streptococcus agalactiae*, and *Yersinia pestis*.

Antifungal Uses for APBA Peptides

In various aspects, the present disclosure provides methods of treating an infectious disease comprising administration of a therapeutically effective amount of a disclosed APBA therapeutic peptide or a disclosed pharmaceutical composition to a subject in need thereof. It is understood that reference to a disclosed APBA therapeutic peptide is inclusive of the disclosed APBA therapeutic peptide, as well as pharmaceutically acceptable salt, hydrate, solvate, or polymorph forms thereof and a disclosed APBA therapeutic peptide further comprising an antifungal residue and/or a detectable label residue; and reference to a disclosed pharmaceutical composition is inclusive of a pharmaceutical composition comprising a disclosed APBA therapeutic peptide or pharmaceutically acceptable salt, hydrate, solvate, or polymorph forms of a disclosed APBA therapeutic peptide, and pharmaceutical compositions comprising a disclosed APBA therapeutic peptide further comprising an antifungal residue and/or a detectable label residue.

It is understood that treating an infectious disease is inclusive of treating, preventing, ameliorating, controlling or reducing the risk of a variety of fungal infections, including an infection associated with *Candida* sp., *Aspergillus* sp., *Cryptococcus neoformans, Rhizopus* sp., *Absidia* sp., *Mucor* sp., *Malassezia furfur, Trichosporon* sp., *Fusarium* sp., *Pseudallescheria Scedospoium* sp., *Alternaria* sp., *Blastomyces dermatitidis, Histoplasma capsulatum, Coccidiodis immitis, Paracoccidioidis brasiliensis*, or *Penicillium marneffei*, wherein the patient or subject would benefit from an antifungal agent. For example, a treatment can include binding a disclosed APBA therapeutic peptide, optionally further comprising an antifungal residue and/or a detectable label residue, to a target fungus or fungal protein in a subject infected with said target fungus, and wherein the disclosed APBA therapeutic peptide via binding and/or binding with delivery of an antifungal residue and/or a detectable label residue to the target fungus or fungal protein. In one aspect, provided is a method of treating or preventing a fungal infection in a subject comprising the step of administering to the subject at least one disclosed APBA therapeutic peptide or at least one disclosed pharmaceutical composition in a dosage and amount effective to treat the disorder in the subject.

Also provided is a method for the treatment of one or more disorders associated with infection by a target fungus wherein inhibiting binding of a disclosed APBA therapeutic peptide can sterilize or decrease the presence of the pathogenic fungus in a subject comprising the step of administering to the subject at least one disclosed APBA therapeutic peptide or at least one disclosed pharmaceutical composition in a dosage and amount effective to treat the disorder in the subject.

Also provided is a method for the treatment of a fungal infection in a vertebrate animal comprising the step of administering to the mammal at least one disclosed compound, composition, or medicament. In some aspects, the vertebrate animal is a mammal.

In a further aspect, the vertebrate animal is a fish, a bird, or a mammal. In a still further aspect, the vertebrate animal is a livestock animal. In yet a further aspect, the vertebrate animal is a companion animal. In an even further aspect, the vertebrate animal is a farm animal. In a still further aspect, the vertebrate animal is a zoo animal. In yet a further aspect, the vertebrate animal is a laboratory animal. In an even further aspect, the vertebrate animal is an aquaculture fish. In a still further aspect, the vertebrate animal is selected from *Bison* sp., *Bos* sp., *Canis* sp., *Capra* sp., *Equus* sp., *Felis* sp., *Gallus* sp., *Lama* sp., *Meleagris* sp., *Oryctolagus* sp., *Ovis* sp., and *Sus* sp.

In a further aspect, the vertebrate animal has been diagnosed with a need for treatment of the infectious fungal disease prior to the administering step.

In a further aspect, the disclosure relates to a method for the treatment of an infectious fungal disease in a vertebrate animal, further comprising the step of identifying a vertebrate animal in need of treatment of the infectious fungal disease.

In a further aspect, administering comprises mixing an effective amount of a disclosed APBA therapeutic peptide with the food of the vertebrate animal. In a still further aspect, administering comprises administering enterally an effective amount of the disclosed APBA therapeutic peptide with the food of the vertebrate animal. In yet a further aspect, administering comprises administering an oral bolus of an effective amount of the disclosed APBA therapeutic peptide with the food of the vertebrate animal.

In various aspects, administering to a vertebrate animal comprises intravenous administration or parenteral administration to the vertebrate animal. In a further aspect, the infectious disease treated in the vertebrate animal is selected from candidiasis, cryptococcosis, aspergillosis, coccidioidomycosis, histoplasmosis, blastomycosis, a fungal nail infection, ringworm, athlete's foot, or *pneumocystis* pneumonia.

In a further aspect, the disclosure relates to a method for the treatment of an infectious disease in a vertebrate animal, further comprising administering to the vertebrate animal a therapeutically effective amount of second active agent. In a still further aspect, the second active agent is an antifungal agent. In yet a further aspect, the antifungal agent is clotrimazole, econazole, miconazole, terbinafine, fluconazole, ketoconazole, amphotericin B, isavuconazole, itraconazole, posaconazole, voriconazole, anidulafungin, caspofungin, micafungin, flucytosine, or a combination thereof.

The disclosed APBA therapeutic peptides are further useful in a method for the prevention, treatment, control, amelioration, or reduction of risk of the fungal infections noted herein. The disclosed APBA therapeutic peptides are further useful in a method for the prevention, treatment, control, amelioration, or reduction of risk of the aforementioned fungal infections in combination with other agents.

In one aspect, the disclosed APBA therapeutic peptides can be used in combination with one or more other drugs in the treatment, prevention, control, amelioration, or reduction of risk of fungal infections for which disclosed APBA therapeutic peptides or the other drugs can have utility, where the combination of the drugs together are safer or more effective than either drug alone. Such other drug(s) can be administered, by a route and in an amount commonly used therefor, contemporaneously or sequentially with a compound of the present disclosure. When a compound of the present disclosure is used contemporaneously with one or more other drugs, a pharmaceutical composition in unit dosage form containing such other drugs and a disclosed compound is preferred. However, the combination therapy can also include therapies in which a disclosed compound and one or more other drugs are administered on different overlapping schedules. It is also contemplated that when used in combination with one or more other active ingredients, the disclosed APBA therapeutic peptides and the other active ingredients can be used in lower doses than when each is used singly. Accordingly, the pharmaceutical compositions include those that contain one or more other active ingredients, in addition to a compound of the present disclosure.

The above combinations include combinations of a disclosed compound not only with one other active compound, but also with two or more other active compounds. Likewise, disclosed APBA therapeutic peptides can be used in combination with other drugs that are used in the prevention, treatment, control, amelioration, or reduction of risk of the fungal infections for which disclosed APBA therapeutic peptides are useful. Such other drugs can be administered, by a route and in an amount commonly used therefor, contemporaneously or sequentially with a compound of the present disclosure. When a compound of the present disclosure is used contemporaneously with one or more other drugs, a pharmaceutical composition containing such other drugs in addition to a disclosed compound is preferred. Accordingly, the pharmaceutical compositions include those that also contain one or more other active ingredients, in addition to a compound of the present disclosure.

The weight ratio of a disclosed compound to the second active ingredient can be varied and will depend upon the effective dose of each ingredient. Generally, an effective dose of each will be used. Thus, for example, when a compound of the present disclosure is combined with another agent, the weight ratio of a disclosed compound to the other agent will generally range from about 1000:1 to about 1:1000, preferably about 200:1 to about 1:200. Combinations of a compound of the present disclosure and other active ingredients will generally also be within the aforementioned range, but in each case, an effective dose of each active ingredient should be used.

In such combinations a disclosed compound and other active agents can be administered separately or in conjunction. In addition, the administration of one element can be prior to, concurrently with, or subsequent to the administration of other agent(s). Accordingly, the disclosed APBA therapeutic peptides can be used alone or in combination with other agents which are known to be beneficial in the subject indications or other drugs that affect receptors or enzymes that either increase the efficacy, safety, convenience, or reduce unwanted side effects or toxicity of the other agents. The disclosed APBA therapeutic peptide and the other agent can be coadministered, either in concomitant therapy or in a fixed combination.

In one aspect, the compound can be employed in combination with antifungal agents, and combinations thereof, and the like, or the subject compound can be administered in conjunction with the use of physical methods such as with debridement of a wound or infected tissue.

In the treatment of an infectious disease condition, an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level can be about to 250 mg/kg per day, about 0.05 to 100 mg/kg per day, or about 0.1 to 50 mg/kg per day. Within this range the dosage can be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10, 15, 20, 25, 50, 75, 100, 150,200, 250, 300, 400, 500, 600, 750, 800, 900, and 1000 milligrams of the active ingredient for the symptomatic adjustment of the dosage to the patient to be treated. The compounds can be administered on a regimen of 1 to 4 times per day, preferably once or twice per day. This dosage regimen can be adjusted to provide the optimal therapeutic response. It will be understood, however, that the specific dose level and frequency of dosage for any particular patient can be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Thus, in one aspect, the disclosure relates to methods for treating a fungal infection in at least one cell, comprising the step of contacting the at least one cell with at least one compound of the disclosure, in an amount effective to alter the response in the at least one cell. In a further aspect, the cell is mammalian, for example human. In a further aspect, the cell has been isolated from a subject prior to the contacting step. In a further aspect, contacting is via administration to a subject.

Infectious diseases treatable by the presently disclosed APBA therapeutic peptides can be caused by a variety of fungi. Exemplary fungal infections that can be treated by the method of the presently disclosed APBA therapeutic peptides include, but are not limited to, infections caused by *Aspergillus fumigatus, Blastomyces dermatitidis, Candida albicans, Candida glabrata, Candida tropicalis, Coccidioides immitis, Coccidioides posadasii, Cryptococcus neoformans, Cryptococcus gattii, Histoplasma capsulatum*, a *Rhizopus* species, a *Rhizomucor* species, a *Mucor* species, *Paracoccidioides brasiliensis*, a *Bipolaris* species, a *Cladophialophora* species, a *Cladosporium* species, an *Exophiala* species, a *Fonsecaea* species, a *Phialophora* species, an *Ochronosis* species, a *Rhinocladiella* species, a *Wangiella* species, *Sporothrix schenckii, Blastoschizomyces capitatus, Trichosporon ovoides, Trichosporon inkin, Trichosporon mucoides, Trichosporon asteroids, Trichosporon cutaneum, Malassezia furfur, Talaromyces mameffei*, a *Fusarium* species, or *Scedosporium apiospermum*.

Antiviral Uses for APBA Peptides

In various aspects, the present disclosure provides methods of treating an infectious disease comprising administration of a therapeutically effective amount of a disclosed APBA therapeutic peptide or a disclosed pharmaceutical composition to a subject in need thereof. It is understood that reference to a disclosed APBA therapeutic peptide is inclusive of the disclosed APBA therapeutic peptide, as well as pharmaceutically acceptable salt, hydrate, solvate, or polymorph forms thereof and a disclosed APBA therapeutic peptide further comprising an antiviral residue and/or a detectable label residue; and reference to a disclosed pharmaceutical composition is inclusive of a pharmaceutical composition comprising a disclosed APBA therapeutic peptide or pharmaceutically acceptable salt, hydrate, solvate, or polymorph forms of a disclosed APBA therapeutic peptide, and pharmaceutical compositions comprising a disclosed APBA therapeutic peptide further comprising an antiviral residue and/or a detectable label residue.

It is understood that treating an infectious disease is inclusive of treating, preventing, ameliorating, controlling or reducing the risk of a variety of viral infections, including an infection associated with an influenza virus, a common cold virus, a respiratory syncytial virus, an adenovirus, a parainfluenza virus, a sever acute respiratory syndrome virus, a norovirus, a rotavirus, an astrovirus, measles, rubella, roseola, smallpox, chicken pox or shingles, fifth disease, chikungunya virus, hepatitis A, B, C, D, or E, a herpes virus, a papillomavirus, Molluscum contagiosum, Ebola virus, Lassa fever, dengue fever, yellow fever, a Marburg virus, a poliovirus, viral meningitis, viral encephalitis, human immunodeficiency virus, rabies, or a parvovirus, wherein the patient or subject would benefit from an antiviral agent. For example, a treatment can include binding a disclosed APBA therapeutic peptide, optionally further comprising an antiviral residue and/or a detectable label residue, to a target virus or host cell infected by a virus in a subject infected with said target virus, and wherein the disclosed APBA therapeutic peptide via binding and/or binding with delivery of an antiviral residue and/or a detectable label residue to the target virus. In one aspect, provided is a method of treating or preventing a viral infection in a subject comprising the step of administering to the subject at least one disclosed APBA therapeutic peptide or at least one disclosed pharmaceutical composition in a dosage and amount effective to treat the disorder in the subject.

Also provided is a method for the treatment of one or more disorders associated with infection by a target virus wherein inhibiting binding of a disclosed APBA therapeutic peptide can sterilize or decrease the presence of the pathogenic virus in a subject comprising the step of administering to the subject at least one disclosed APBA therapeutic peptide or at least one disclosed pharmaceutical composition in a dosage and amount effective to treat the disorder in the subject.

Also provided is a method for the treatment of a viral infection in a vertebrate animal comprising the step of administering to the mammal at least one disclosed compound, composition, or medicament. In some aspects, the vertebrate animal is a mammal.

In a further aspect, the vertebrate animal is a fish, a bird, or a mammal. In a still further aspect, the vertebrate animal is a livestock animal. In yet a further aspect, the vertebrate animal is a companion animal. In an even further aspect, the vertebrate animal is a farm animal. In a still further aspect, the vertebrate animal is a zoo animal. In yet a further aspect, the vertebrate animal is a laboratory animal. In an even further aspect, the vertebrate animal is an aquaculture fish. In a still further aspect, the vertebrate animal is selected from *Bison* sp., *Bos* sp., *Canis* sp., *Capra* sp., *Equus* sp., *Felis* sp., *Gallus* sp., *Lama* sp., *Meleagris* sp., *Oryctolagus* sp., *Ovis* sp., and *Sus* sp.

In a further aspect, the vertebrate animal has been diagnosed with a need for treatment of the infectious disease prior to the administering step.

In a further aspect, the disclosure relates to a method for the treatment of an infectious viral disease in a vertebrate animal, further comprising the step of identifying a vertebrate animal in need of treatment of the infectious viral disease.

In a further aspect, administering comprises mixing an effective amount of a disclosed APBA therapeutic peptide with the food of the vertebrate animal. In a still further aspect, administering comprises administering enterally an effective amount of the disclosed APBA therapeutic peptide with the food of the vertebrate animal. In yet a further aspect, administering comprises administering an oral bolus of an effective amount of the disclosed APBA therapeutic peptide with the food of the vertebrate animal.

In various aspects, administering to a vertebrate animal comprises intravenous administration or parenteral administration to the vertebrate animal. In a further aspect, the infectious disease treated in the vertebrate animal is selected from dental infection, dermatitis, diarrhea, ear infection, gastritis, gastroenteritis, genitourinary infection, intestinal infection, lung infection, ocular infection, oral infection, otitis, osteo-articular infection, pharyngitis, papules, pneumonia conjunctivitis, pruritus, pustules, pyoderma, pyothorax, respiratory infection, *salmonellosis*, septicemia, skin infection, soft tissue infection, ulcer, urinary tract infection, and wound infection.

In a further aspect, the disclosure relates to a method for the treatment of an infectious disease in a vertebrate animal, further comprising administering to the vertebrate animal a therapeutically effective amount of second active agent. In a still further aspect, the second active agent is an antiviral agent. In yet a further aspect, the antiviral agent is abacavir, acyclovir, adefovir, amatadine, ampligen, amprenavir, arbidol umifenovir, atazanavir, atripla, baloxavir marboxil, biktarvy, boceprevir, bulevirtide, cidofovir, cobicistat, combivir, daclatasvir, darunavir, delavirdine, descovy, didanosine, docosanol, dolutegravir, doravirine, edoxudine, efavirenz, elvitegravir, emtricitabine, enfuvirtide, entecavir, etavirine, famciclovir, fomivirsen, fosamprenavir, foscarnet, ganciclovir, ibacitabine, ibalizumab, idoxuridine, imiquimod, imunovir, indinavir, lamivudine, letermovir, lopinavir, liviride, maraviroc, methisazone, moroxydine, nelfinavir, nevirapine, nexavir, nitazoxanide, norvir, oseltamivir, penciclovir, peramivir, pleconaril, podophyllotoxin, raltegravir, remdesivir, ribavirin, rilpivirine, rimantadine, ritonavir, saquinavir, simeprevir, sofosbuvir, stavudine, taribavirin, telaprevir, telbivudine, tenofovir alafenamide, tenofovir disoproxil, tenofovir, tipranavir, trifluridine, trizvir, tromantadine, truvada, umefenovir, valaciclovir, valganciclovir, vicriviroc, vidarabine, zalcitabine, zanamivir, or zidovudine.

The disclosed APBA therapeutic peptides are further useful in a method for the prevention, treatment, control, amelioration, or reduction of risk of the viral infections noted herein. The disclosed APBA therapeutic peptides are further useful in a method for the prevention, treatment, control, amelioration, or reduction of risk of the aforementioned viral infections in combination with other agents.

In one aspect, the disclosed APBA therapeutic peptides can be used in combination with one or more other drugs in the treatment, prevention, control, amelioration, or reduction of risk of viral infections for which disclosed APBA therapeutic peptides or the other drugs can have utility, where the combination of the drugs together are safer or more effective than either drug alone. Such other drug(s) can be administered, by a route and in an amount commonly used therefor, contemporaneously or sequentially with a compound of the present disclosure. When a compound of the present disclosure is used contemporaneously with one or more other drugs, a pharmaceutical composition in unit dosage form containing such other drugs and a disclosed compound is preferred. However, the combination therapy can also include therapies in which a disclosed compound and one or more other drugs are administered on different overlapping schedules. It is also contemplated that when used in combination with one or more other active ingredients, the disclosed APBA therapeutic peptides and the other active ingredients can be used in lower doses than when each is used singly. Accordingly, the pharmaceutical compositions include those that contain one or more other active ingredients, in addition to a compound of the present disclosure.

The above combinations include combinations of a disclosed compound not only with one other active compound, but also with two or more other active compounds. Likewise, disclosed APBA therapeutic peptides can be used in combination with other drugs that are used in the prevention, treatment, control, amelioration, or reduction of risk of the viral infections for which disclosed APBA therapeutic peptides are useful. Such other drugs can be administered, by a route and in an amount commonly used therefor, contemporaneously or sequentially with a compound of the present disclosure. When a compound of the present disclosure is used contemporaneously with one or more other drugs, a pharmaceutical composition containing such other drugs in addition to a disclosed compound is preferred. Accordingly, the pharmaceutical compositions include those that also contain one or more other active ingredients, in addition to a compound of the present disclosure.

The weight ratio of a disclosed compound to the second active ingredient can be varied and will depend upon the effective dose of each ingredient. Generally, an effective dose of each will be used. Thus, for example, when a compound of the present disclosure is combined with another agent, the weight ratio of a disclosed compound to the other agent will generally range from about 1000:1 to about 1:1000, preferably about 200:1 to about 1:200. Combinations of a compound of the present disclosure and other active ingredients will generally also be within the aforementioned range, but in each case, an effective dose of each active ingredient should be used.

In such combinations a disclosed compound and other active agents can be administered separately or in conjunction. In addition, the administration of one element can be prior to, concurrently with, or subsequent to the administration of other agent(s). Accordingly, the disclosed APBA therapeutic peptides can be used alone or in combination with other agents which are known to be beneficial in the subject indications or other drugs that affect receptors or enzymes that either increase the efficacy, safety, convenience, or reduce unwanted side effects or toxicity of the other agents. The disclosed APBA therapeutic peptide and the other agent can be coadministered, either in concomitant therapy or in a fixed combination.

In one aspect, the compound can be employed in combination with antiviral agents, and combinations thereof, and the like, or the subject compound can be administered in conjunction with the use of physical methods such as with debridement of a wound or infected tissue.

In the treatment of an infectious disease condition, an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level can be about to 250 mg/kg per day, about 0.05 to 100 mg/kg per day, or about 0.1 to 50 mg/kg per day. Within this range the dosage can be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10, 15, 20, 25, 50, 75, 100, 150,200, 250, 300, 400, 500, 600, 750, 800, 900, and 1000 milligrams of the active ingredient for the symptomatic adjustment of the dosage to the patient to be treated. The compounds can be administered on a regimen of 1 to 4 times per day, preferably once or twice per day. This dosage regimen can be adjusted to provide the optimal therapeutic response. It will be understood, however, that the specific dose level and frequency of dosage for any particular patient can be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Thus, in one aspect, the disclosure relates to methods for treating a viral infection in at least one cell, comprising the step of contacting the at least one cell with at least one compound of the disclosure, in an amount effective to alter the response in the at least one cell. In a further aspect, the cell is mammalian, for example human. In a further aspect, the cell has been isolated from a subject prior to the contacting step. In a further aspect, contacting is via administration to a subject.

Infectious diseases treatable by the presently disclosed APBA therapeutic peptides can be caused by a variety of viruses. Exemplary viral infections that can be treated by the method of the presently disclosed APBA therapeutic peptides include, but are not limited to, infections caused by human immunodeficiency virus, Junin virus, BK virus, Machupo mammarenavirus, Brazilian mammarenavirus, Varicella zoster virus, an alphavirus, a coltivirus, severe acute respiratory syndrome coronavirus, severe acute respiratory syndrome coronavirus 2, a rhinovirus, a coronavirus, dengue virus, cytomegalovirus, West Nile virus, yellow fever virus, tick-borne encephalitis virus, another flavivirus, an Ebola virus, a parvovirus, human herpesvirus 6, human betaherpesvirus 6, human betaherpesvirus 7, Sin Nombre orthohantavirus, Heartland bandavirus, Hendra virus, Hepatitis A virus, Hepatitis B virus, Hepatitis C virus, Hepatitis D virus, Hepatitis E virus, herpes simplex virus 1, herpes simplex virus 2, human bocavirus, human metapneumovirus, human papillomavirus, a human parainfluenza virus, Epstein-Barr virus, an influenza virus, Lassa mammarenavirus, lymphocytic choriomeningitis mammarenavirus, a Marburg virus, measles morbillivirus, Middle East respiratory syndrome-related coronavirus, molluscum contagiosum virus, monkeypox virus, mumps orthorubulavirus, Nipah henipavirus, norovirus, poliovirus, human polyomavirus, rabies virus, human orthopneumovirus, Rift Valley fever virus, a rotavirus, rubella virus, smallpox, Guanarito mammarenavirus, or Zika virus.

Anticancer Uses for APBA Peptides

In various aspects, the present disclosure provides methods of treating cancer comprising administration of a therapeutically effective amount of a disclosed APBA therapeutic peptide or a disclosed pharmaceutical composition to a subject in need thereof. It is understood that reference to a disclosed APBA therapeutic peptide is inclusive of the disclosed APBA therapeutic peptide, as well as pharmaceutically acceptable salt, hydrate, solvate, or polymorph forms thereof and a disclosed APBA therapeutic peptide further comprising an anticancer residue and/or a detectable label residue; and reference to a disclosed pharmaceutical composition is inclusive of a pharmaceutical composition comprising a disclosed APBA therapeutic peptide or pharmaceutically acceptable salt, hydrate, solvate, or polymorph forms of a disclosed APBA therapeutic peptide, and pharmaceutical compositions comprising a disclosed APBA therapeutic peptide further comprising an anticancer residue and/or a detectable label residue.

It is understood that treating cancer is inclusive of treating, preventing, ameliorating, controlling or reducing the risk of a variety of cancers, including, but not limited to, non-Hodgkins lymphoma, neuroblastoma, sarcoma, metastatic brain cancers, ovarian cancer, prostate cancer, breast cancers including triple-negative breast cancer, lymphoma, non-small cell lung carcinoma, gastric cancer, gastroesophageal junction adenocarcinoma, hematological cancers, melanoma, squamous cell carcinoma, Hodgkin's lymphoma, anaplastic large-cell lymphoma, pancreatic cancer, acute lymphoblastic leukemia, acute myeloid leukemia, hepatocellular carcinoma, colorectal cancer, angiosarcoma, head and neck cancer, ovarian cancer, solid tumors, multiple myeloma, glioblastoma, testicular cancer, B-cell malignancies, urothelial cancer, chronic lymphocytic leukemia, adenocortical carcinoma, acute myelogenous leukemia, clear cell renal cell carcinoma, chronic myelomonocytic leukemia, juvenile myelomonocytic leukemia, small cell lung carcinoma, hairy cell leukemia, renal cell carcinoma, nasopharyngeal cancer, glioma, chronic lymphatic leukemia, diffuse large B-cell lymphoma, gall bladder cancer, thyroid tumor, bone cancer, cervical cancer, uterine cancer, endometrial cancer, vulvar cancer, bladder cancer, colon cancer, colorectal cancer, pancreatic cancer, neuronal cancers, mesothelioma, cholangiocarcinoma, small bowel adenocarcinoma, pediatric malignancies, epidermoid carcinoma, cancer of the pleural or peritoneal membranes, or another cancer. For example, a treatment can include binding a disclosed APBA therapeutic peptide, optionally further comprising an anticancer residue and/or a detectable label residue, to a target bacteria in a subject diagnosed with said cancer, and wherein the disclosed APBA therapeutic peptide via binding and/or binding with delivery of an anticancer residue and/or a detectable label residue to the cancer. In one aspect, provided is a method of treating or preventing a cancer in a subject comprising the step of administering to the subject at least one disclosed APBA therapeutic peptide or at least one disclosed pharmaceutical composition in a dosage and amount effective to treat the cancer in the subject.

Also provided is a method for the treatment of one or more tumors associated with cancer wherein inhibiting binding of a disclosed APBA therapeutic peptide can kill or decrease the presence of the tumors in a subject comprising the step of administering to the subject at least one disclosed APBA therapeutic peptide or at least one disclosed pharmaceutical composition in a dosage and amount effective to treat the cancer in the subject.

Also provided is a method for the treatment of a cancer in a vertebrate animal comprising the step of administering to the mammal at least one disclosed compound, composition, or medicament. In some aspects, the vertebrate animal is a mammal.

In a further aspect, the vertebrate animal is a fish, a bird, or a mammal. In a still further aspect, the vertebrate animal is a livestock animal. In yet a further aspect, the vertebrate animal is a companion animal. In an even further aspect, the vertebrate animal is a farm animal. In a still further aspect, the vertebrate animal is a zoo animal. In yet a further aspect, the vertebrate animal is a laboratory animal. In an even further aspect, the vertebrate animal is an aquaculture fish. In a still further aspect, the vertebrate animal is selected from *Bison* sp., *Bos* sp., *Canis* sp., *Capra* sp., *Equus* sp., *Felis* sp., *Gallus* sp., *Lama* sp., *Meleagris* sp., *Oryctolagus* sp., *Ovis* sp., and *Sus* sp.

In a further aspect, the vertebrate animal has been diagnosed with a need for treatment of the cancer prior to the administering step.

In a further aspect, the disclosure relates to a method for the treatment of a cancer in a vertebrate animal, further comprising the step of identifying a vertebrate animal in need of treatment of the cancer.

In a further aspect, administering comprises mixing an effective amount of a disclosed APBA therapeutic peptide with the food of the vertebrate animal. In a still further aspect, administering comprises administering enterally an effective amount of the disclosed APBA therapeutic peptide with the food of the vertebrate animal. In yet a further aspect, administering comprises administering an oral bolus of an effective amount of the disclosed APBA therapeutic peptide with the food of the vertebrate animal.

In various aspects, administering to a vertebrate animal comprises intravenous administration or parenteral administration to the vertebrate animal. In a further aspect, the cancer treated in the vertebrate animal is selected from non-Hodgkins lymphoma, neuroblastoma, sarcoma, metastatic brain cancers, ovarian cancer, prostate cancer, breast cancers including triple-negative breast cancer, lymphoma, non-small cell lung carcinoma, gastric cancer, gastroesophageal junction adenocarcinoma, hematological cancers, melanoma, squamous cell carcinoma, Hodgkin's lymphoma, anaplastic large-cell lymphoma, pancreatic cancer, acute lymphoblastic leukemia, acute myeloid leukemia, hepatocellular carcinoma, colorectal cancer, angiosarcoma, head and neck cancer, ovarian cancer, solid tumors, multiple myeloma, glioblastoma, testicular cancer, B-cell malignancies, urothelial cancer, chronic lymphocytic leukemia, adenocortical carcinoma, acute myelogenous leukemia, clear cell renal cell carcinoma, chronic myelomonocytic leukemia, juvenile myelomonocytic leukemia, small cell lung carcinoma, hairy cell leukemia, renal cell carcinoma, nasopharyngeal cancer, glioma, chronic lymphatic leukemia, diffuse large B-cell lymphoma, gall bladder cancer, thyroid tumor, bone cancer, cervical cancer, uterine cancer, endometrial cancer, vulvar cancer, bladder cancer, colon cancer, colorectal cancer, pancreatic cancer, neuronal cancers, mesothelioma, cholangiocarcinoma, small bowel adenocarcinoma, pediatric malignancies, epidermoid carcinoma, cancer of the pleural or peritoneal membranes, or another cancer.

In a further aspect, the disclosure relates to a method for the treatment of a cancer in a vertebrate animal, further comprising administering to the vertebrate animal a therapeutically effective amount of second active agent. In a still further aspect, the second active agent is an anticancer agent. In yet a further aspect, the anticancer agent is paclitaxel, doxorubicin, gemcitabine, cisplatin, methotrexate, 5-fluorouricil, betulinic acid, amphotericin B, diazepam, nystatin, propofol, testosterone, docetaxel, a maytansinoid, a PD-1 inhibitor, a PDL1 inhibitor, a protein kinase inhibitor, a P-glycoprotein inhibitor, an autophage inhibitor, a PARP inhibitor, an aromatase inhibitor, a monoclonal antibody, a photosensitizer, a radiosensitizer, an interleukin, an antiandrogen, ansamitocin, mertansine (DM1), ravtansine, ramucirumab, 3F8, 8H9, Abagovomab, Abituzumab, Adalimumab, Afutuzumab, Alacizumab pegol, Amatuximab, Anatumomab mafenatox, Andecaliximab, Anetumab ravtansine, Apolizumab, Arcitumomab, Ascrinvacumab, Atezolizumab, Avelumab, Azintuxizumab vedotin, Bavituximab, BCD-100, Belantamab mafodotin, Belimumab, Bemantuzumab, Besilesomab, Bevacizumab, Bivatuzumab mertansine, Brentuximab 5 vedotin, Brontictuzumab, Cabiralizumab, Camidanlumab tesirine, Camrelizumab, Cantuzumab mertansine, Cantuzumab ravtansine, Carotuximab, Cantumaxomab, cBR96-doxorubicin immunoconjugate, Cemiplimab, Cergutuzumab amunaleukin, Cetrelimab, Cetuximab, Cibisatamab, Citatuzumab bogatox, Cixutumumab, Clivatuzumab tetraxetan, Codrituzumab, Cofetuzumab pelidotin, Coltuximab ravtansine, Conatumumab, Cusatuzumab, Dacetuzumab, Dalotuzumab, Daratumumab, Demcizumab, Denintuzumab matodotin, Depatuxizumab mafodotin, Deriotuximab biotin, Detumomab, Dinutuximab, Drozitumab, DS-8201, Duligotuzumab, Durvalumab, Dusitgitumab, Duvortuxizumab, Ecromeximab, Edrecolomab, Elgemtumab, Elotuzumab, Emactuzumab, Emibetuzumab, Enapotomab vedotin, Enavatuzumab, Enfortumab vedotin, Enoblituzumab, Ensituximab, Epratuzumab, Ertumaxomab, Etaracizumab, Faricimab, Farletuzumab, FBTA05, Ficlatuzumab, Figitumumab, Flanvotumab, Flotetuzumab, Futuximab Galiximab Gancotamab, Ganitumab, Gatipotozumab, Gemtuzumab ozogamicin, Girentuximab, Glembatumumab vedotin, IBI308, ibritumomab tiuxetan, Icrucumab, Iladatuximab vedotin, IMAB362, Imalumab, Imgatuzumab, Indatuximab ravtansine, Indusatumab vedotin, Inebilizumab, Intetumumab, Ipilimumab, Iratumumab, Isatuximab, Istiratumab, Labetuzumab, Lacnotuzumab, Ladiratuzumab vedotin, Lenzilumab, Lexatumumab, Lifastuzumab vedotin, Loncastuximab tesirine, Losatuxizumab vedotin, Lilotomab satetraxetan, Lintuzumab, Lirilumab, Lorvotuzumab mertansine, Lucatumumab, Lumiliximab, Lumretuzumab, MABp1, Mapatumumab, Margetuximab, Matuzumab, Milatuzumab, Mirvetuximab soravtansine, Mitumomab, Modotuximab, Mogamulizumab, Monalizumab, Mosunetuzumab, Moxetumomab pasudotox, Nacolomab tafenatox, Naptumomab estafenatox, Narnatumab, Navicixizumab, Naxitamab, Necitumumab, Nesvacumab, Nimotuzumab, Nivolumab, Nofetumomab merpentan, Obinutuzumab, Ocaratuzumab, Ofatumumab, Olaratumab, Oleclumab, Onartuzumab, Ontuxizumab, Oportuzumab monatox, Oregovomab, Otlertuzumab, Pamrevlumab, Panitumumab, Pankomab, Parsatuzumab, Pasotuxizumab, Patritumab, PDR001, Pembrolizumab, Pemtomomab, Pertuzumab, Pidilizumab, Pinatuzumab vedotin, Polatuzumab vedotin, Pritumumab, Racotumomab, Radretumab, Ramucirumab, Rilotumumab, Rituxiamab, Robatumumab, Rosmantuzumab, Rovalpituzumab tesirine, Sacituzumab govitecan, Samalizumab, Samrotamab vedotin, Seribantumab, Sibrotuzumab, SGN-CD19A, Siltuximab, Sirtratumab vedotin, Sofituzumab vedotin, Solitomab, Spartalizumab, Tabalumab, Tacatuzumab tetraextan, Tapitumumab paptox, Tarextumab, Tavolimab, Telisotuzumab vedotin, Tenatumomab, Tepotidimab, Tetulomab, TGN1412, Tigatuzumab, Timigutuzumab, Tiragotumab, Tislezlizumab, Tisotumab vedotin, TNX-650, Tomuzutuximab, Tovetumab, Trastuzumab, Trastuzumab emtansine, TRBS07, Tremelimumab, Tucotuzumab celmoleukin, Ublituximab, Ulocuplumab, Urelumab, Utomilumab, Vadastuximab talirine, Vandortuzumab vedotin, Vantictumab, Vanucizumab, Varisacumab, Varlilumab, Veltuzumab, Vesencumab, Volociximab, Vonlerolizumab, Vorsetuzumab mafodotin, Votumumab, XMAB-5574, Zalutumumab, Zatuximab, Zenocutuzumab, Zolbetuximab, tositumomab, 5-aminolevulinic acid (Levulan), silicon phthalocyanine Pc 4, naphthalocyanines, metallonaphthalocyanines, tin (IV) purpurins, copper octaethylbenzochlorin, zinc (II) purpurins, m-tetrahydroxyphenylchlorin, mono-Laspartyl chlorine e6, Allumera, Photofrin, Visudyne (Verteporfin), Foscan, Metvix, Hexvix, Cysview, Laserphyrin, Antrin, Photochlor, Photosens, Photrex, Purlytin, Lutex, Lumacan, Cevira, Visonac, BF-200 ALA, Amphinez, azadipyrromethenes, zinc phthalocyanine, afatanib, axitinib, bosutinib, cetuximab, cobimetinib, crizotinib, cabozanitinib, dasatinib, entrectinib, erlotinib, fostamatinib, gefitinib, ibrutinib, imatinib, lapatinib, lenvatinib, mubritinib, nilotinib, pazopanib, pegaptanib, sorafenib, sunitinib, SU6656, vandetanib, vemurafenib, verapamil, cyclosporine, tamoxifen, a calmodulin antagonist, dexverapamil, dexniguldipine, valspodar (PSC 833), biricodar (VX-710), tariquidar (XR9576), zosuquidar (LY335979), laniquidar (R101933), elacridar (GF120918), timcodar (VX-853), taxifolin, naringenin, diosmin, quercetin, diltiazem, bepridil, nicardipine, nifedipine, felodipine, isradipine, trifluoperazine, clopenthixol, trifluopromazine, flupenthixol, emopamil, gallopamil, Ro11-2933, amiodarone, clarithromycin, colchicines, erythromycin, lansoprazole, omeprazole, paroxetine, sertraline, quinidine, 3-methyladenine, wortmannin, LY294002, PT210, GSK-2126548, spautin-1, SAR405, compound 31, VPS34-IN1, PIK-III, compound 6, MRT68921, SBI-30 0206965, pepstatin A, E64d, bafilomycin $A^1$, clomipramine, lucanthone, chloroquine, hydroxychloroquine, Lys05, ARN5187, compound 30, fluoropyrimidine, gemcitabine, cisplatin, NBTXR3, Nimoral, trans sodium crocetinate, NVX-108, misonidazole, metronidazole, tirapazamine, MK-4827 (also known as niraparib), rucaparib, iniparib, talazoparib, olaparib, veliparib, CEP 9722, E7016, BGB2-290, 3-aminobenzamide, rapamycin, sirolimus, temsirolimus, everolimus, ridaforolimus, deforolimus, dactolisib, sapanisertib, AZD8055, AZD2014, aminoglutethimide, testolactone, anastrozole, letrozole, exemestane, vorozole, formestane, fadrozole, 1,4,6-androstatrien-3,17-dione, 4-androstene,3,6,17-trione, aminoglutethimide, ketoconazole, abiraterone acetate, and/or seviteronel.

The disclosed APBA therapeutic peptides are further useful in a method for the prevention, treatment, control, amelioration, or reduction of risk of the cancers noted herein. The disclosed APBA therapeutic peptides are further useful in a method for the prevention, treatment, control, amelioration, or reduction of risk of the aforementioned cancers in combination with other agents.

In one aspect, the disclosed APBA therapeutic peptides can be used in combination with one or more other drugs in the treatment, prevention, control, amelioration, or reduction of risk of cancers for which disclosed APBA therapeutic peptides or the other drugs can have utility, where the combination of the drugs together are safer or more effective than either drug alone. Such other drug(s) can be administered, by a route and in an amount commonly used therefor, contemporaneously or sequentially with a compound of the present disclosure. When a compound of the present disclosure is used contemporaneously with one or more other drugs, a pharmaceutical composition in unit dosage form containing such other drugs and a disclosed compound is preferred. However, the combination therapy can also include therapies in which a disclosed compound and one or more other drugs are administered on different overlapping schedules. It is also contemplated that when used in combination with one or more other active ingredients, the disclosed APBA therapeutic peptides and the other active ingredients can be used in lower doses than when each is used singly. Accordingly, the pharmaceutical compositions include those that contain one or more other active ingredients, in addition to a compound of the present disclosure.

The above combinations include combinations of a disclosed compound not only with one other active compound, but also with two or more other active compounds. Likewise, disclosed APBA therapeutic peptides can be used in combination with other drugs that are used in the prevention, treatment, control, amelioration, or reduction of risk of the cancers for which disclosed APBA therapeutic peptides are useful. Such other drugs can be administered, by a route and in an amount commonly used therefor, contemporaneously or sequentially with a compound of the present disclosure. When a compound of the present disclosure is used contemporaneously with one or more other drugs, a pharmaceutical composition containing such other drugs in addition to a disclosed compound is preferred. Accordingly, the pharmaceutical compositions include those that also contain one or more other active ingredients, in addition to a compound of the present disclosure.

The weight ratio of a disclosed compound to the second active ingredient can be varied and will depend upon the effective dose of each ingredient. Generally, an effective dose of each will be used. Thus, for example, when a compound of the present disclosure is combined with another agent, the weight ratio of a disclosed compound to the other agent will generally range from about 1000:1 to about 1:1000, preferably about 200:1 to about 1:200. Combinations of a compound of the present disclosure and other active ingredients will generally also be within the aforementioned range, but in each case, an effective dose of each active ingredient should be used.

In such combinations a disclosed compound and other active agents can be administered separately or in conjunction. In addition, the administration of one element can be prior to, concurrently with, or subsequent to the administration of other agent(s). Accordingly, the disclosed APBA therapeutic peptides can be used alone or in combination with other agents which are known to be beneficial in the subject indications or other drugs that affect receptors or enzymes that either increase the efficacy, safety, convenience, or reduce unwanted side effects or toxicity of the other agents. The disclosed APBA therapeutic peptide and the other agent can be coadministered, either in concomitant therapy or in a fixed combination.

In one aspect, the compound can be employed in combination with anticancer agents, and combinations thereof, and the like, or the subject compound can be administered in conjunction with the use of physical methods such as with debridement of a wound or infected tissue.

In the treatment of a cancer, an appropriate dosage level will generally be about 0.01 to 500 mg per kg patient body weight per day which can be administered in single or multiple doses. Preferably, the dosage level will be about 0.1 to about 250 mg/kg per day; more preferably about to about 100 mg/kg per day. A suitable dosage level can be about 0.01 to 250 mg/kg per day, about 0.05 to 100 mg/kg per day, or about 0.1 to 50 mg/kg per day. Within this range the dosage can be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10, 15, 20, 25, 50, 75, 100, 150,200, 250, 300, 400, 500, 600, 750, 800, 900, and 1000 milligrams of the active ingredient for the symptomatic adjustment of the dosage to the patient to be treated. The compounds can be administered on a regimen of 1 to 4 times per day, preferably once or twice per day. This dosage regimen can be adjusted to provide the optimal therapeutic response. It will be understood, however, that the specific dose level and frequency of dosage for any particular patient can be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Thus, in one aspect, the disclosure relates to methods for treating a cancer in at least one cell, comprising the step of contacting the at least one cell with at least one compound of the disclosure, in an amount effective to alter the response in the at least one cell. In a further aspect, the cell is mammalian, for example human. In a further aspect, the cell has been isolated from a subject prior to the contacting step. In a further aspect, contacting is via administration to a subject.

Imaging Uses for APBA Peptides

In various aspects, the present disclosure provides methods of targeting cells, tissues, proteins, or organs for imaging comprising administration of an effective amount of a disclosed APBA therapeutic peptide or a disclosed pharmaceutical composition to a subject in need thereof. It is understood that reference to a disclosed APBA therapeutic peptide is inclusive of the disclosed APBA therapeutic peptide, as well as pharmaceutically acceptable salt, hydrate, solvate, or polymorph forms thereof and a disclosed APBA therapeutic peptide further comprising an imaging or contrast agent.

In one aspect, the imaging or contrast agent can be $^{11}$C-L-methyl-methionine, $^{18}$F-fluorodeoxyglucose, $^{18}$F-sodium fluoride, $^{18}$F-fluorochoilne, $^{18}$F desmethoxyfallypride, $^{67}$Ga-Ga$^{3+}$, $^{68}$Ga-dotatoc, $^{68}$Ga-PSMA, $^{111}$In-diethylenetriaminepentaacetic acid, $^{111}$In-lekuocytes, $^{111}$In-platelets, $^{111}$In-penetreotide, $^{111}$In-octreotide, $^{123}$I-iodide, $^{123}$I-o-iodohippurate, $^{123}$I-miodobenzylguanidine, $^{123}$I-FP-CIT, $^{125}$I-fibrinogen, $^{131}$I-iodide, $^{131}$I-miodobenzylguanidine, $^{81}$Kr$^{m}$-gas, $^{81}$Kr$^{m}$-aqueous solution, $^{13}$N-ammonia, $^{15}$O-water, $^{75}$Se-selenorcholesterol, $^{75}$Se-seleno-25-homo-tauro-cholate, $^{120}$TI-TI$^{+}$, $^{133}$Xe-gas, $^{133}$Xe in isotonic sodium chloride solution, $^{99}$Tc$^{m}$-pertechnetate, $^{99}$TC-human albumin including macroaggregates or microspheres, $^{99}$Tc$^{m}$-phosphonates and/or phosphates, $^{99}$Tc$^{m}$-diethylenetriaminepentaacetic acid, $^{99}$Tc$^{m}$-dimercaptosuccinic acid, $^{99}$TC$^{m}$-colloid, $^{99}$TC$^{m}$-hepatic iminodiacetic acid, $^{99}$Tc$^{m}$ whole red blood cells, $^{99}$Tc$^{m}$-mercaptoacetyltriglycine, $^{99}$Tc$^{m}$ exametazime including exametazime labeled leucocytes, $^{99}$Tc$^{m}$ sesta-methoxy isobutyl isonitrile, $^{99}$Tc$^{m}$ IMMU-MN3 murine Fab'-SH antigranulocyte monoclonal antibody fragments, $^{99}$Tc$^{m}$-technegas, $^{99}Tc^m$ human immunoglobulin, $^{99}Tc^m$-tetrofosmin, $^{99}TC^m$-ethyl cysteinate dimer, diatrizoate, metrizoate, iothalamate, or ioxaglate, Iopamidol, iohexol, ioxilan, iopromide, iodixanol, ioversol, gadoterate, gadodiamide, gadobenate, gadopentetate, gadoteridol, gadofosveset, gadoversetamide, gadoxetate, gadobutrol, methylene blue, indigo carmine, fluorescein isothiocyanate, indocyanine green, rosamine, BODIPY (boron-dipyrromethane) derivatives, chalcone, xanthone, oxazole yellow, thiazole orange, fluorescein, luciferin, Texas red, squaraine, a porphyrine, a phthalocyanine, a polymethine cyanine dye (e.g., Cy3, Cy5, Cy5.5, Cy7), an Alexa fluor, a precursor molecule (e.g., 5-aminlevulinic acid) for a fluorescent metabolite (e.g., protoporphyrin X), or a quantum dot that can optionally be coated or encapsulated with a polymer or hydrogel. In one aspect, imaging can be carried out by computed tomography, fluoroscopy, magnetic resonance imaging, magnetic resonance angiography, mammography, nuclear medicine, X-ray, positron emission tomography, ultrasound, or another method.

In a further aspect, the subject is a human. In another aspect, the subject is a vertebrate animal. Further in this aspect, the vertebrate animal is a fish, a bird, or a mammal. In a still further aspect, the vertebrate animal is a livestock animal. In yet a further aspect, the vertebrate animal is a companion animal. In an even further aspect, the vertebrate animal is a farm animal. In a still further aspect, the vertebrate animal is a zoo animal. In yet a further aspect, the vertebrate animal is a laboratory animal. In an even further aspect, the vertebrate animal is an aquaculture fish. In a still further aspect, the vertebrate animal is selected from *Bison* sp., *Bos* sp., *Canis* sp., *Capra* sp., *Equus* sp., *Felis* sp., *Gallus* sp., *Lama* sp., *Meleagris* sp., *Oryctolagus* sp., *Ovis* sp., and *Sus* sp.

In a further aspect, the vertebrate animal has been diagnosed with a need for imaging prior to the administering step. In a further aspect, the disclosure relates to a method for the imaging of a cell, tissue, protein, or organ in a vertebrate animal, further comprising the step of identifying a vertebrate animal in need of imaging of the cell, tissue, protein, or organ.

In a further aspect, administering comprises mixing an effective amount of a disclosed APBA imaging peptide with the food of the vertebrate animal. In a still further aspect, administering comprises administering enterally an effective amount of the disclosed APBA imaging peptide with the food of the vertebrate animal. In yet a further aspect, administering comprises administering an oral bolus of an effective amount of the disclosed APBA imaging peptide with the food of the vertebrate animal. In various aspects, administering to a vertebrate animal comprises intravenous administration or parenteral administration to the vertebrate animal.

In one aspect, the subject compound can be administered in conjunction with the use of physical methods such as with debridement of a wound or infected tissue, biopsy, surgery, radiotherapy, laser ablation, cryoablation, dermabrasion, radiofrequency ablation, microwave ablation, high-intensity focused ultrasound, embolization, chemoembolization, veterbroplasty, feeding tube placement, venous access catheter placement, or another physical method.

Other Uses for APBA Peptides

In some aspects, the disclosed APBA therapeutic peptides can be used to bind to misfolded proteins (e.g., amyotrophic lateral sclerosis, Alzheimer's disease, Parkinson's disease, Huntington's disease, and/or prion diseases), overexpressed proteins (e.g., increased PKD1 leading to polycystic kidney disease, and/or diseases associated with copy number variants including, but not limited to, autism spectrum disorders and schizophrenia or chromosomal duplications including Down syndrome), and/or proteins that include deleterious mutations (e.g., amino acid substitutions causing misfolding or altered active sites, truncated sequences, and the like).

Manufacture of a Medicament

In various aspects, the present disclosure pertains to uses of a disclosed APBA therapeutic peptide, or a pharmaceutically acceptable salt thereof, in the manufacture of a medicament with a pharmaceutically acceptable carrier or diluent for the treatment of a disorder associated with aberrant protein expression, or a cancer, or a viral, bacterial, or fungal disease in a mammal, e.g., a human. In a further aspect, the present disclosure pertains to methods for the manufacture of a medicament to treat a cancer or an infection associated with a bacterium, a fungus, or a virus comprising combining at least one disclosed compound, or a pharmaceutically acceptable salt thereof in the manufacture of a medicament with a pharmaceutically acceptable carrier or diluent.

In one aspect, the disclosure relates to a medicament comprising one or more disclosed APBA therapeutic peptides; or a pharmaceutically acceptable salt, hydrate, solvate, or polymorph thereof.

In various aspect, the disclosure relates methods for the manufacture of a medicament for the treatment of a cancer, a bacterial, viral, or fungal infection, or disorder associated with aberrant protein expression in a mammal (e.g., humans) comprising combining one or more disclosed APBA therapeutic peptides, or a pharmaceutically acceptable salt, solvate, hydrate, or polymorph thereof, and at least one additional therapeutic agent with a pharmaceutically acceptable carrier.

Kits

In a further aspect, the present disclosure relates to kits comprising at least one disclosed compound, or a pharmaceutically acceptable salt, hydrate, solvate, or polymorph thereof, and one or more of: (a) at least one agent known to treat a cancer, a bacterial, viral, or fungal infection, or disorder associated with aberrant protein expression; or (b) instructions for treating cancer, a bacterial, viral, or fungal infection, or a disorder associated with aberrant protein expression. In some aspects, the kits comprise at least one disclosed compound, or a pharmaceutically acceptable salt, hydrate, solvate, or polymorph thereof, modified to incorporate an imaging or contrast agent, and instructions for using the imaging or contrast agent to obtain medical images useful for diagnostic and/or treatment (e.g., ablation, surgery, embolization, and the like) purposes.

The disclosed APBA therapeutic peptides and/or pharmaceutical compositions comprising the disclosed APBA therapeutic peptides can conveniently be presented as a kit, whereby two or more components, which may be active or inactive ingredients, carriers, diluents, and the like, are provided with instructions for preparation of the actual dosage form by the patient or person administering the drug to the patient. Such kits may be provided with all necessary materials and ingredients contained therein, or they may contain instructions for using or making materials or components that must be obtained independently by the patient or person administering the drug to the patient. In further aspects, a kit can include optional components that aid in the administration of the unit dose to patients, such as vials for reconstituting powder forms, syringes for injection, customized IV delivery systems, inhalers, etc. Additionally, a kit can contain instructions for preparation and administration of the compositions. The kit can be manufactured as a single use unit dose for one patient, multiple uses for a particular patient (at a constant dose or in which the individual compounds may vary in potency as therapy progresses); or the kit may contain multiple doses suitable for administration to multiple patients ("bulk packaging"). The kit components may be assembled in cartons, blister packs, bottles, tubes, and the like.

In a further aspect, the disclosed kits can be packaged in a daily dosing regimen (e.g., packaged on cards, packaged with dosing cards, packaged on blisters or blow-molded plastics, etc.). Such packaging promotes products and increases patient compliance with drug regimens. Such packaging can also reduce patient confusion. The present invention also features such kits further containing instructions for use.

In a further aspect, the present disclosure also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration.

In various aspects, the disclosed kits can also comprise compounds and/or products copackaged, co-formulated, and/or co-delivered with other components. For example, a drug manufacturer, a drug reseller, a physician, a compounding shop, or a pharmacist can provide a kit comprising a disclosed compound and/or product and another component for delivery to a patient.

It is contemplated that the disclosed kits can be used in connection with the disclosed methods of making, the disclosed methods of using or treating, and/or the disclosed compositions.

Research Tools

The disclosed APBA therapeutic peptides and pharmaceutical compositions have activity as therapeutic agents against diseases, disorders, and conditions associated with cancer, a bacterial, viral, or fungal infection, or aberrant protein expression. As such, the disclosed APBA therapeutic peptides are also useful as research tools. Accordingly, one aspect of the present disclosure relates to a method of using a disclosed APBA therapeutic peptide as a research tool, the method comprising conducting a biological assay using a disclosed APBA therapeutic peptide in an anti-microbial assay and determining microbial (e.g., fungal, bacterial) growth, or wherein the biological assay determines cell viability (e.g., cancer cell viability) in the presence of the disclosed APBA therapeutic assay, or the like. Accordingly, disclosed APBA therapeutic peptides can also be used to evaluate new chemical compounds. Thus another aspect of the invention relates to a method of evaluating a test compound in a biological assay, comprising: (a) conducting a biological assay with a test compound to provide a first assay value; (b) conducting the biological assay with a disclosed APBA therapeutic peptide to provide a second assay value; wherein step (a) is conducted either before, after or concurrently with step (b); and (c) comparing the first assay value from step (a) with the second assay value from step (b). Still another aspect of the invention relates to a method of studying a biological system, e.g., a model animal for a clinical condition, the method comprising: (a) contacting the biological system with a disclosed APBA therapeutic peptide; and (b) determining the effects caused by the compound on the biological system or sample.

Without further elaboration, it is believed that one skilled in the art can, based on the above description, utilize the present disclosure to its fullest extent. The following specific embodiments and examples are, therefore, to be construed as merely illustrative, and not limitative of the remainder of the disclosure in any way whatsoever.

Now having described the aspects of the present disclosure, in general, the following Examples describe some additional aspects of the present disclosure. While aspects of the present disclosure are described in connection with the following examples and the corresponding text and figures, there is no intent to limit aspects of the present disclosure to this description. On the contrary, the intent is to cover all alternatives, modifications, and equivalents included within the spirit and scope of the present disclosure.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the disclosure and are not intended to limit the scope of what the inventors regard as their disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example 1: Design and Experimental Validation of Phage Display Library

A commercial phage display library (C&C, New England Biolabs) was used to produce an APBA-dimer library for selection of ligands that interact with protein surfaces. Cyclic peptide libraries are conjugated to one or more covalent "warheads" or protein surface binding ligands. When multiple "warheads" are desired, one "warhead" is attached to an N-terminal cysteine residue and another warhead is attached to an internal cysteine residue; warheads can be the same or different. 2-cyanobenzathiazole (CBT) can be reacted with a cysteine residue, which allows for selective N-terminal modification of phage proteins (FIGS. 1A-1F).

Figure 1G:
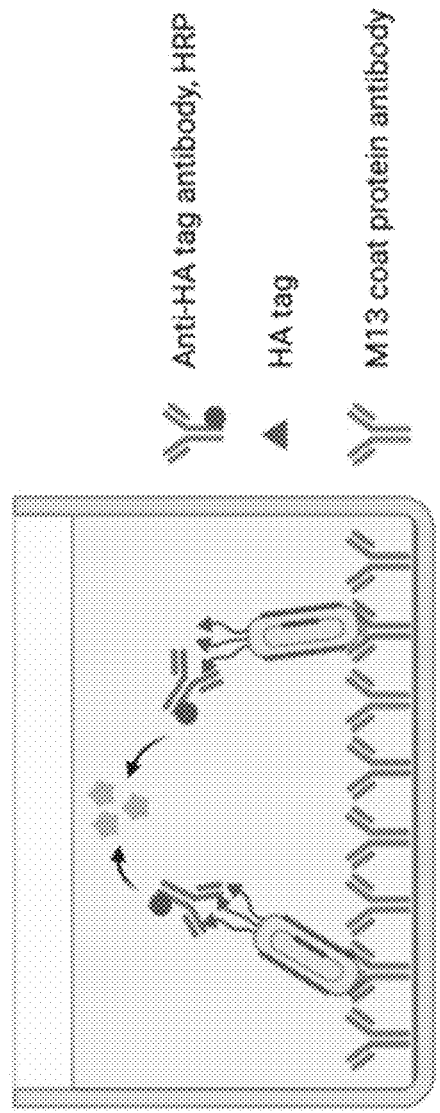
FIG. 1G shows a time-dependent ELISA assay carried out to optimize Factor Xa cleavage conditions. 1 µL of Factor Xa (1 mg/mL) was added to 100 µL phage solution (1×10$^{13}$ pfu/mL) in a reaction buffer (20 mM tris-HCl, 100 mM NaCl, 2 mM CaCl$_2$), pH 8.0) and incubated for 0.5, 1, 2, 4, or 6 h and overnight at room temperature, respectively. The phage was precipitated at 4° C. for 1 h by adding 17 µL 20% PEG/2.5 M NaCl and then was pelleted by centrifugation and resuspended in 100 µL PBS buffer (pH 7.4) for further ELISA assay. M13 major coat protein antibody was attached on a microplate to pull down phage that contained an HA tag, which is then quantified using an HA tag monoclonal antibody-HRP.

An HA tag-IEGR—C(X)$_5$C peptide library ("IEGR—C (X)$_5$C" disclosed as SEQ ID NO: 83) having an HA tag followed by a Factor Xa cleavage site (IEGR (SEQ ID NO: 79)) was fused on the N-terminus of a phage protein, and a C(X)$_5$C peptide library was incorporated between the Factor Xa cleavage site and the main body of the phage protein. As a result, the N-terminal cysteine could be liberated by Factor Xa cleavage and the Factor Xa cleavage efficiency could be monitored by the removal of the HA tag from the phage (FIG. 1G).

Figure 1H:
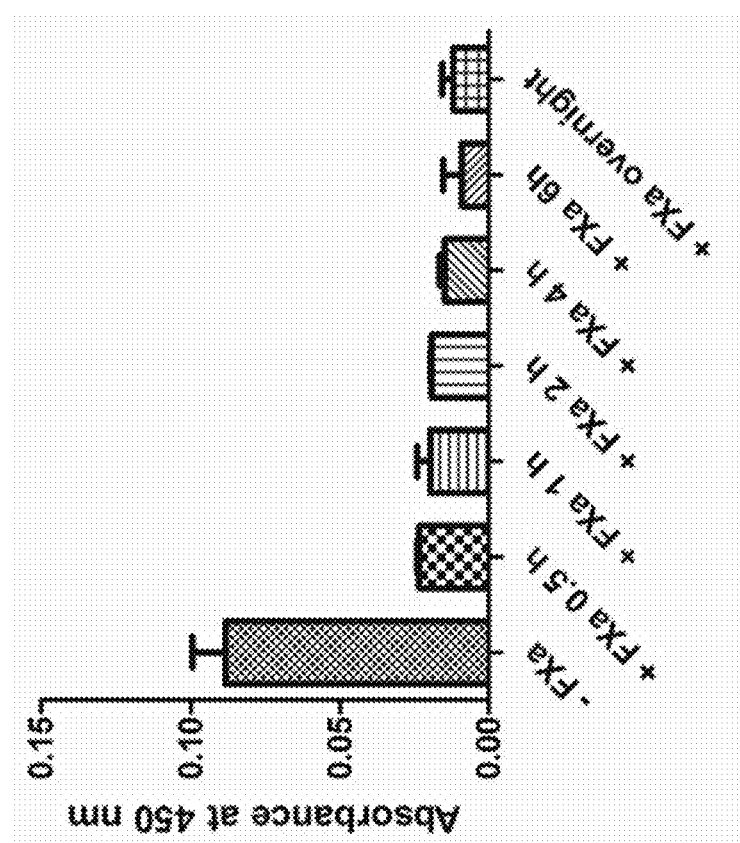
FIG. 1H shows results of the ELISA assay; a 6 h incubation time was long enough for efficient Factor Xa cleavage.
Figure 1I:
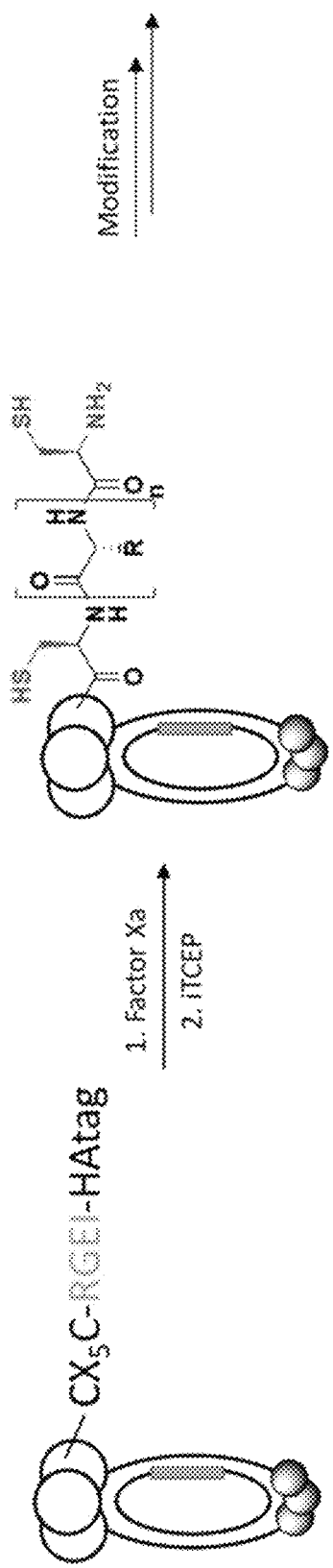
FIG. 1I shows a schematic illustration of a phage library carrying double warheads. Following Factor Xa cleavage, the phage protein was subsequently reduced by iTCEP (immobilized tris(2-carboxyethyl)phosphine) to give a free N-terminal cysteine and an internal cysteine on the phage protein. The resulting phage was subjected to modification and the extent of modification was accessed by a biotinylation-pulldown assay.
Figure 1J:
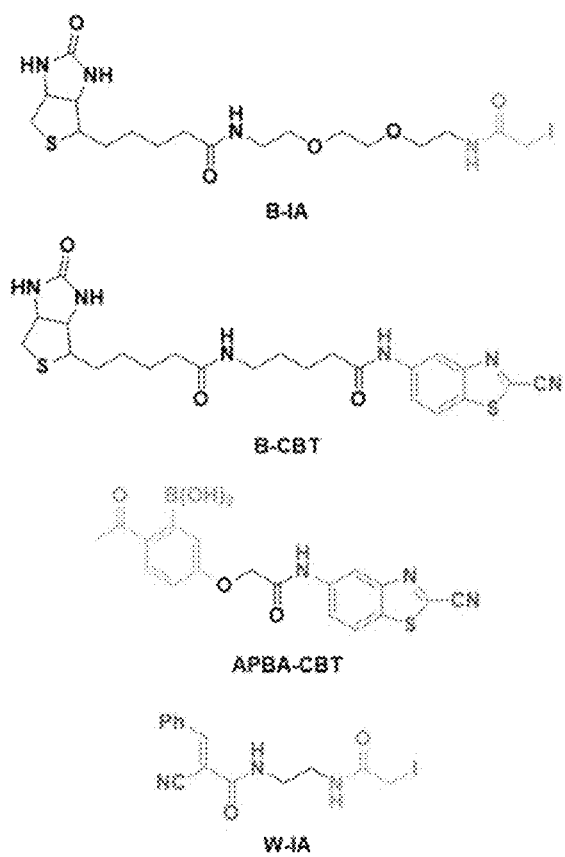
FIG. 1J shows structures of some molecules used to treat the phage protein for pulldown assays. As positive controls, reduced phage protein treated with either biotin-iodoacetamide (B-IA) or biotin CBT (B-CBT, 2-cyanobenzothiazole) has a complete streptavidin pulldown. In contrast, phage treated with APBA-CBT first and then B-CBT afforded no obvious streptavidin pulldown, indicating the N-terminal cysteine was totally captured by APBA-CBT.
Figure 1K:
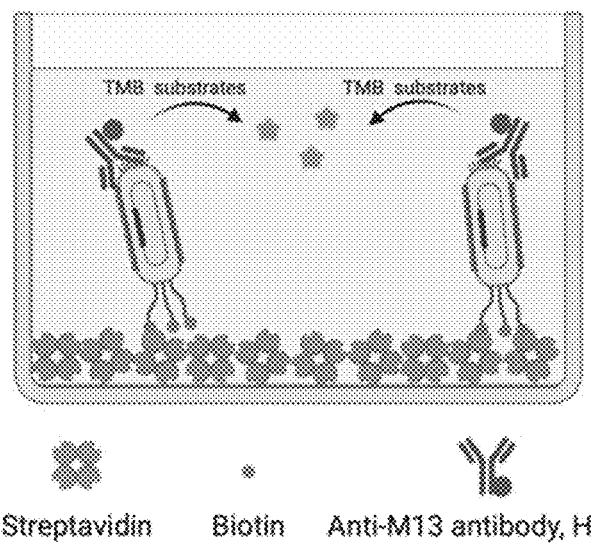
FIG. 1K shows a schematic of the pulldown assay.
Figure 1L:
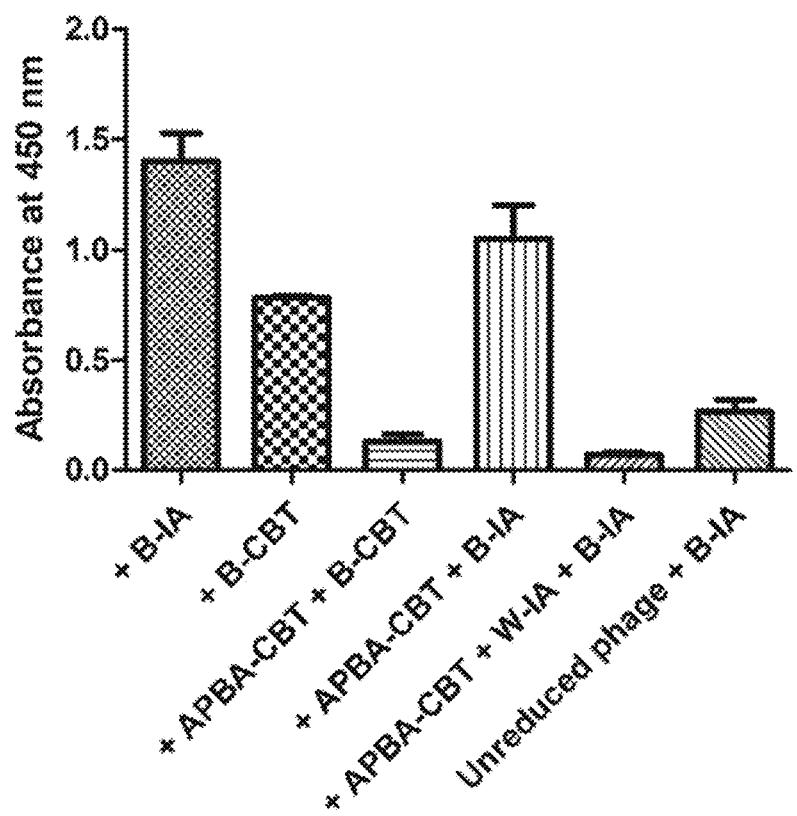
FIG. 1L shows results of the pulldown assay. Streptavidin pulldown was effectively blocked by phage protein treated with APBA-CBT, W-IA ("warhead" iodoacetamide), and B-IA successively, indicating complete labeling of internal cysteines by W-IA.
Figure 2A:
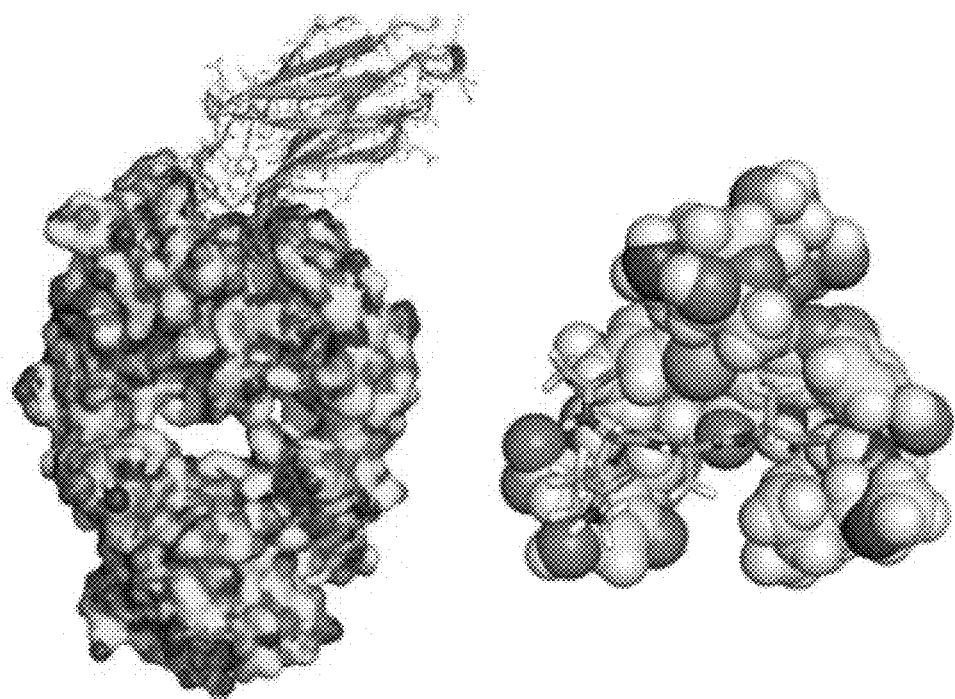
FIG. 2A shows antibody recognition of target proteins relies on the antibody serving as a receptor for protein substructures such as a loop (left) and peptide natural products as exemplified by vancomycin mimic the binding mode of antibodies for target binding (right).
Figure 2B:
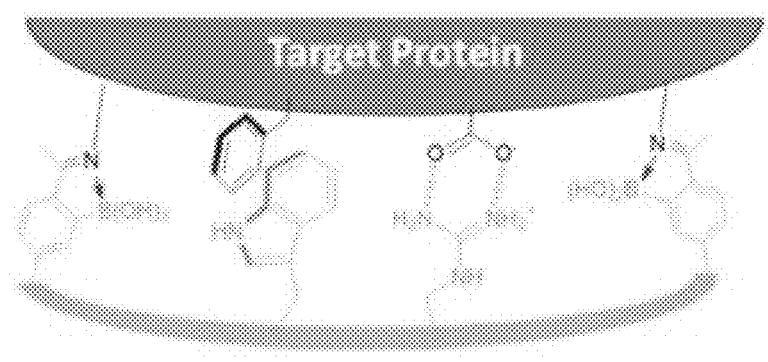
FIG. 2B shows a postulated mode of protein surface binding by enlisting additional molecular interactions, such as surface binding via covalent and noncovalent interactions.

A time-dependent ELISA assay was carried out to optimize Factor Xa cleavage conditions. 1 μL of Factor Xa (1 mg/mL) was added to 100 μL phage solution (1×10¹³ pfu/mL) in a reaction buffer (20 mM tris-HCl, 100 mM NaCl, 2 mM CaCl$_2$, pH 8.0) and incubated for 0.5, 1, 2, 4, or 6 h and overnight at room temperature, respectively. The phage was precipitated at 4° C. for 1 h by adding 17 μL 20% PEG/2.5 M NaCl and then was pelleted by centrifugation and resuspended in 100 μL PBS buffer (pH 7.4) for further ELISA assay. M13 major coat protein antibody was attached on a microplate to pull down phage that contained an HA tag, which is then quantified using an HA tag monoclonal antibody-HRP (FIG. 1H); a 6 h incubation time was long enough for efficient Factor Xa cleavage. For a phage library carrying double warheads, following Factor Xa cleavage, the phage protein was subsequently reduced by iTCEP to give a free N-terminal cysteine and an internal cysteine on the phage protein. The resulting phage was subjected to modification and the extent of modification was accessed by a biotinylation-pulldown assay (FIGS. 1I-K). As positive controls, reduced phage protein treated with either biotin-iodoacetamide (B-IA) or biotin CBT (B-CBT) has a complete streptavidin pulldown. In contrast, phage treated with APBA-CBT first and then B-CBT afforded no obvious streptavidin pulldown, indicating the N-terminal cysteine was totally captured by APBA-CBT. Streptavidin pulldown was effectively blocked by phage protein treated with APBA-CBT, W-IA, and B-IA successively, indicating complete labeling of internal cysteines by W-IA (FIG. 1L). Collectively, these results show the validation of a doubly modified peptide library on phage protein.

Example 2: Targeting Streptavidin

It was expected that dynamic iminoboronate formation would provide a powerful driving force for binding protein surface lysines. When used in combination with additional noncovalent driving forces, the iminoboronate warheads disclosed herein can enable peptide design to target specific protein surfaces. To test the hypothesis, four proteins were identified for which surface binding peptides were quickly identified from the APBA-dimer library.

Figure 3A:
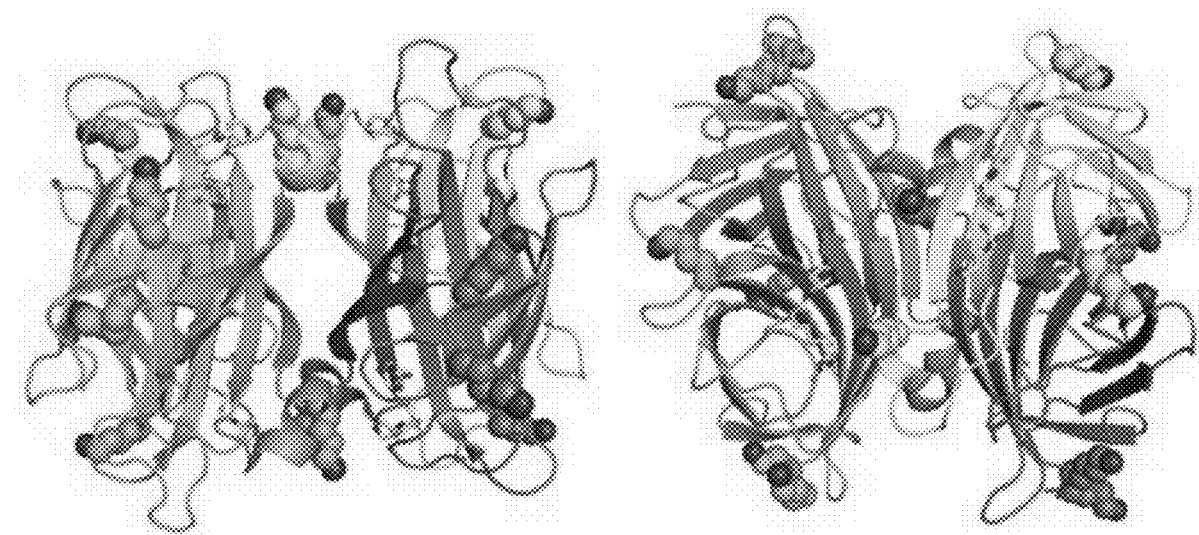
FIG. 3A shows surface lysines of streptavidin amenable to conjugation with APBA-dimer peptides (left: side view.

Streptavidin is commonly used as a model protein for validating phage-displayed peptide libraries. Peptides with a characteristic HPQ sequence have been documented multiple times with competitive binding to the biotin-binding pocket. Streptavidin is a homotetrameric protein (FIG. 3A). The monomers fold into a β-barrel and assemble horizontally through interactions of the barrel wall. This tetrameric protein displays 16 lysine residues overall. The 2 symmetric faces (top and bottom of the barrels) each harbor 4 lysines, while the remaining 8 lysines (2 from each monomer at the C-terminus) locate on the exterior walls of the β-barrel assembly.

To ensure surface binding (versus pocket binding), the disclosed APBA-dimer library was panned against streptavidin beads in the presence of excess biotin (~80 μM). Importantly, the screen was performed in the presence of 10 mg/mL of BSA as an internal competitor. Briefly, the APBA-dimer library was prepared from a commercially available C7C library (New England BioLabs). An input population of 10¹¹ phage particles were mixed with streptavidin-coated beads in the presence of excess biotin and BSA. After 2 h of incubation, the unbound phage was removed by discarding the supernatant following a gentle centrifugation. The beads were washed three times and then treated with an acidic buffer (pH 2.0) to release the bound phage. The output population, typically on the scale of 10⁴ to 10⁵ pfu, was amplified using a standard protocol, and then subjected to chemical modification to generate the APBA-dimer phage for the next round of panning. After three rounds of panning, plaques were randomly selected for sequencing. Two peptide sequences were seen with multiple occurrences out of 60 colonies subjected to sequencing, indicating the convergence of sequence space (Table 1).

TABLE 1

Sequence Convergence Targeting Streptavidin

| Sequence | Number of Occurrences* | SEQ ID NO. |
|---|---|---|
| Blank | 36 | N/A |
| CDGRPDRAC | 3 | 1 |
| CTPRSANYC | 7 | 2 |
| CMATPTRGC | | 3 |
| CVGPHDKTC | | 4 |
| CTKVMDKLC | | 5 |
| CEPRSLANC | | 6 |
| CPTLKPNMC | | 7 |
| CNHELVTVC | | 8 |
| CDVHNPSSC | | 9 |
| CQPARHNNC | | 10 |
| CDDDMAPSC | | 11 |
| CSTPSSQSC | | 12 |
| CQSSPNPLC | | 13 |
| CNGWPGASC | | 14 |
| CSKQDLWQC | | 15 |
| CVPTPGMTC | | 16 |

*Indicates only one occurrence of a sequence.

The peptide hits were synthesized through solid phase peptide synthesis with a triple glycine spacer on the C-terminus followed by a Dap residue carrying a fluorescent label to facilitate binding studies (Table 2). The purified peptides were alkylated with APBA-IA to give the desired APBA dimers SA1/2. In addition, we also synthesized two control peptides (SA1/2-IA) that carry cysteines alkylated with iodoacetamide (IA, in contrast to APBA-IA).

TABLE 2

Streptavidin Binding Sequences and Controls

| Abbreviation/ Identifier | Sequence | SEQ ID NO. |
|---|---|---|
| SA1 | AC$_m$TPRSANYC$_m$GGGDap$^a$ | 72 |
| SA2 | AC$_m$DGRPDRAC$_m$GGGDap | 73 |
| SA1-IA | Ac$_m$TPRSANYC$_m$GGGDap$^b$ | 74 |
| SA2-IA | Ac$_m$DGRPDRAC$_m$GGGDap | 75 |

$^a$C$_m$ = APBA-IA modified cysteine.
$^b$c$_m$ = IA modified cysteine.

Figure 3B:
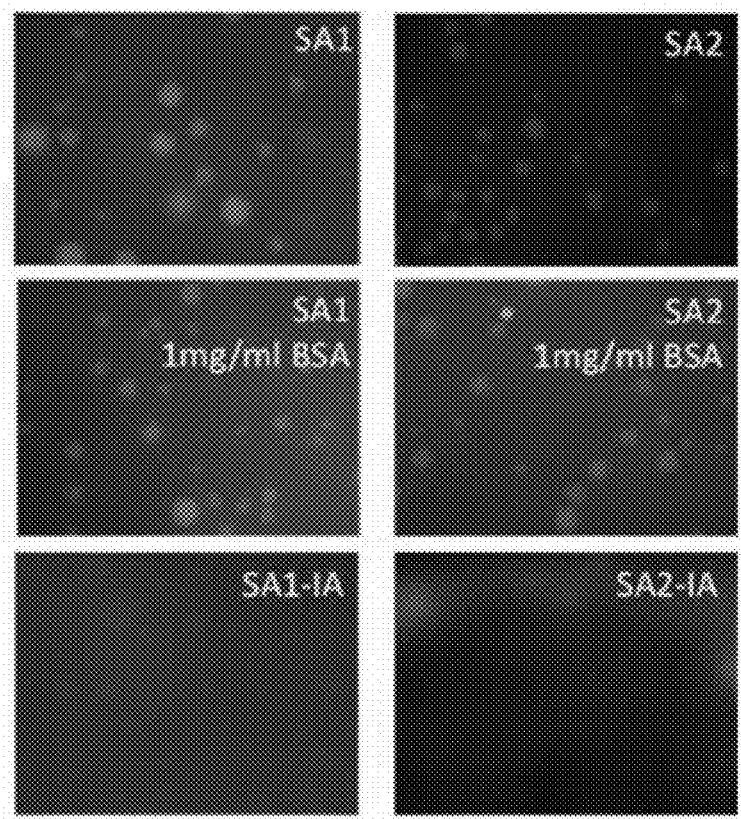
FIG. 3B shows microscopic images of streptavidin-coated beads stained with the peptide hits and controls.
Figure 4:
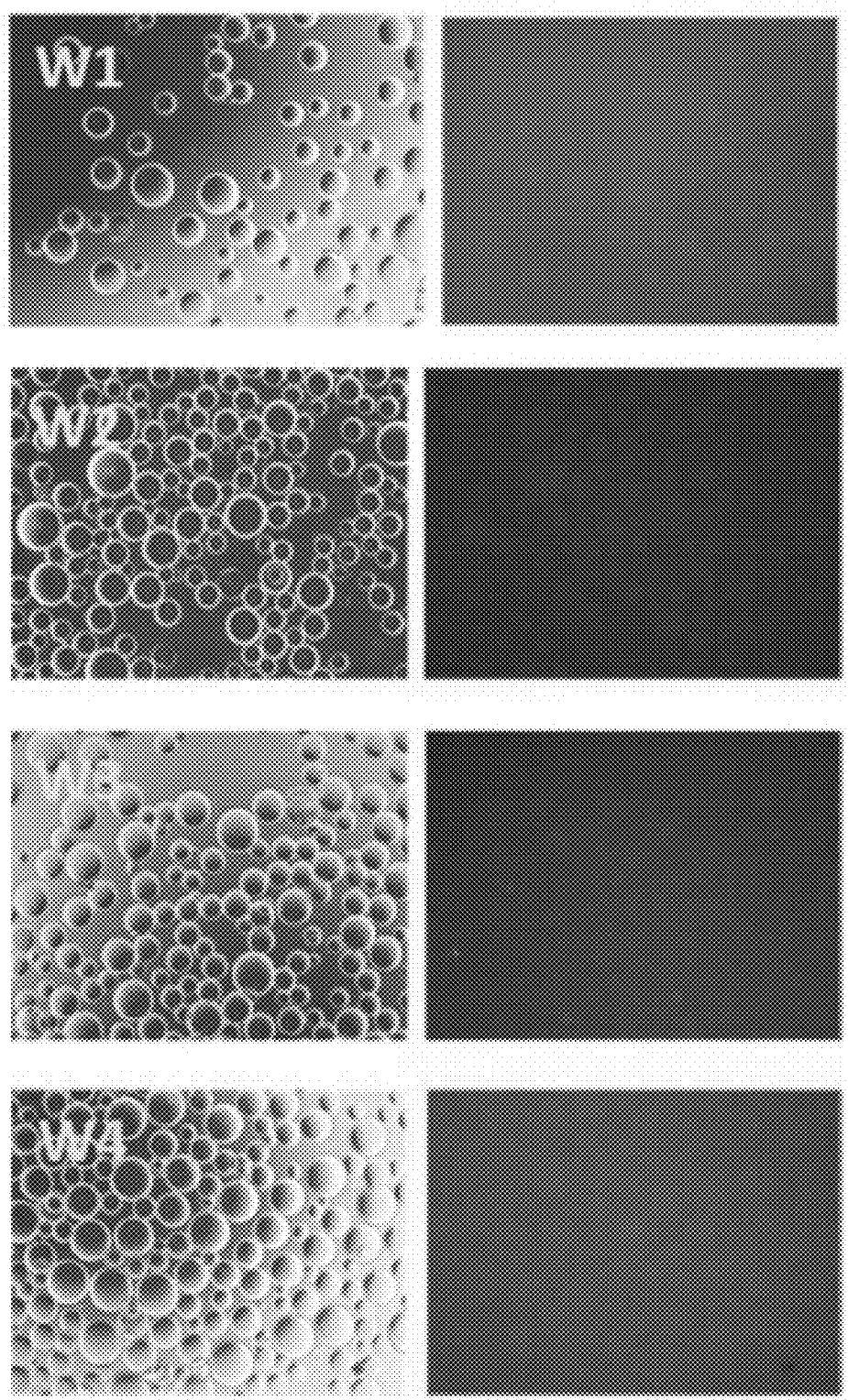
FIG. 4 shows that peptides identified from a sortase A (SrtA) screening. These peptides (W1, W2, W3, and W4) fail to stain streptavidin-coated beads even at 25 μm, highlighting the specificity of peptide hits and validating the disclosed screening protocol for protein binding.

The fluorescently labeled peptides were tested for staining streptavidin-coated beads with excess biotin present, imitating the conditions used for phage panning. Both peptide hits (SA1/2) afforded fluorescence staining of the beads at low micromolar concentrations (FIG. 3B). Importantly, the fluorescence brightness of the beads was minimally affected by the addition of BSA (1 mg/mL), which indicates the specificity of the peptides for streptavidin. As expected, the control peptides SA1/2-IA, which lack the APBA warheads, failed to stain the streptavidin beads under the same experimental conditions (FIG. 3B). Furthermore, no bead staining was observed by several APBA-dimer peptides obtained from other screens (FIG. 4, Table 3), indicating that the streptavidin binding observed for SA1/2 is not a general phenomenon of the APBA dimers.

TABLE 3

Sortase A Binding Sequences and Controls

| Abbreviation/Identifier | Sequence | SEQ ID NO. |
|---|---|---|
| W1 | AC$_m$HPVSGQKC$_m$GGGDap | 68 |
| W2 | AC$_m$LNSSQPSC$_m$GGGDap | 69 |
| W3 | AC$_m$IQKNTTTC$_m$GGGDap | 70 |
| W4 | AC$_m$TPNKTPKC$_m$GGGDap | 71 |

$^a$C$_m$ = APBA-IA modified cysteine.

Figure 5A:
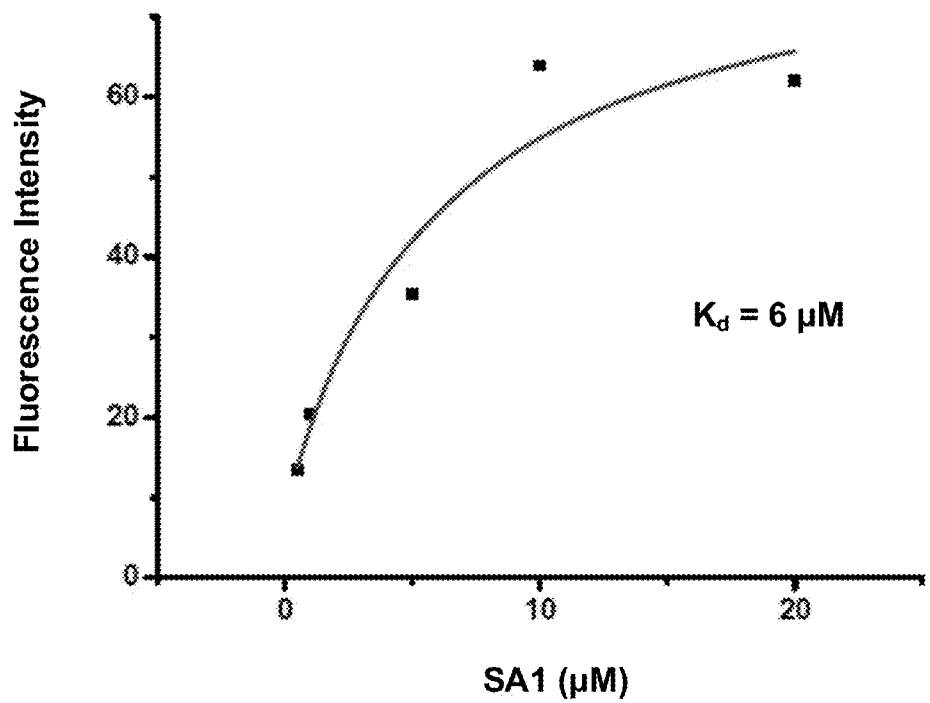
FIG. 5A shows binding curves and binding/dissociation constant ($K_d$) for peptide hit SA1 binding streptavidin.
Figure 5B:
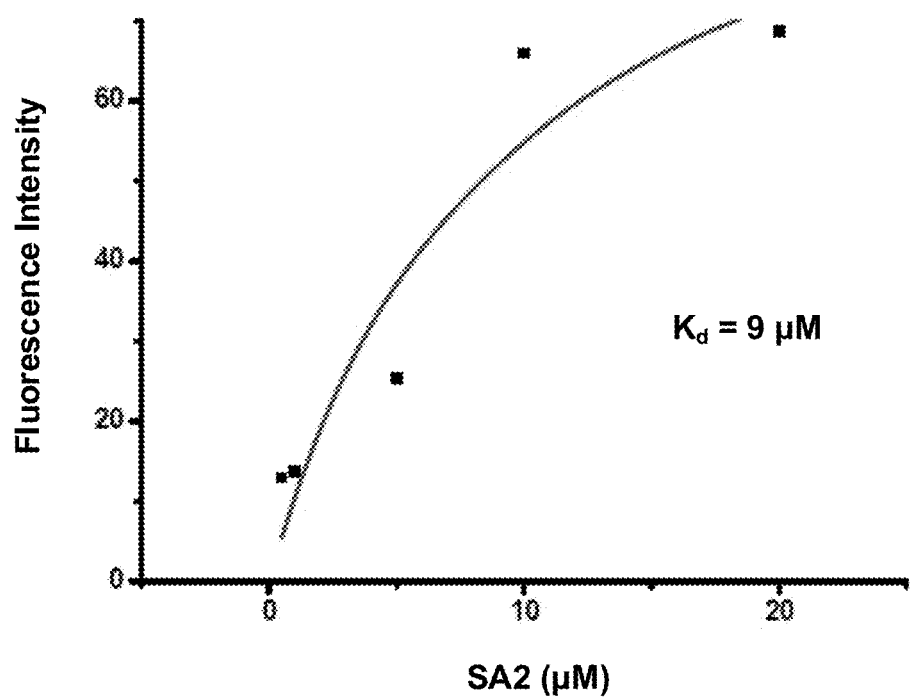
FIG. 5B shows binding curves and $K_d$ for peptide hit SA2 binding streptavidin, where SA1 and SA2 represent peptide hits binding streptavidin. Fitting the binding curves of SA1 and SA2 yields the $K_d$ values for these two streptavidin-binding peptide hits.
Figure 6:
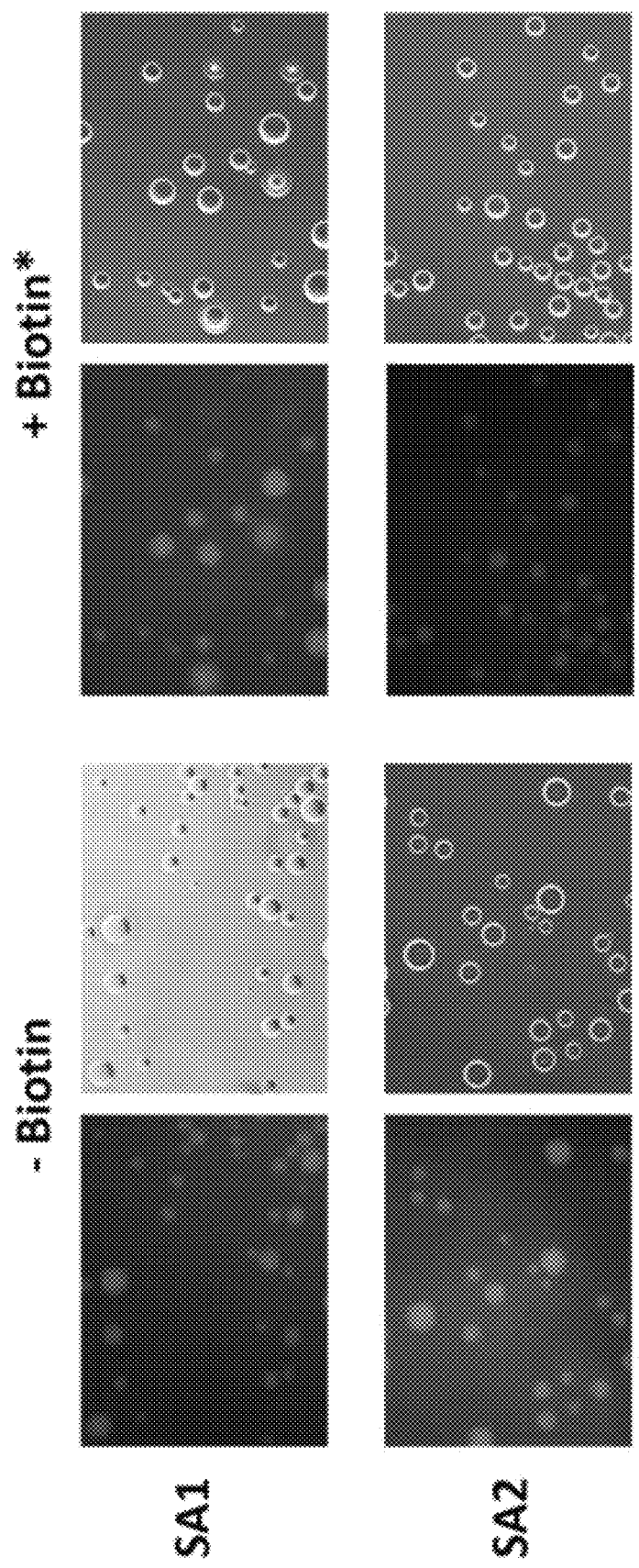
FIG. 6 shows microscopic images of streptavidin-coated beads stained with SA1 and SA2; the streptavidin beads were saturated with biotin.
Figure 7:
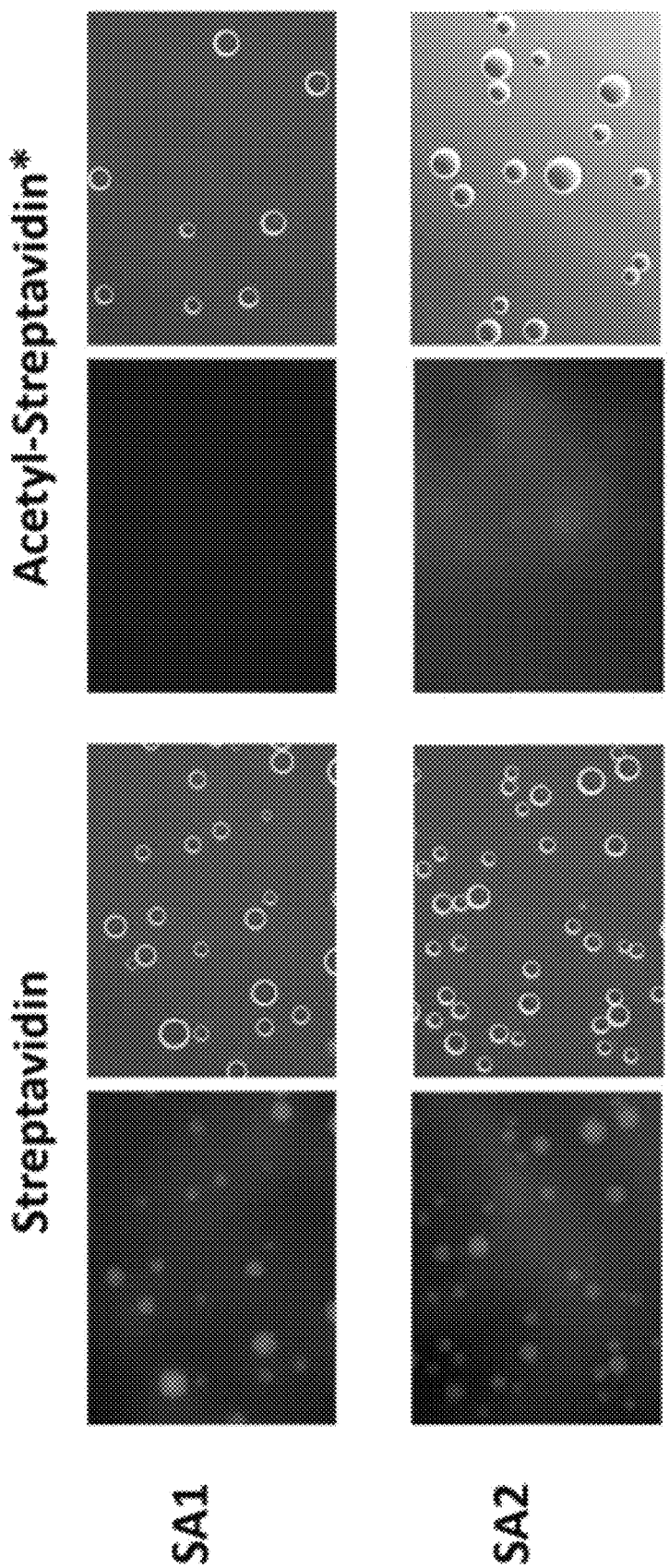
FIG. 7 shows microscopic images of streptavidin-coated beads stained with SA1 and SA2. Streptavidin beads were incubated with acetic acid N-hydroxysuccinimide ester (3 mM).

Instead, the peptide sequences of SA1/2 are important for streptavidin binding as expected for peptide hits identified from screening. The potency of SA1/2 for streptavidin binding was assessed by recording the fluorescence intensity of the beads at varied peptide concentrations. Fitting the concentration profile to a hyperbola equation yields apparent $K_d$ values of 6 µM and 9 µM for SA1 and SA2, respectively (FIGS. 5A-5B). To confirm the surface binding mechanism of the peptide hits, the effect of biotin on the fluorescence staining of streptavidin-coated beads by SA1/2 was assessed. The microscopic images revealed marginal differences in fluorescence intensity with and without biotin (FIG. 6), indicating the peptide probes do not bind into the biotin-binding pocket of streptavidin, consistent with the postulated surface binding mechanism. To shed light on the iminoboronate-mediated binding mechanism, the streptavidin-coated beads were treated with acetic acid NHS ester (Ac-NHS, 3 mM) to acetylate the surface lysine residues. The surface acetylation completely abolished the fluorescence staining of the beads by SA1 (FIG. 7). Similarly, acetylation greatly reduced the fluorescence staining by SA2 (FIG. 7). Collectively, these data show that the peptide hits (SA1/2) specifically bind streptavidin via covalent conjugation with surface lysines.

Example 2: Targeting Sortase A

Figure 8A:
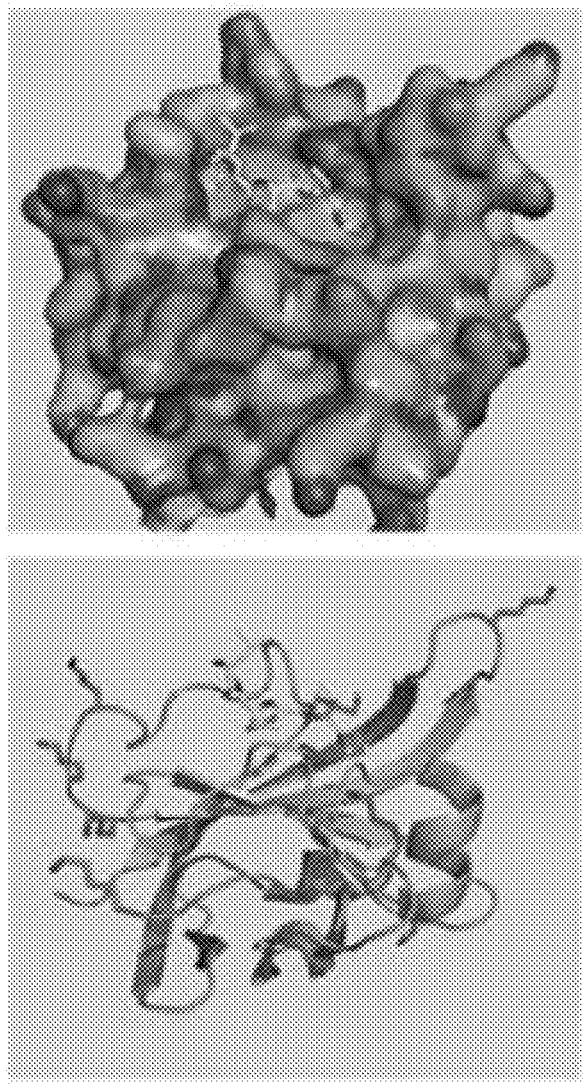
FIGS. 8A-8E show SrtA surface binding by APBA-dimer peptides.

To explore the generality of this approach, the APBA-dimer library was screened against sortase A (SrtA), which is a peptide ligase responsible for attaching proteins to the cell wall of S. Aureus. As a Protein Processing Enzyme, SrtA has a Large and Open Catalytic Site, which has proven difficult to be targeted by small molecules. Several reports in literature describe peptide inhibitors that mimic the substrate peptide sequence and bind to the catalytic site of SrtA with low micromolar potency. With the absence of a deep binding pocket for SrtA, the question of whether this protein can be targeted by an APBA-dimer peptide via surface interactions was addressed in several ways. A quick examination of the SrtA structure revealed 19 surface lysine residues out of a total of ~200 (FIG. 8A).

SrtA was recombinantly expressed with a C-terminal His-tag to facilitate purification. The purified protein was treated with biotin-NHS ester at pH 8.5 to install a biotin handle onto the N-terminus, which was used to immobilize the protein to streptavidin beads for screening. Phage panning was carried out following the same protocol as described above for streptavidin screening. To minimize non-specific binding, a negative selection is added in every cycle of panning, for which the phage library was incubated with SrtA-free beads (streptavidin beads treated with biotin alone instead of biotin-SrtA) before mixing with the SrtA-coated beads. Sequence convergence was seen after round 2 and became more evident after round 3 (Table 4). For comparison, a control library was prepared in which the cysteine residues were alkylated with just iodoacetamide (IA). Three rounds of panning of this control library yielded no recurring sequences at all (Table 3), indicating no potent binders of SrtA exist in this control library. Table 4 shows sequence convergence seen after round 2 and became more evident after round 3.

TABLE 4

Sequence Convergence Targeting Sortase A

| Round 2 | | | Round 3, 1$^{st}$ Trial | | | Round 3, 2$^{nd}$ Trial | | |
|---|---|---|---|---|---|---|---|---|
| Sequence | Number of Occurrences | SEQ ID NO. | Sequence | Number of Occurrences | SEQ ID NO. | Sequence | Number of Occurrences | SEQ ID NO. |
| CTPNKTPCK | 2 | 17 | CDRTTRHLC | 1 | 27 | CLNSSQPSC | 3 | 38 |
| CHPVSGQKC* | 1 | 18 | CAGHNRDRC | 1 | 28 | CYNSPGSVC | 1 | 39 |
| CNWPGEHHC | 1 | 19 | CPAGHSSKC | 1 | 29 | CNLRSEHLC | 1 | 40 |
| CKPSQMPHC | 2 | 20 | CHPVSGQKC* | 2 | 18 | CIQKNTTTC* | 2 | 24 |
| CGFGTQRTC | 1 | 21 | CKLTTQMMC | 1 | 30 | CYNTASAVC | 1 | 41 |
| CSPRPTQTC | 1 | 22 | CSEWSQHSC | 1 | 31 | CHPVSGQKC* | 1 | 18 |
| CEGQRWMQC* | 1 | 23 | CVSNLSKHC | 1 | 32 | CLQPKASQC | 1 | 42 |
| CIQKNTTTC* | 1 | 24 | CTSQKAQQC | 1 | 33 | CGYSSFNRC | 1 | 43 |
| CLPMTKHVC | 1 | 25 | CLKNQSDQC | 1 | 34 | CGVGNARVC | 1 | 44 |
| CHHLKNTSC | 1 | 26 | CMTSSKSSC | 2 | 35 | CHAANGPIC | 1 | 45 |
| | | | CEGQRWMQC* | 1 | 23 | CTGVAPRNC | 1 | 46 |
| | | | CNTGSPYEC | 1 | 36 | CGYSTSWSC | 1 | 47 |
| | | | CPMIDRLHC | 1 | 37 | CAPNGNHRC | 1 | 48 |
| | | | | | | CMSGHGLPC | 1 | 49 |

*Sequence appeared in multiple rounds of experiments.

Table 5 shows three rounds of panning of the control library yielded no recurring sequences between rounds.

TABLE 5

Panning of Control Library

| 2$^{nd}$ Round Output | | | 3$^{rd}$ Round Output, 1$^{st}$ Trial | | |
|---|---|---|---|---|---|
| Sequence | Number of Appearances | SEQ ID NO. | Sequence | Number of Appearances | SEQ ID NO. |
| CMSTGLSSC | 2 | 50 | CHKTEHRSC | 2 | 58 |
| CQTDSTSSC | 2 | 51 | CWSNGQLMC | 2 | 59 |
| CRDTNHKQC | 2 | 52 | CYSMKYGSC | 2 | 60 |
| CSHRPPSLC | 2 | 53 | CQQTKNYYC | 2 | 61 |

TABLE 5-continued

Panning of Control Library

| 2nd Round Output | | | 3rd Round Output, 1st Trial | | |
|---|---|---|---|---|---|
| Sequence | Number of Appearances | SEQ ID NO. | Sequence | Number of Appearances | SEQ ID NO. |
| CNPKSTLNC | 1 | 54 | CNLVDRGSC | 2 | 62 |
| CLRTYVENC | 1 | 55 | CNDKSHAAC | 1 | 63 |
| CELGTVQSC | 1 | 56 | CRGATPMSC | 1 | 64 |
| CPTNQHHLC | 1 | 57 | CHQKAHPTC | 1 | 65 |
| | | | CFNMFSRVC | 1 | 66 |
| | | | CHVHDYETC | 1 | 67 |

Figure 8B:
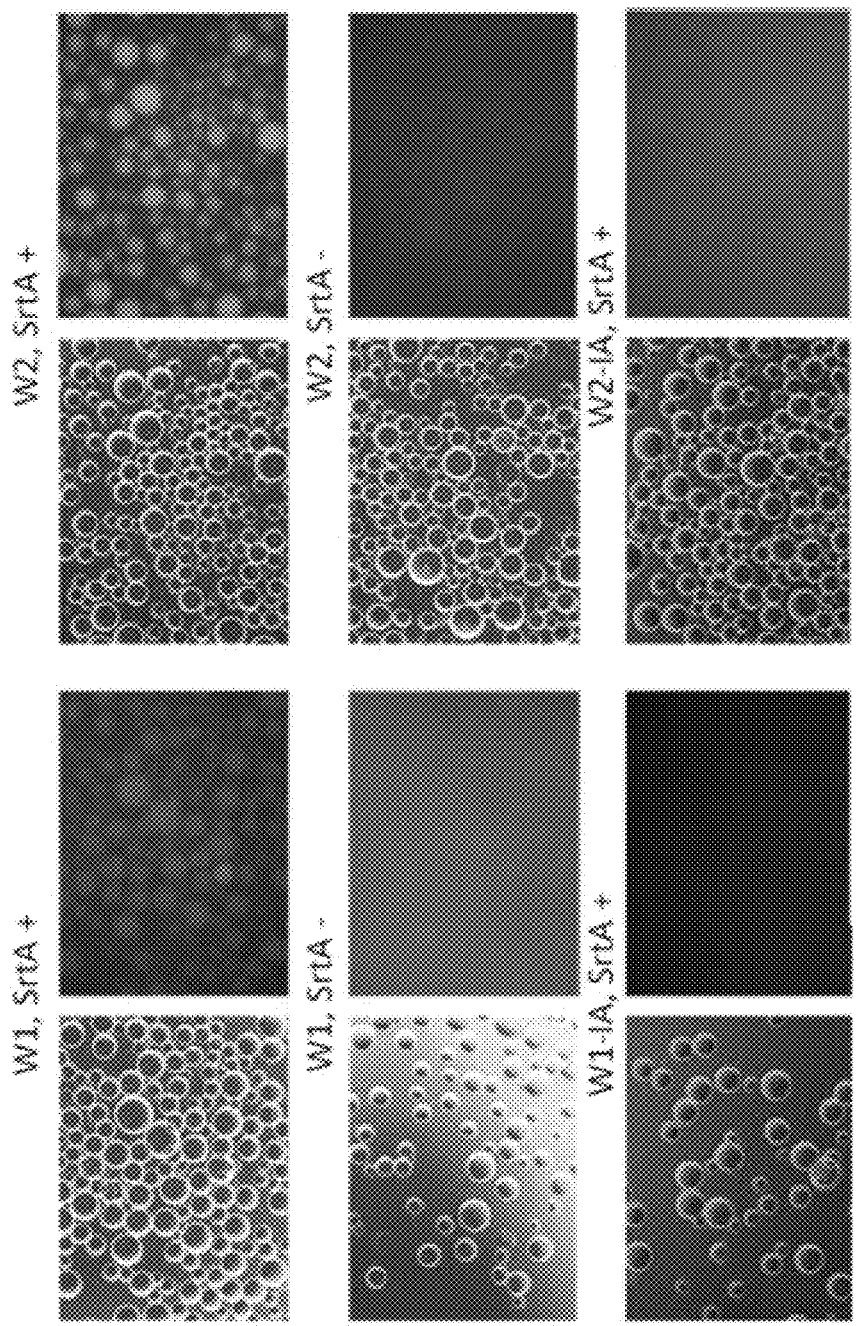
Figure 9:
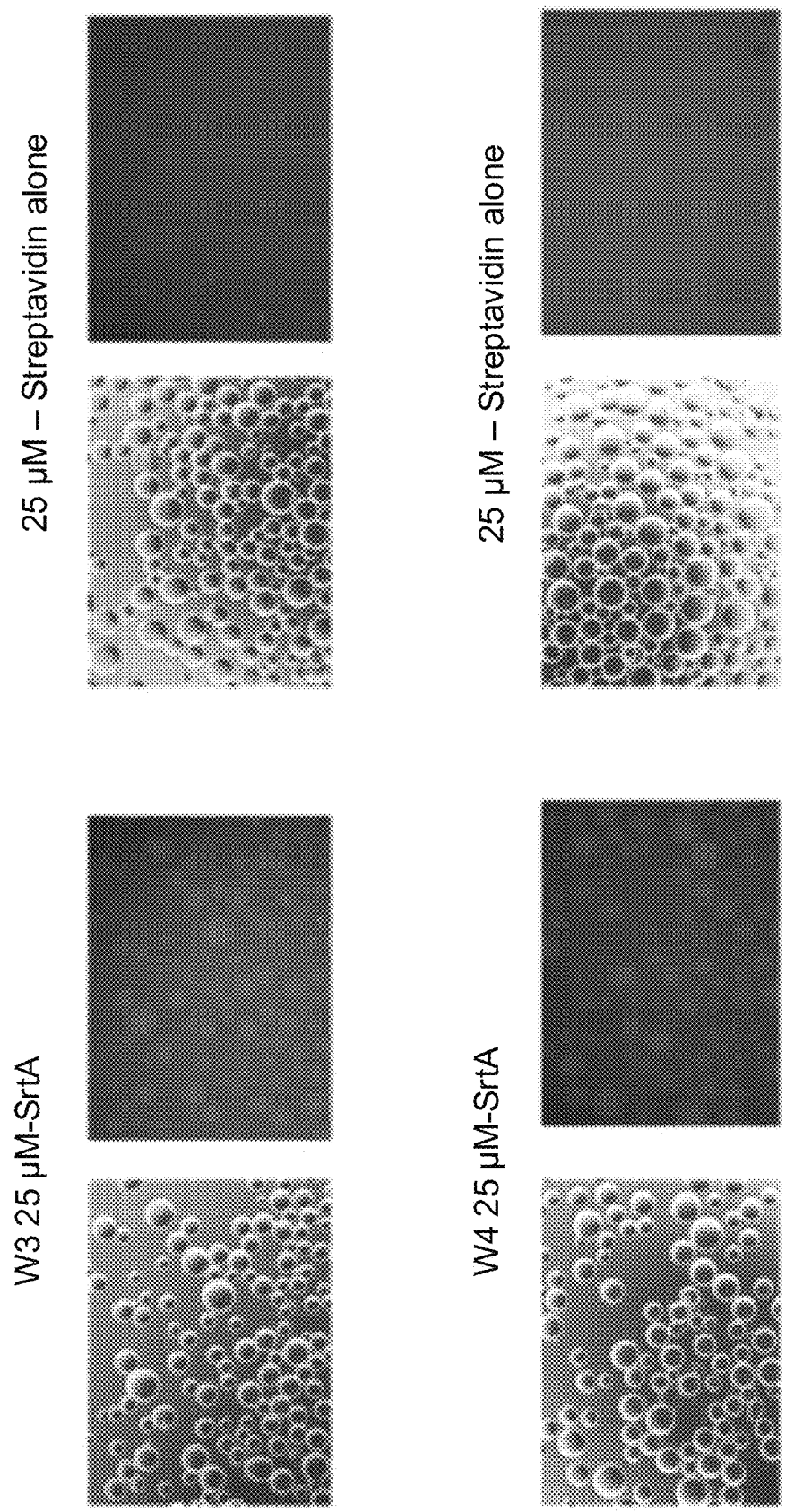
FIG. 9 shows W3 and W4 as weaker binders of SrtA, eliciting weak fluorescence staining of SrtA-coated beads. W3 and W4 represent peptide hits binding SrtA.

The four peptide hits (W1-4, Table 3) that appeared most frequently were chosen for validation, for which the peptides were synthesized in pure forms and characterized for SrtA binding using two complementary methods. First, the fluorescently labeled peptides were tested for staining SrtA-coated beads, imitating the conditions used for phage panning. Under a fluorescence microscope, W1 and W2 at 25 µM afforded strong fluorescence staining of the SrtA-coated beads (FIG. 8B). Comparatively, W3 and W4 elicited much lower fluorescence staining of the beads, although the fluorescence staining is SrtA-specific as the peptide hits afforded no fluorescence staining of the streptavidin beads alone (FIG. 9). Importantly, without SrtA coating, W1 and W2 elicited little binding to the agarose beads although there is still a layer of protein (streptavidin) on the beads. Furthermore, the SrtA binding of W1 and W2 absolutely requires the APBA moieties as the peptide analogues (W1/2-IA) with just iodoacetamide-modified cysteines showed no binding to SrtA coated beads under the same conditions (FIG. 8B), consistent with the fact that no peptide hits were identified from screening of the IA modified library.

Figure 8C:
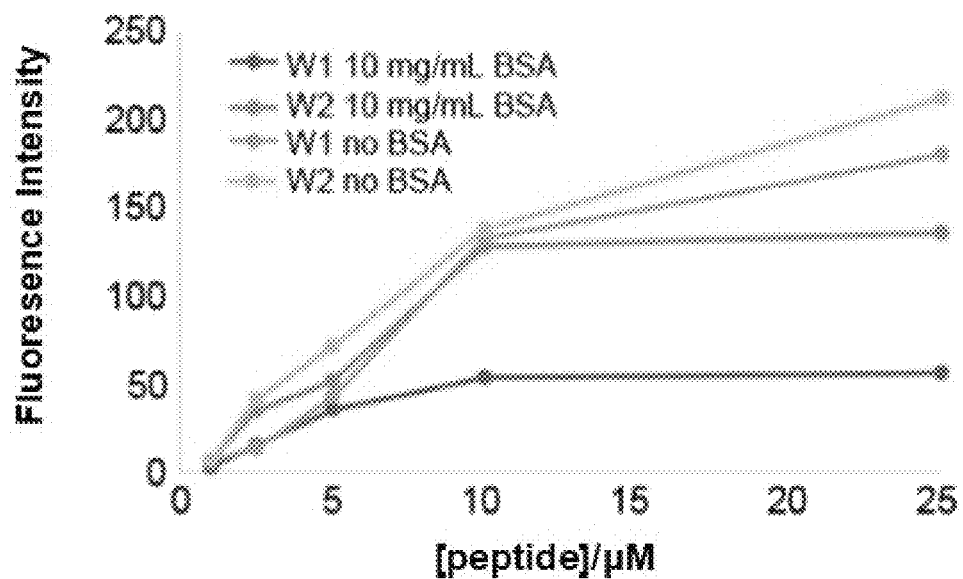
Figure 8D:
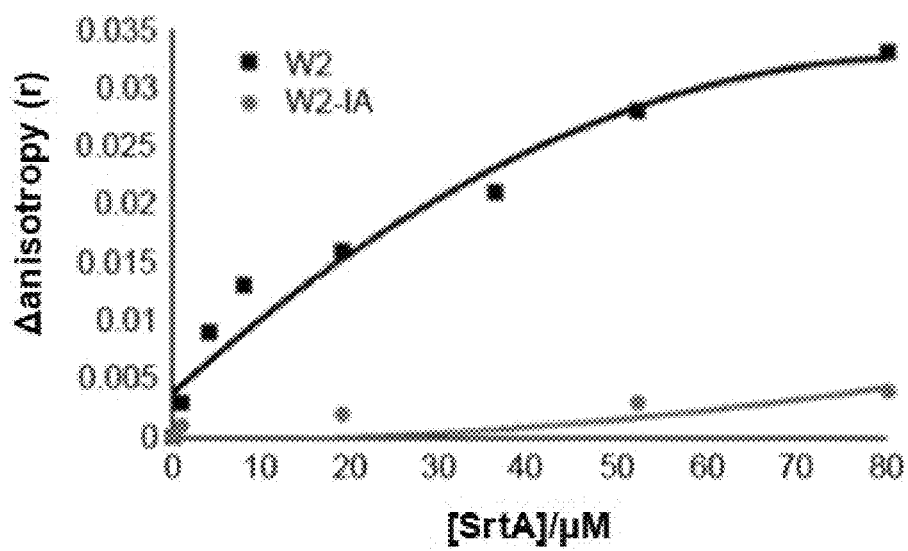

To quantify the binding potency, peptides of various concentrations were evaluated for staining SrtA-coated beads. Plotting the mean fluorescence intensity of the beads against peptide concentration gave the binding curves; fitting these yielded the $K_d$ values of 14 µM for both W1 and W2 (FIG. 8C). Remarkably, W2 was found to stain the SrtA coated beads even in the presence of 10 mg/mL BSA, while greater inhibition was observed for W1-SrtA binding upon BSA addition (FIG. 8C). The peptide-SrtA binding was further analyzed using fluorescence polarization, for which SrtA of increasing concentrations was added to the peptide solution and the fluorescence anisotropy was recorded on a fluorimeter (FIG. 8D). Fitting the binding curves generated through fluorescence polarization experiments gave a $K_d$ value of 12 µM for W2, essentially identical to the results from the microscopy experiments. Also consistent with the microscopic images shown in FIG. 8B, the control peptide W2-IA showed little binding at all concentrations tested (FIG. 8D).

Figure 8E:
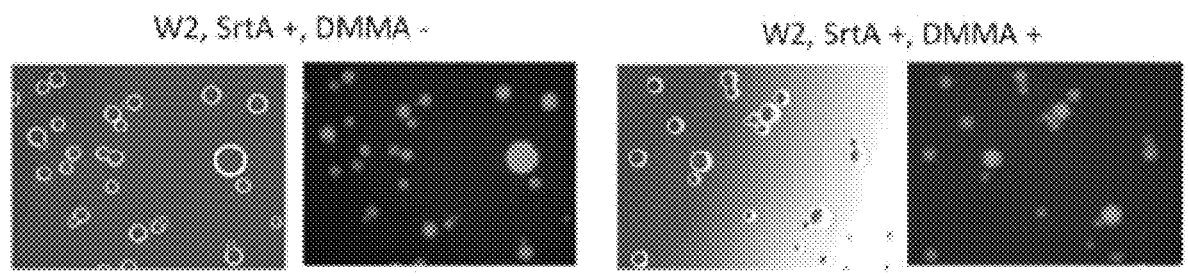

To probe the peptides' binding site on SrtA, a competition experiment was designed using a known small molecule inhibitor of SrtA, DMMA (FIG. 8E). Interestingly, DMMA addition elicited no inhibition of the SrtA binding by W1 or W2. This results suggest that the surface of SrtA is equally, if not more amenable to biding by the APBA-dimer peptides. The low micromolar affinity exhibited by the W1/2, although not still modest, showcases the potential of specific protein recognition by targeting protein surfaces. Detailed binding mode of W1/2 to SrtA remains to be further investigated.

Example 3: Targeting HBD3

Encouraged by the results of the two model proteins, the potential of the APBA-dimer library to target the surface of small peptide/protein hormones (e.g., insulin) was examined, as these are particularly difficult for bind synthetic molecules due to their small size, polar surface, and the lack of binding pockets. However, as these peptide/protein hormones play central roles in various signaling pathways, having molecular probes and inhibitors to control their function is highly desirable and may offer innovative solutions to a number of devastating diseases.

Human beta-defensin 3 (HBD3) is a small protein of only 45 residues. Previously considered as just a host defense peptide against bacteria, HBD3 has been found to also exhibit chemotactic activities. In particular, HBD3 is reported to be overexpressed in and released by oral precancerous lesions and oral cancer cells at the invasive front. In contrast, the production of close homologue HBD2 at such sites is much reduced. HBD3 is believed to promote tumorigenesis by regulating tumor-associated macrophages through its interaction with the chemokine inhibitor CCR2.

Figure 10A:
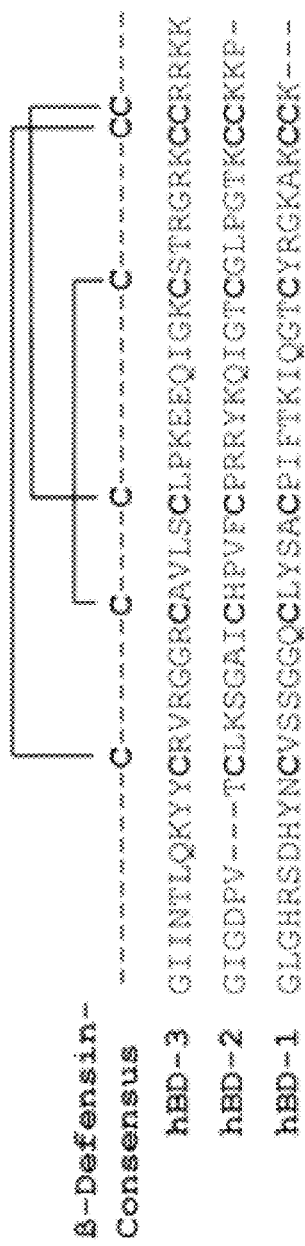
FIGS. 10A-10C show screening of the APBA dimer library against the challenging-to-target human beta defensin-3 (HBD3) protein yields selective and potent peptide hits. An exemplary peptide hit showing selective binding to HBD3 over HBD2, even in the presence of fetal bovine serum (FBS).
Figure 10B:
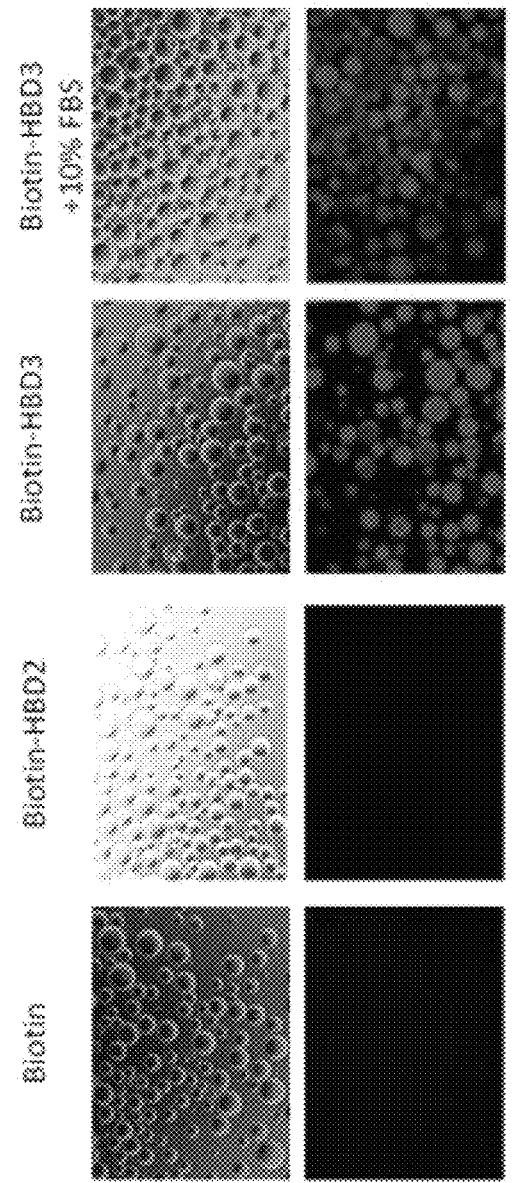
Figure 10C:
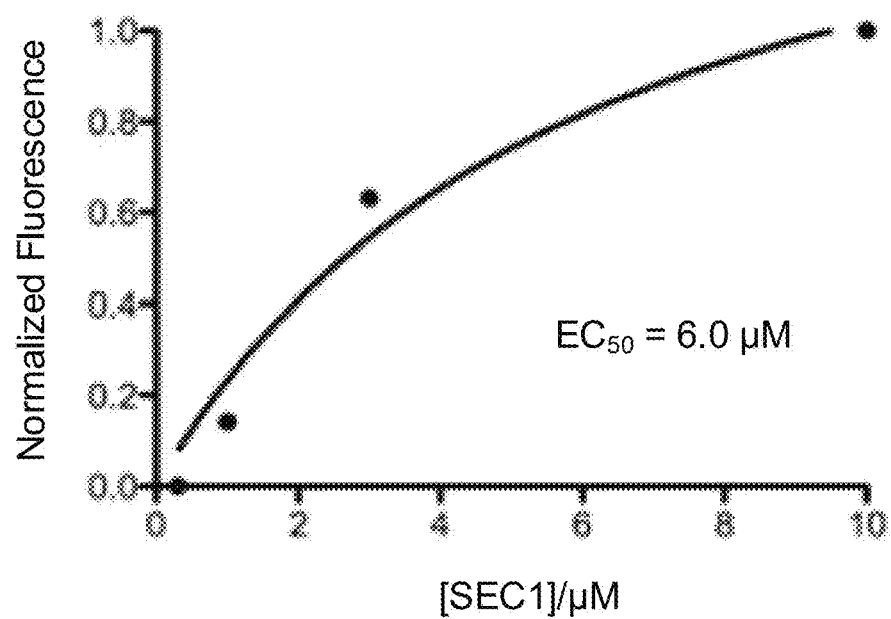

Inhibiting the HBD3-CCR2 interaction presents a compelling strategy to thwart the HBD3-promoted cancer growth. To facilitate phage panning, we chemically synthesized HBD3 with an N-terminal biotin, through which HBD3 is immobilized onto streptavidin beads. Panning of the APBA-dimer library was performed as described earlier for other proteins. To ensure specificity, we included a negative selection starting from round 2, in which the APBA dimer library was incubated with streptavidin beads pretreated with biotin. The unbound phage was collected and subjected to HBD3 coated beads. The decoding and peptide hit synthesis were carried out following the same protocol described above. The peptides' binding to HBD3 was examined using fluorescence microscopy. Similar to the previously-described SrtA studies, two of the four peptides examined showed low micromolar binding to HBD3 (FIGS. 10A-10C), with SEC2 and SEC3 exhibiting $K_d$ values of 6 and 10 µM respectively. Human HBD-1, HBD-2, and HBD-3 consensus sequences shown in FIG. 10A correspond with SEQ ID NOs. 76, 77, and 78, respectively.

Importantly, SEC2 showed remarkable specificity towards HBD3, with strong staining of the HBD3-coated beads in the presence of 10 mg/mL BSA. Furthermore, under the same experimental conditions, SEC2 elicited no detectable binding to HBD2-coated beads despite the sequence and structure similarity of the two HBDs.

REFERENCES

1. Akcay, G. et al. *Nat Chem Biol* 2016, 12, 931-936.
2. Arkin, M. R. et al. *Chem Biol* 2014, 21, 1102-14.
3. Arkin, M. R. et al. *Nat Rev Drug Discov* 2004, 3, 301-17.
4. Bandyopadhyay, A. et al. *Curr Opin Chem Biol* 2016, 34, 110-116.
5. Bandyopadhyay, A. et al. *Nature communications* 2015, 6, 6561.
6. Cal, P. M. et al. *Chemistry* 2015, 21, 8182-7.
7. Cambray, S. et al. *Acc Chem Res* 2018, 51, 2198-2206.
8. Cascioferro, S. et al. *J Med Chem* 2015, 58, 9108-23.
9. Crews, C. M. *Chem Biol* 2010, 17, 551-5.
10. DeLano, W. L. et al. *Science* 2000, 287, 1279-1283.
11. Heinis, C. et al. *Nat Chem Biol* 2009, 5, 502-7.
12. Jin, G. et al. *PLoS One* 2010, 5, e10993.
13. Kawakami, T. et al. *Nat Chem Biol* 2009, 5, 888-90.

14. McCarthy, K. A. et al. *J Am Chem Soc* 2018, 140, 6137-6145.
15. Serafimova, I. M. et al. *Nat Chem Biol* 2012, 8, 471-6.
16. Wang, J. et al. *Frontiers in Microbiology* 2018, 9.
17. Wu, Z. et al. *Proceedings of the National Academy of Sciences* 2003, 100, 8880-8885.
18. Yang, J. et al. *Medicinal Research Reviews* 2019, 39, 265-301.
19. Zhang, J. et al. *Proceedings of the National Academy of Sciences* 2014, 111, 13517-13522.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

What is claimed is:

1. A drug screening method for selection of a therapeutic peptide for binding a protein of interest, the method comprising:
   screening a phage display library comprising phage particles comprising phage display peptides comprising at least one acetylphenylboronic acid (APBA) modified cysteine residue, wherein the APBA modified cysteine residue binds to an isolated and/or purified form of the protein of interest; and
   selecting peptide binders with submicromolar affinity against the isolated and/or purified form of the protein of interest;
   wherein the selected peptide binders are inhibitors targeting the protein of interest.

2. The method of claim 1, wherein the phage display peptides comprise two APBA modified cysteine residues.

3. The method of claim 1, wherein the phage display peptides comprise a peptide sequence given by:

$XC^*(X)_nC^*(X)_m$, wherein C* represents an APBA modified cysteine residue; wherein each instance of X is independently selected from A, D, E, F, G, H, I, K, L, M, N, P, Q, R, S, T, V, W, and Y.

4. The method of claim 1, wherein the at least one APBA modified cysteine residue has a structure given by a formula:

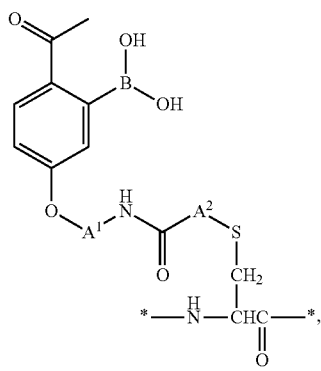

wherein each of $A^1$ and $A^2$ are independently C1-C6 alkyl and the asterisks signify additional portions of the peptide or attachment to the phage particle.

5. The method of claim 4, wherein the APBA modified cysteine residue has a structure given by a formula:

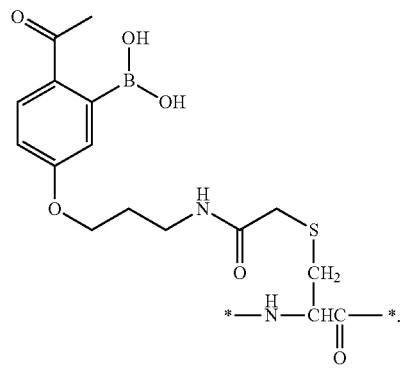

6. The method of claim 1, wherein the protein of interest is selected from the group consisting of a bacterial protein, a viral protein, a fungal protein, a misfolded protein, an overexpressed protein, a protein expressed by a cancer cell, or a combination thereof.

7. The drug screening method of claim 1, wherein the selected peptide binders are further conjugated with a therapeutic residue targeting the protein of interest.

* * * * *

SEQUENCE LISTING

```
<160> NUMBER OF SEQ ID NOS: 85

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Cys Asp Gly Arg Pro Asp Arg Ala Cys
1               5

<210> SEQ ID NO 2
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Cys Thr Pro Arg Ser Ala Asn Tyr Cys
1               5

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Cys Met Ala Thr Pro Thr Arg Gly Cys
1               5

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Cys Val Gly Pro His Asp Lys Thr Cys
1               5

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 5

Cys Thr Lys Val Met Asp Lys Leu Cys
1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Cys Glu Pro Arg Ser Leu Ala Asn Cys
1               5

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Cys Pro Thr Leu Lys Pro Asn Met Cys
1               5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Cys Asn His Glu Leu Val Thr Val Cys
1               5

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Cys Asp Val His Asn Pro Ser Ser Cys
1               5

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Cys Gln Pro Ala Arg His Asn Asn Cys
1               5

<210> SEQ ID NO 11
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Cys Asp Asp Asp Met Ala Pro Ser Cys
1               5

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Cys Ser Thr Pro Ser Ser Gln Ser Cys
1               5

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Cys Gln Ser Ser Pro Asn Pro Leu Cys
1               5

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Cys Asn Gly Trp Pro Gly Ala Ser Cys
1               5

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Cys Ser Lys Gln Asp Leu Trp Gln Cys
1               5

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Cys Val Pro Thr Pro Gly Met Thr Cys
```

```
1               5
```

<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

```
Cys Thr Pro Asn Lys Thr Pro Cys Lys
1               5
```

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

```
Cys His Pro Val Ser Gly Gln Lys Cys
1               5
```

<210> SEQ ID NO 19
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

```
Cys Asn Trp Pro Gly Glu His His Cys
1               5
```

<210> SEQ ID NO 20
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

```
Cys Lys Pro Ser Gln Met Pro His Cys
1               5
```

<210> SEQ ID NO 21
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

```
Cys Gly Phe Gly Thr Gln Arg Thr Cys
1               5
```

<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 22

Cys Ser Pro Arg Pro Thr Gln Thr Cys
1               5

<210> SEQ ID NO 23
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Cys Glu Gly Gln Arg Trp Met Gln Cys
1               5

<210> SEQ ID NO 24
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Cys Ile Gln Lys Asn Thr Thr Thr Cys
1               5

<210> SEQ ID NO 25
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Cys Leu Pro Met Thr Lys His Val Cys
1               5

<210> SEQ ID NO 26
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Cys His His Leu Lys Asn Thr Ser Cys
1               5

<210> SEQ ID NO 27
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Cys Asp Arg Thr Thr Arg His Leu Cys
1               5

<210> SEQ ID NO 28

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Cys Ala Gly His Asn Arg Asp Arg Cys
1               5

<210> SEQ ID NO 29
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Cys Pro Ala Gly His Ser Ser Lys Cys
1               5

<210> SEQ ID NO 30
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Cys Lys Leu Thr Thr Gln Met Met Cys
1               5

<210> SEQ ID NO 31
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Cys Ser Glu Trp Ser Gln His Ser Cys
1               5

<210> SEQ ID NO 32
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Cys Val Ser Asn Leu Ser Lys His Cys
1               5

<210> SEQ ID NO 33
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33
```

Cys Thr Ser Gln Lys Ala Gln Gln Cys
1               5

<210> SEQ ID NO 34
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Cys Leu Lys Asn Gln Ser Asp Gln Cys
1               5

<210> SEQ ID NO 35
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Cys Met Thr Ser Ser Lys Ser Ser Cys
1               5

<210> SEQ ID NO 36
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Cys Asn Thr Gly Ser Pro Tyr Glu Cys
1               5

<210> SEQ ID NO 37
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Cys Pro Met Ile Asp Arg Leu His Cys
1               5

<210> SEQ ID NO 38
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Cys Leu Asn Ser Ser Gln Pro Ser Cys
1               5

<210> SEQ ID NO 39
<211> LENGTH: 9
<212> TYPE: PRT
<213> ORGANISM: Artificial Sequence
<220> FEATURE:

-continued

```
<223> OTHER INFORMATION: Description of Artificial Sequence: Synthetic
      peptide

<400> SEQUENCE: 39

Cys Tyr Asn Ser Pro Gly Ser Val Cys
1               5

<210> SEQ ID NO 40
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Cys Asn Leu Arg Ser Glu His Leu Cys
1               5

<210> SEQ ID NO 41
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Cys Tyr Asn Thr Ala Ser Ala Val Cys
1               5

<210> SEQ ID NO 42
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Cys Leu Gln Pro Lys Ala Ser Gln Cys
1               5

<210> SEQ ID NO 43
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Cys Gly Tyr Ser Ser Phe Asn Arg Cys
1               5

<210> SEQ ID NO 44
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Cys Gly Val Gly Asn Ala Arg Val Cys
1               5
```

```
<210> SEQ ID NO 45
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Cys His Ala Ala Asn Gly Pro Ile Cys
1               5

<210> SEQ ID NO 46
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Cys Thr Gly Val Ala Pro Arg Asn Cys
1               5

<210> SEQ ID NO 47
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Cys Gly Tyr Ser Thr Ser Trp Ser Cys
1               5

<210> SEQ ID NO 48
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Cys Ala Pro Asn Gly Asn His Arg Cys
1               5

<210> SEQ ID NO 49
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Cys Met Ser Gly His Gly Leu Pro Cys
1               5

<210> SEQ ID NO 50
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50
```

```
Cys Met Ser Thr Gly Leu Ser Ser Cys
1               5

<210> SEQ ID NO 51
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Cys Gln Thr Asp Ser Thr Ser Ser Cys
1               5

<210> SEQ ID NO 52
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Cys Arg Asp Thr Asn His Lys Gln Cys
1               5

<210> SEQ ID NO 53
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Cys Ser His Arg Pro Pro Ser Leu Cys
1               5

<210> SEQ ID NO 54
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Cys Asn Pro Lys Ser Thr Leu Asn Cys
1               5

<210> SEQ ID NO 55
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Cys Leu Arg Thr Tyr Val Glu Asn Cys
1               5

<210> SEQ ID NO 56
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 56

Cys Glu Leu Gly Thr Val Gln Ser Cys
1               5

<210> SEQ ID NO 57
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Cys Pro Thr Asn Gln His His Leu Cys
1               5

<210> SEQ ID NO 58
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Cys His Lys Thr Glu His Arg Ser Cys
1               5

<210> SEQ ID NO 59
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Cys Trp Ser Asn Gly Gln Leu Met Cys
1               5

<210> SEQ ID NO 60
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Cys Tyr Ser Met Lys Tyr Gly Ser Cys
1               5

<210> SEQ ID NO 61
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Cys Gln Gln Thr Lys Asn Tyr Tyr Cys
1               5
```

```
<210> SEQ ID NO 62
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Cys Asn Leu Val Asp Arg Gly Ser Cys
1               5

<210> SEQ ID NO 63
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Cys Asn Asp Lys Ser His Ala Ala Cys
1               5

<210> SEQ ID NO 64
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Cys Arg Gly Ala Thr Pro Met Ser Cys
1               5

<210> SEQ ID NO 65
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Cys His Gln Lys Ala His Pro Thr Cys
1               5

<210> SEQ ID NO 66
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Cys Phe Asn Met Phe Ser Arg Val Cys
1               5

<210> SEQ ID NO 67
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 67

Cys His Val His Asp Tyr Glu Thr Cys
1               5

<210> SEQ ID NO 68
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: (2-acetyl-5-(3-(2-
      iodoacetamido)propoxy)phenyl)boronic acid modified cysteine
<220> FEATURE:
<221> NAME/KEY: MOD_RES
<222> LOCATION: (10)..(10)
<223> OTHER INFORMATION: (2-acetyl-5-(3-(2-
      iodoacetamido)propoxy)phenyl)boronic acid modified cysteine
<220> FEATURE:
<221> NAME/KEY: MOD_RES
<222> LOCATION: (14)..(14)
<223> OTHER INFORMATION: fluorescently labeled 2,3-diaminopropionic acid

<400> SEQUENCE: 68

Ala Cys His Pro Val Ser Gly Gln Lys Cys Gly Gly Gly Xaa
1               5                   10

<210> SEQ ID NO 69
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: (2-acetyl-5-(3-(2-
      iodoacetamido)propoxy)phenyl)boronic acid modified cysteine
<220> FEATURE:
<221> NAME/KEY: MOD_RES
<222> LOCATION: (10)..(10)
<223> OTHER INFORMATION: (2-acetyl-5-(3-(2-
      iodoacetamido)propoxy)phenyl)boronic acid modified cysteine
<220> FEATURE:
<221> NAME/KEY: MOD_RES
<222> LOCATION: (14)..(14)
<223> OTHER INFORMATION: fluorescently labeled 2,3-diaminopropionic acid

<400> SEQUENCE: 69

Ala Cys Leu Asn Ser Ser Gln Pro Ser Cys Gly Gly Gly Xaa
1               5                   10

<210> SEQ ID NO 70
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: (2-acetyl-5-(3-(2-
      iodoacetamido)propoxy)phenyl)boronic acid modified cysteine
<220> FEATURE:
<221> NAME/KEY: MOD_RES
<222> LOCATION: (10)..(10)
<223> OTHER INFORMATION: (2-acetyl-5-(3-(2-
      iodoacetamido)propoxy)phenyl)boronic acid modified cysteine
```

```
-continued

<220> FEATURE:
<221> NAME/KEY: MOD_RES
<222> LOCATION: (14)..(14)
<223> OTHER INFORMATION: fluorescently labeled 2,3-diaminopropionic acid

<400> SEQUENCE: 70

Ala Cys Ile Gln Lys Asn Thr Thr Thr Cys Gly Gly Gly Xaa
1               5                   10

<210> SEQ ID NO 71
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: (2-acetyl-5-(3-(2-
      iodoacetamido)propoxy)phenyl)boronic acid modified cysteine
<220> FEATURE:
<221> NAME/KEY: MOD_RES
<222> LOCATION: (10)..(10)
<223> OTHER INFORMATION: (2-acetyl-5-(3-(2-
      iodoacetamido)propoxy)phenyl)boronic acid modified cysteine
<220> FEATURE:
<221> NAME/KEY: MOD_RES
<222> LOCATION: (14)..(14)
<223> OTHER INFORMATION: fluorescently labeled 2,3-diaminopropionic acid

<400> SEQUENCE: 71

Ala Cys Thr Pro Asn Lys Thr Pro Lys Cys Gly Gly Gly Xaa
1               5                   10

<210> SEQ ID NO 72
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: (2-acetyl-5-(3-(2-
      iodoacetamido)propoxy)phenyl)boronic acid modified cysteine
<220> FEATURE:
<221> NAME/KEY: MOD_RES
<222> LOCATION: (10)..(10)
<223> OTHER INFORMATION: (2-acetyl-5-(3-(2-
      iodoacetamido)propoxy)phenyl)boronic acid modified cysteine
<220> FEATURE:
<221> NAME/KEY: MOD_RES
<222> LOCATION: (14)..(14)
<223> OTHER INFORMATION: fluorescently labeled 2,3-diaminopropionic acid

<400> SEQUENCE: 72

Ala Cys Thr Pro Arg Ser Ala Asn Tyr Cys Gly Gly Gly Xaa
1               5                   10

<210> SEQ ID NO 73
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: (2-acetyl-5-(3-(2-
      iodoacetamido)propoxy)phenyl)boronic acid modified cysteine
```

-continued

```
<220> FEATURE:
<221> NAME/KEY: MOD_RES
<222> LOCATION: (10)..(10)
<223> OTHER INFORMATION: (2-acetyl-5-(3-(2-
      iodoacetamido)propoxy)phenyl)boronic acid modified cysteine
<220> FEATURE:
<221> NAME/KEY: MOD_RES
<222> LOCATION: (14)..(14)
<223> OTHER INFORMATION: fluorescently labeled 2,3-diaminopropionic acid

<400> SEQUENCE: 73

Ala Cys Asp Gly Arg Pro Asp Arg Ala Cys Gly Gly Gly Xaa
1               5                   10

<210> SEQ ID NO 74
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: iodoacetamide modified cysteine
<220> FEATURE:
<221> NAME/KEY: MOD_RES
<222> LOCATION: (10)..(10)
<223> OTHER INFORMATION: (2-acetyl-5-(3-(2-
      iodoacetamido)propoxy)phenyl)boronic acid modified cysteine
<220> FEATURE:
<221> NAME/KEY: MOD_RES
<222> LOCATION: (14)..(14)
<223> OTHER INFORMATION: fluorescently labeled 2,3-diaminopropionic acid

<400> SEQUENCE: 74

Ala Cys Thr Pro Arg Ser Ala Asn Tyr Cys Gly Gly Gly Xaa
1               5                   10

<210> SEQ ID NO 75
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: iodoacetamide modified cysteine
<220> FEATURE:
<221> NAME/KEY: MOD_RES
<222> LOCATION: (10)..(10)
<223> OTHER INFORMATION: (2-acetyl-5-(3-(2-
      iodoacetamido)propoxy)phenyl)boronic acid modified cysteine
<220> FEATURE:
<221> NAME/KEY: MOD_RES
<222> LOCATION: (14)..(14)
<223> OTHER INFORMATION: fluorescently labeled 2,3-diaminopropionic acid

<400> SEQUENCE: 75

Ala Cys Asp Gly Arg Pro Asp Arg Ala Cys Gly Gly Gly Xaa
1               5                   10

<210> SEQ ID NO 76
<211> LENGTH: 45
<212> TYPE: PRT
<213> ORGANISM: Homo sapiens

<400> SEQUENCE: 76

Gly Ile Ile Asn Thr Leu Gln Lys Tyr Tyr Cys Arg Val Arg Gly Gly
1               5                   10                  15
```

```
Arg Cys Ala Val Leu Ser Cys Leu Pro Lys Glu Glu Gln Ile Gly Lys
                20                  25                  30

Cys Ser Thr Arg Gly Arg Lys Cys Cys Arg Arg Lys Lys
        35                  40                  45

<210> SEQ ID NO 77
<211> LENGTH: 41
<212> TYPE: PRT
<213> ORGANISM: Homo sapiens

<400> SEQUENCE: 77

Gly Ile Gly Asp Pro Val Thr Cys Leu Lys Ser Gly Ala Ile Cys His
1               5                   10                  15

Pro Val Phe Cys Pro Arg Arg Tyr Lys Gln Ile Gly Thr Cys Gly Leu
                20                  25                  30

Pro Gly Thr Lys Cys Cys Lys Lys Pro
                35                  40

<210> SEQ ID NO 78
<211> LENGTH: 42
<212> TYPE: PRT
<213> ORGANISM: Homo sapiens

<400> SEQUENCE: 78

Gly Leu Gly His Arg Ser Asp His Tyr Asn Cys Val Ser Ser Gly Gly
1               5                   10                  15

Gln Cys Leu Tyr Ser Ala Cys Pro Ile Phe Thr Lys Ile Gln Gly Thr
                20                  25                  30

Cys Tyr Arg Gly Lys Ala Lys Cys Cys Lys
                35                  40

<210> SEQ ID NO 79
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Ile Glu Gly Arg
1

<210> SEQ ID NO 80
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Ala Asp Cys Gly
1

<210> SEQ ID NO 81
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81
```

```
Ala Asp Cys Gly Gly Gly
1               5

<210> SEQ ID NO 82
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(8)
<223> OTHER INFORMATION: Any amino acid
<220> FEATURE:
<221> NAME/KEY: SITE
<222> LOCATION: (4)..(8)
<223> OTHER INFORMATION: This region may encompass 1-5 residues

<400> SEQUENCE: 82

Ala Asp Cys Xaa Xaa Xaa Xaa Xaa Gly
1               5

<210> SEQ ID NO 83
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(10)
<223> OTHER INFORMATION: Any amino acid

<400> SEQUENCE: 83

Ile Glu Gly Arg Cys Xaa Xaa Xaa Xaa Xaa Cys
1               5                   10

<210> SEQ ID NO 84
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(12)
<223> OTHER INFORMATION: Any amino acid
<220> FEATURE:
<221> NAME/KEY: SITE
<222> LOCATION: (3)..(12)
<223> OTHER INFORMATION: This region may encompass 5-10 residues
<220> FEATURE:
<221> NAME/KEY: SITE
<222> LOCATION: (14)..(18)
<223> OTHER INFORMATION: This region may encompass 1-5 residues

<400> SEQUENCE: 84

Ala Cys Xaa Xaa Xaa Xaa Xaa Xaa Xaa Xaa Xaa Cys Gly Gly Gly
1               5                   10                  15

Gly Gly

<210> SEQ ID NO 85
<211> LENGTH: 5
<212> TYPE: PRT
<213> ORGANISM: Artificial Sequence
<220> FEATURE:
<223> OTHER INFORMATION: Description of Artificial Sequence: Synthetic
```

```
                peptide
<220> FEATURE:
<221> NAME/KEY: MOD_RES
<222> LOCATION: (2)..(2)
<223> OTHER INFORMATION: 2-acetylphenylboronic acid cysteine
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (4)..(4)
<223> OTHER INFORMATION: 2-acetylphenylboronic acid cysteine

<400> SEQUENCE: 85

Ala Cys Xaa Cys Gly
1               5
```